US010961279B2

(12) United States Patent
Ryttergaard Duch et al.

(10) Patent No.: US 10,961,279 B2
(45) Date of Patent: Mar. 30, 2021

(54) IDENTIFICATION AND ATTENUATION OF THE IMMUNOSUPPRESSIVE DOMAINS IN FUSION PROTEINS OF ENVELOPED RNA VIRUSES

(71) Applicant: iSD Immunotech ApS, Copenhagen N (DK)

(72) Inventors: Mogens Ryttergaard Duch, Risskov (DK); Shervin Bahrami, Aarhus C (DK)

(73) Assignee: ISD Immunotech ApS, Copenhagen N (DK)

( * ) Notice: Subject to any disclaimer, the term of this patent is extended or adjusted under 35 U.S.C. 154(b) by 127 days.

(21) Appl. No.: 15/179,005

(22) Filed: Jun. 10, 2016

(65) Prior Publication Data

US 2016/0362454 A1 Dec. 15, 2016

Related U.S. Application Data

(62) Division of application No. 14/350,151, filed as application No. PCT/DK2012/050381 on Oct. 5, 2012, now abandoned.

(60) Provisional application No. 61/544,441, filed on Oct. 7, 2011.

(30) Foreign Application Priority Data

Oct. 7, 2011 (DK) .......................... PA 2011 70564

(51) Int. Cl.

| | |
|---|---|
| ***C07K 14/005*** | (2006.01) |
| ***C07K 1/00*** | (2006.01) |
| ***C07K 4/02*** | (2006.01) |
| ***A61K 39/12*** | (2006.01) |
| ***C07K 14/08*** | (2006.01) |
| ***C07K 7/08*** | (2006.01) |
| ***C12N 7/00*** | (2006.01) |

(52) U.S. Cl.

CPC ............ *C07K 14/005* (2013.01); *A61K 39/12* (2013.01); *C07K 1/00* (2013.01); *C07K 4/02* (2013.01); *C07K 7/08* (2013.01); *C07K 14/08* (2013.01); *C12N 7/00* (2013.01); *C12N 2760/12121* (2013.01); *C12N 2760/12122* (2013.01); *C12N 2760/12221* (2013.01); *C12N 2760/12222* (2013.01); *C12N 2760/16121* (2013.01); *C12N 2760/16122* (2013.01); *C12N 2760/16134* (2013.01); *C12N 2760/16221* (2013.01); *C12N 2760/16222* (2013.01); *C12N 2760/16234* (2013.01); *C12N 2760/16321* (2013.01); *C12N 2760/16322* (2013.01); *C12N 2770/24121* (2013.01); *C12N 2770/24122* (2013.01); *C12N 2770/24134* (2013.01); *C12N 2770/24221* (2013.01); *C12N 2770/24222* (2013.01); *C12N 2770/24234* (2013.01); *C12N 2770/24321* (2013.01); *C12N 2770/24322* (2013.01); *C12N 2770/28021* (2013.01); *C12N 2770/28034* (2013.01); *C12N 2770/36121* (2013.01); *C12N 2770/36122* (2013.01); *C12N 2770/36221* (2013.01); *C12N 2770/36222* (2013.01)

(58) Field of Classification Search

CPC .......... C07K 14/005; C07K 1/00; C07K 4/02; C07K 14/08; C07K 7/08; A61K 39/12; C12N 7/00; C12N 2760/16134; C12N 2770/24234; C12N 2760/12121; C12N 2760/12122; C12N 2760/12221; C12N 2760/12222; C12N 2760/16121; C12N 2760/16222; C12N 2760/16321; C12N 2760/16322; C12N 2770/24221; C12N 2770/24321; C12N 2770/24322; C12N 2770/36121; C12N 2770/36122; C12N 2770/36221; C12N 2770/36222; C12N 2760/16221; C12N 2760/16234; C12N 2770/24121; C12N 2770/28021; C12N 2270/28034; C12N 2760/16122; C12N 2770/24122; C12N 2770/24134; C12N 2770/24222

See application file for complete search history.

(56) References Cited

U.S. PATENT DOCUMENTS

| | | |
|---|---|---|
| 4,822,606 A | 4/1989 | Snyderman et al. |
| 7,943,148 B1 | 5/2011 | Sagripanti et al. |

(Continued)

FOREIGN PATENT DOCUMENTS

| | | |
|---|---|---|
| WO | 2001019380 A2 | 3/2001 |
| WO | 2005058968 A1 | 6/2005 |
| WO | 2006042156 A3 | 10/2006 |

(Continued)

OTHER PUBLICATIONS

By Li et al. (Membrane Structures of the Hemifusion-Inducing Fusion Peptide Mutant G1S and the Fusion-Blocking Mutant G1V of Influenza Virus Hemagglutinin Suggest a Mechanism for Pore Opening in Membrane Fusion. J. Virol., 2005, 79(18): 12065-12076.*

(Continued)

*Primary Examiner* — Rachel B Gill
(74) *Attorney, Agent, or Firm* — Verrill Dana, LLP

(57) ABSTRACT

The present invention relates to enveloped RNA viruses. The invention in particular relates to the generation of superior antigens for mounting an immune response by first identifying then mutating the immunosuppressive domains in fusion proteins of enveloped RNA viruses resulting in decreased immunosuppressive properties of viral envelope proteins from the viruses.

13 Claims, 2 Drawing Sheets

Figure 1:
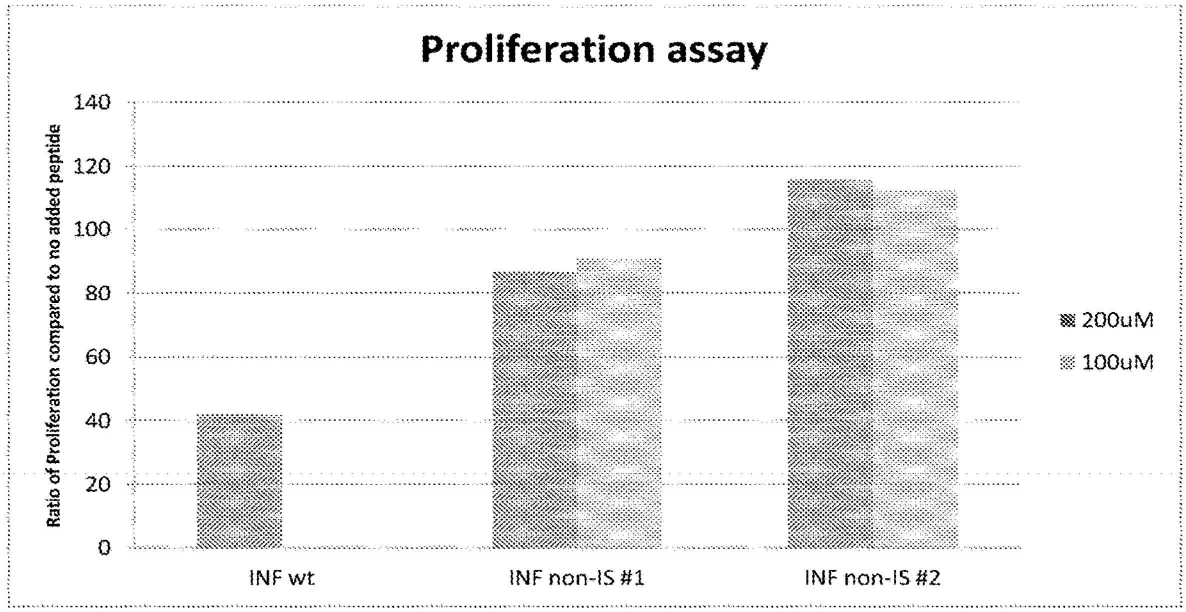

Specification includes a Sequence Listing.

(56) References Cited

U.S. PATENT DOCUMENTS

| | | | |
|---|---|---|---|
| 2007/0185025 | A1 | 8/2007 | Palacios et al. |
| 2008/0241156 | A1 | 10/2008 | Garry et al. |

FOREIGN PATENT DOCUMENTS

| | | | |
|---|---|---|---|
| WO | W02009024534 | | 2/2009 |
| WO | 2009033786 | A2 | 3/2009 |
| WO | 2009065618 | A2 | 5/2009 |
| WO | 2010120262 | A1 | 10/2010 |
| WO | W02011092199 | | 8/2011 |
| WO | 2011120013 | A2 | 9/2011 |

OTHER PUBLICATIONS

Bowie JU, Reidhaar-Olson JF, Lim WA, Sauer RT. Deciphering the message in protein sequences: tolerance to amino acid substitutions. Science. Mar. 16, 1990;247(4948):1306-10.*

Winkler K, Kramer A, Küttner G, Seifert M, Scholz C, Wessner H, Schneider-Mergener J, Höhne W. Changing the antigen binding specificity by single point mutations of an anti-p24 (HIV-1) antibody. J Immunol. Oct. 15, 2000;165(8):4505-14.*

Kussie PH, Parhami-Seren B, Wysocki LJ, Margolies MN. A single engineered amino acid substitution changes antibody fine specificity. J Immunol. Jan. 1, 1994;152(1):146-52.*

Chen Z, Wang J, Bao L, Guo L, Zhang W, Xue Y, Zhou H, Xiao Y, Wang J, Wu F, Deng Y, Qin C, Jin Q. Human monoclonal antibodies targeting the haemagglutinin glycoprotein can neutralize H7N9 influenza virus. Nat Commun. Mar. 30, 2015;6:6714.*

Sela-Culang I, Kunik V, Ofran Y. The structural basis of antibody-antigen recognition. Front Immunol. Oct. 8, 2013;4:302.*

Sirin S, Apgar JR, Bennett EM, Keating AE. AB-Bind: Antibody binding mutational database for computational affinity predictions. Protein Sci. Feb. 2016;25(2):393-409. Epub Nov. 6, 2015.*

Ng PC, Henikoff S. Predicting the effects of amino acid substitutions on protein function. Annu Rev Genomics Hum Genet. 2006;7: 61-80.*

Macosko JC, Kim CH, Shin YK. The membrane topology of the fusion peptide region of influenza hemagglutinin determined by spin-labeling EPR. J Mol Biol. Apr. 18, 1997;267(5):1139-48.*

Dugan VG, et. al. Structural polyprotein [Venezuelan equine encephalitis virus]. GenBank: AGE98163.1, Dep. Feb. 17, 2013.*

Cianciolo GJ, Pizzo SV. Anti-inflammatory and vasoprotective activity of a retroviral-derived peptide, homologous to human endogenous retroviruses: endothelial cell effects. PLoS One. 2012;7(12):e52693. Epub Dec. 20, 2012.*

Steinhauer DA, Wharton SA, Skehel JJ, Wiley DC. Studies of the membrane fusion activities of fusion peptide mutants of influenza virus hemagglutinin. J Virol. Nov. 1995;69(11):6643-51.*

Blinov VM, Krasnov GS, Shargunov AV, Shurdov MA, Zverev VV. [Mechanisms of retroviral immunosuppressive domain-induced immune modulation]. Mol Biol (Mosk). Sep.-Oct. 2013;47(5):707-16. Russian.*

Sapir, Amir et al., Viral and Developmental Cell Fusion Mechanisms: Conservation and Divergens, Developmental Cell, Jan. 2008, pp. 11-21, 14, Elsevier Inc.

Cianciolo, George J. et al., Murine Malignant Cells Synthesize a 19,000-Dalton Protein that is Related to the Immunosuppressive Retroviral Protein, P15E, J. Exp. Med., Sep. 1, 1983, pp. 885-900, vol. 158, The Rockefeller University Press.

Hedebrand, Lynn C. et al., Inhibition of Human Lymphocyte Mitogen and Antigen Response by a 15,000-Dalton Protein from Feline Leukemia Virus, Cancer Research, Feb. 1979, pp. 443-447, 39, American Association for Cancer Research.

Cianciolo, G.J., et al., Macrophage accumulation in mice is inhibited by low molecular weight products from murine leukemia viruses, J Immunol, 1980, pp. 2900-2905, 124(6), The Williams & Wilkins Co., USA.

Mangeney, M. and Heidmann, T., Tumor cells expressing a retroviral envelope escape immune rejection in vivo, Proc Natl Acad Sci, 1998, pp. 14920-14925, 95(25), USA.

Mangeney, M., et al., Placental syncytins: Genetic disjunction between the fusogenic and immunosuppressive activity of retroviral envelope proteins, Proc Natl Acad Sci, 2007, pp. 20534-20539, 104(51), USA.

Cianciolo, G.J., et al., Inhibition of lymphocyte proliferation by a synthetic peptide homologous to retroviral envelope proteins, Science, 1985, pp. 453-455, 230(4724), American Association for the Advancement of Science, USA.

Cianciolo, G.J., Bogerd, H. and Snyderman, R., Human retrovirus-related synthetic peptides inhibit T lymphocyte proliferation, Immunol Lett, 1988, pp. 7-13, 19(1), Elsevier.

Yaddanapudi, K., et al., Implication of a retrovirus-like glycoprotein peptide in the immunopathogenesis of Ebola and Marburg viruses, Faseb Journal, 2006, pp. 2519-2530, 20(14).

Haraguchi, S., et al., Differential modulation of Th1- and Th2-related cytokine mRNA expression by a synthetic peptide homologous to a conserved domain within retroviral envelope protein, Proc Natl Acad Sci, 1995, pp. 3611-3615, 92, USA.

Harell, R.A. et al., Suppression of the respiratory burst of human monocytes by a synthetic peptide homologous to envelope proteins of human and animal retroviruses, J Immunol, 1986, pp. 3517-3520, 136, The American Association of Immunologists.

Kleinerman, E.S. et al., A synthetic peptide homologous to the envelope proteins of retroviruses inhibits monocyte-mediated killing by inactivating interleukin 1, J Immunol, 1987, pp. 2329-2337, 139, The American Association of Immunologists, USA.

Schlecht-Louf, G. et al., Retroviral infection in vivo requires an immune escape virulence factor encrypted in the envelope protein of oncoretroviruses, Proc Natl Acad Sci., Feb. 2010, pp. 3782-3787, 107(8), USA.

Volchkov, V. E. et al., The envelope glycoprotein of Ebola virus contains an immunosuppressive-like domain similar to oncogenic retroviruses, Elsevier Science Publishers, May 1992, pp. 181-184, vol. 305(3); Federation of European Biochemical Societies.

Cross, K. J. et al., Studies on influenza haemagglutinin fusion peptide mutants generated by reverse genetics, EMBO Journal, Aug. 2001, pp. 4432-4442, vol. 20(16), UK and USA.

Seligman, S. J. et al., Constancy and diversity in the flavivirus fusion peptide, Virology Journal, Feb. 2008, vol. 5 (27), BioMed Central.

Schmidt, A. G. et al., Peptide inhibitors of dengue-virus entry target a late-state fusion intermediate, PLoS pathogens, Apr. 2010, vol. 6(4).

Albecka, A. et al., Identification of new functional regions in hepatitis C virus envelope glycoprotein E2, Journal of Virology, Feb. 2011, pp. 1777-1792, vol. 95(4).

Takahashi, S. Conformation of Membrane Fusion-Active 20-Residue Peptides With or Without Lipid Bilayers. Implication of Alpha-Helix Formation for Membrane Fusion. Biochemistry 29 (26), 6257-6264. Jul. 3, 1990.

White JM. Viral and cellular membrane fusion proteins. Annu Rev Physiol. 1990;52:675-97.

Blaise et al. “The envelope of Mason—Pfizer monkey virus has immunosuppressive properties,” Journal of General Virology, vol. 82, pp. 1597-1600 (2001).

Blaise et al. “Functional characterization of two newly identified Human Endogenous Retrovirus coding envelope genes,” Retrovirology, vol. 2, No. 19, 4 pages (2005).

Drummer et al. “Mutagenesis of a conserved fusion peptide-like motif and membrane-proximal heptad-repeat region of hepatitis C virus glycoprotein EI ,” Journal of General Virology, vol. 88, pp. 1144-1148 (2007).

Noone et al. “Novel mechanism of immunosuppression by influenza virus haemagglutinin: selective suppression of interleukin 12 p35 transcription in murine bone marrow-derived dendritic cells,” Journal of General Virology, vol. 86, pp. 1885-1890 (2005).

Pattnaik et al. “Fusogenic peptide as diagnostic marker for detection of flaviviruses,” J Postgrad Med, vol. 52, No. 3, pp. 174-178 (2006).

Gall, A. GenBank: CAP59541.1; published in Aug. 2008.

(56) References Cited

OTHER PUBLICATIONS

Elsevier, “Rapid Reference to Influenza”, http://web.archive.org/web/20150921044636/http://www.rapidreferenceinfluenza.com:80/resource-center, retrieved Sep. 21, 2015.
Campos et al. N0BJ26_9FLAV.pdf; 2013.
Fass D., Kim PS. “Dissection of a retrovirus envelope protein reveals structural similarity to influenza hemagglutinin”. Current Biology 1995, 5:1377-1383.
Denner J, et al., “The immunosuppressive peptide of HIV-1: functional domains and immune response in AIDS patients”, AIDS, vol. 8, 1994, pp. 1063-1072.
Haraguchi S, et al., “Induction of intracellular cAMP by a synthetic retroviral envelope peptide: a possible mechanism of immunopathogenesis in retroviral infections”, Proceedings of the National Academy of Sciences of the United States of America, vol. 92, No. 12, Jun. 6, 1995, pp. 5568-5571.
Haraguchi S., et al., “A potent immunosuppressive retroviral peptide: cytokine patterns and signaling pathways”, Immunol. Res., vol. 41, No. 1, May 1, 2008, pp. 46-55.
Sander, H.M., et al., “The annual cost of psoriasis”, J. Am. Acad. Dermatol., vol. 28, 1993, pp. 422-425.
Funding, A.T., et al., “Reduced oxazolone-induced skin inflammation in MAPKAP kinase 2 knockout mice”, J. Invest. Dermatol., vol. 129, 2009, pp. 891-898.
Kim, S.D., et al., “The agonists of formyl peptide receptors prevent development of severe sepsis after microbial infection”, J. Immunol., vol. 185, 2010, pp. 4302-4310.
Hillenbrand, A, et al., “Sepsis induced changes of adipokines and cytokines—septic patients compared to morbidly obese patients”, BMC Surgery, vol. 10, No. 26, 2010, 9 pages.
Hamishefikar, H., et al., “Identification of enhanced cytokine generation following sepsis. Dream of magic bullet for mortality prediction and therapeutic evaluation”, DARU, Vo. 18, No. 3, 2010, ppl 155-162.
Delavallèe, L, et al., “Anti-cytokine vaccination in autoimmune diseases”, Swiss Med Wkly., vol. 140:w13108; 2010, 6 pgs.
Finkelman, F.D., et al., “Importance of cytokines in murine allergic airway disease and human asthma”, J Immunol., vol. 184, 2010, pp. 1663-1674.
Corren, J., “Cytokine inhibition in severe asthma: current knowledge and future directions”, Current Opinion in Pulmonary Medicine, vol. 17, 2011, pp. 29-33.
De Paz, B, et al., “Cytokines and regulatory T cells in rheumatoid arthritis and their relationship with response to corticosteroids”, The Journal of Rheumatology, vol. 37, No. 12, 2010, pp. 2502-2510.
Agarwal, V. and Malaviya, A.N., “Cytokine network and its manipulation in rheumatoid arthritis”, J. Indian Rheumatol. Assoc., vol. 13, 2005, pp. 86-91.
Broos, S. et al., “Immunomodulatory nanoparticles as adjuvants and allergen-delivery system to human dendritic cells: Implications for specific immunotherapy”, Vaccine, vol. 28, 2010, pp. 5075-5085.
Morimoto, Y., et al., “Expression of inflammation-related cytokines following intratracheal instillation of nickel oxide nanoparticles”, Nanotoxicology, vol. 4, No. 2, Jun. 2010, pp. 161-176.
Summer, B., et al., “Nickel (Ni) allergic patients with complications to Ni containing joint replacement show preferential IL-17 type reactivity to Ni”, Contact Dermatitis, vol. 63, 2010, pp. 15-22.
Schutte, R.J., et al., “In vivo cytokine-associated responses to biomaterials”, Biomaterials, vol. 30, 2009, ppl. 160-168.
Rodriguez A. et al., “Quantitative in vivo cytokine analysis at synthetic biomaterial implant sites”, Journal of Biomedical Materials Research Part A, Apr. 2009; 89(1).
Roberts-Thomson, I.C., et al., “Cells, cytokines and inflammatory bowel disease: a clinical perspective”, Expert Review of Gastroenterology and Hepatology, vol. 5, No. 6, Dec. 2011, pp. 703-716.
Rogler, G. and Andus, T., “Cytokines in inflammatory bowel disease”, World Journal of Surgery, vol. 22, 1998, pp. 382-389.
Chanput, W., et al., “Transcriptional profiles of LPS-stimulated THP-1 monocytes and macrophages: a tool to study inflammation modulating effects of food-derived compounds”, Food & Function, vol. 1, 2010, pp. 254-261.
Cross, KJ. et al., “Composition and Functions of the Influenza Fusion Peptide” Protein & Peptide Letters, 2009, 16, 766-778.
Holvast, B. et al., “Influenza vaccination in systemic lupus erypthematosus: Safe and protective?” Autoimmunity Reviews 6(2007) pp. 300-305.
Julkunen, I. et al., “Inflammatory responses in influenza A virus infection” Vaccine 19 (2001) pp. 32-37.
Lambart LC. et al., “Influenza Vaccines for the Future”, The New England Journal of Medicine 2010; 363, pp. 2036-2044.
Stojanovich, L. et al., “Stress as a trigger of autoimmune disease”, Autoimmunity reviews 7, 2008, pp. 209-213.

* cited by examiner

SEQUENCE LISTING

<160> NUMBER OF SEQ ID NOS: 218

<210> SEQ ID NO 1
<211> LENGTH: 27
<212> TYPE: PRT
<213> ORGANISM: Unknown
<220> FEATURE:
<223> OTHER INFORMATION: Viral immunosuppression sequence

<400> SEQUENCE: 1

```
Val Gln Val Thr Pro His His Val Leu Val Asp Glu Tyr Thr Gly Glu
1               5                   10                  15

Trp Val Asp Ser Gln Phe Ile Asn Gly Lys Cys
            20                  25
```

<210> SEQ ID NO 2
<211> LENGTH: 14
<212> TYPE: PRT
<213> ORGANISM: Unknown
<220> FEATURE:
<223> OTHER INFORMATION: Viral immunosuppression sequence

<400> SEQUENCE: 2

```
Asp Arg Gly Trp Gly Asn Gly Cys Gly Leu Phe Gly Lys Gly
1               5                   10
```

<210> SEQ ID NO 3
<211> LENGTH: 17
<212> TYPE: PRT
<213> ORGANISM: Unknown
<220> FEATURE:
<223> OTHER INFORMATION: Viral immunosuppression sequence

<400> SEQUENCE: 3

```
Gly Leu Ile His Leu His Gln Asn Ile Val Asp Val Gln Tyr Leu Tyr
1               5                   10                  15

Gly
```

<210> SEQ ID NO 4
<211> LENGTH: 16
<212> TYPE: PRT
<213> ORGANISM: Unknown
<220> FEATURE:
<223> OTHER INFORMATION: Viral immunosuppression sequence

<400> SEQUENCE: 4

```
Gly Leu Phe Gly Ala Ile Ala Gly Phe Ile Glu Asn Gly Trp Glu Gly
1               5                   10                  15
```

<210> SEQ ID NO 5
<211> LENGTH: 22
<212> TYPE: PRT
<213> ORGANISM: Unknown
<220> FEATURE:
<223> OTHER INFORMATION: Viral immunosuppression sequence

<400> SEQUENCE: 5

```
Gly Phe Thr Cys Thr Gly Val Val Thr Glu Ala Glu Thr Tyr Thr Asn
1               5                   10                  15

Phe Val Gly Tyr Val Thr
            20
```

<210> SEQ ID NO 6
<211> LENGTH: 18
<212> TYPE: PRT

<213> ORGANISM: Unknown
<220> FEATURE:
<223> OTHER INFORMATION: Viral immunosuppression sequence

<400> SEQUENCE: 6

Ser Leu His Asn Pro Tyr Pro Asp Tyr Arg Trp Leu Arg Thr Val Lys
1 5 10 15

Thr Thr

<210> SEQ ID NO 7
<211> LENGTH: 19
<212> TYPE: PRT
<213> ORGANISM: Unknown
<220> FEATURE:
<223> OTHER INFORMATION: Viral immunosuppression sequence

<400> SEQUENCE: 7

Gly Asp Ala Ala Trp Asp Phe Gly Ser Val Gly Gly Val Phe Asn Ser
1 5 10 15

Leu Gly Lys

<210> SEQ ID NO 8
<211> LENGTH: 19
<212> TYPE: PRT
<213> ORGANISM: Unknown
<220> FEATURE:
<223> OTHER INFORMATION: Viral immunosuppression sequence

<400> SEQUENCE: 8

Gly Gly Thr Ala Trp Asp Phe Gly Ser Ile Gly Gly Val Phe Thr Ser
1 5 10 15

Val Gly Lys

<210> SEQ ID NO 9
<211> LENGTH: 19
<212> TYPE: PRT
<213> ORGANISM: Unknown
<220> FEATURE:
<223> OTHER INFORMATION: Viral immunosuppression sequence

<400> SEQUENCE: 9

Gly Asp Thr Ala Trp Asp Phe Gly Ser Leu Gly Gly Val Phe Thr Ser
1 5 10 15

Val Gly Lys

<210> SEQ ID NO 10
<211> LENGTH: 19
<212> TYPE: PRT
<213> ORGANISM: Unknown
<220> FEATURE:
<223> OTHER INFORMATION: Viral immunosuppression sequence

<400> SEQUENCE: 10

Gly Glu Thr Ala Trp Asp Phe Gly Ser Val Gly Gly Leu Leu Thr Ser
1 5 10 15

Leu Gly Lys

<210> SEQ ID NO 11
<211> LENGTH: 19
<212> TYPE: PRT
<213> ORGANISM: Unknown
<220> FEATURE:
<223> OTHER INFORMATION: Viral immunosuppression sequence

<400> SEQUENCE: 11

Leu Gly Asp Thr Ala Trp Asp Phe Gly Ser Ile Gly Gly Val Phe Asn
1               5                   10                  15

Ser Ile Gly

<210> SEQ ID NO 12
<211> LENGTH: 19
<212> TYPE: PRT
<213> ORGANISM: Unknown
<220> FEATURE:
<223> OTHER INFORMATION: Viral immunosuppression sequence

<400> SEQUENCE: 12

Leu Gly Asp Thr Ala Trp Asp Phe Gly Ser Val Gly Gly Ile Phe Thr
1               5                   10                  15

Ser Leu Gly

<210> SEQ ID NO 13
<211> LENGTH: 19
<212> TYPE: PRT
<213> ORGANISM: Unknown
<220> FEATURE:
<223> OTHER INFORMATION: Viral immunosuppression sequence

<400> SEQUENCE: 13

Leu Gly Asp Thr Ala Trp Asp Phe Gly Ser Val Gly Gly Val Phe Asn
1               5                   10                  15

Ser Ile Gly

<210> SEQ ID NO 14
<211> LENGTH: 19
<212> TYPE: PRT
<213> ORGANISM: Unknown
<220> FEATURE:
<223> OTHER INFORMATION: Viral immunosuppression sequence

<400> SEQUENCE: 14

Leu Gly Asp Thr Ala Trp Asp Phe Gly Ser Val Gly Gly Ile Phe Asn
1               5                   10                  15

Ser Val Gly

<210> SEQ ID NO 15
<211> LENGTH: 19
<212> TYPE: PRT
<213> ORGANISM: Unknown
<220> FEATURE:
<223> OTHER INFORMATION: Viral immunosuppression sequence

<400> SEQUENCE: 15

Leu Gly Asp Thr Ala Trp Asp Phe Gly Ser Val Gly Gly Val Phe Thr
1               5                   10                  15

Ser Val Gly

<210> SEQ ID NO 16
<211> LENGTH: 19
<212> TYPE: PRT
<213> ORGANISM: Unknown
<220> FEATURE:
<223> OTHER INFORMATION: Viral immunosuppression sequence

<400> SEQUENCE: 16

Ile Gly Asp Asp Ala Trp Asp Phe Gly Ser Val Gly Gly Ile Leu Asn
1               5                   10                  15

Ser Val Gly

<210> SEQ ID NO 17
<211> LENGTH: 19
<212> TYPE: PRT
<213> ORGANISM: Unknown
<220> FEATURE:
<223> OTHER INFORMATION: Viral immunosuppression sequence

<400> SEQUENCE: 17

Val Gly Ser Ala Phe Trp Asn Ser Asp Gln Arg Phe Ser Ala Ile Asn
1 5 10 15

Leu Met Asp

<210> SEQ ID NO 18
<211> LENGTH: 14
<212> TYPE: PRT
<213> ORGANISM: Unknown
<220> FEATURE:
<223> OTHER INFORMATION: Viral immunosuppression sequence

<400> SEQUENCE: 18

Asp Arg Gly Trp Gly Asn Gly Cys Ala Leu Phe Gly Lys Gly
1 5 10

<210> SEQ ID NO 19
<211> LENGTH: 19
<212> TYPE: PRT
<213> ORGANISM: Unknown
<220> FEATURE:
<223> OTHER INFORMATION: Viral immunosuppression sequence

<400> SEQUENCE: 19

Thr Gly Glu His Ser Trp Asp Phe Gly Ser Thr Gly Gly Phe Phe Ala
1 5 10 15

Ser Val Gly

<210> SEQ ID NO 20
<211> LENGTH: 19
<212> TYPE: PRT
<213> ORGANISM: Unknown
<220> FEATURE:
<223> OTHER INFORMATION: Viral immunosuppression sequence

<400> SEQUENCE: 20

Leu Gly Asp Thr Ala Trp Asp Phe Gly Ser Val Gly Gly Phe Phe Thr
1 5 10 15

Ser Leu Gly

<210> SEQ ID NO 21
<211> LENGTH: 19
<212> TYPE: PRT
<213> ORGANISM: Unknown
<220> FEATURE:
<223> OTHER INFORMATION: Viral immunosuppression sequence

<400> SEQUENCE: 21

Ile Gly Asp Asp Ala Trp Asp Phe Gly Ser Thr Gly Gly Ile Phe Asn
1 5 10 15

Thr Ile Gly

<210> SEQ ID NO 22
<211> LENGTH: 20

```
<212> TYPE: PRT
<213> ORGANISM: Unknown
<220> FEATURE:
<223> OTHER INFORMATION: Viral immunosuppression sequence

<400> SEQUENCE: 22

Ser Ser Ala Phe Trp Asn Ser Asp Glu Pro Phe His Phe Ser Asn Leu
1               5                   10                  15

Ile Ser Ile Ile
            20


<210> SEQ ID NO 23
<211> LENGTH: 20
<212> TYPE: PRT
<213> ORGANISM: Unknown
<220> FEATURE:
<223> OTHER INFORMATION: Viral immunosuppression sequence

<400> SEQUENCE: 23

Gly Asp Asp Ala Trp Asp Phe Gly Ser Thr Gly Gly Ile Phe Asn Thr
1               5                   10                  15

Ile Gly Lys Ala
            20


<210> SEQ ID NO 24
<211> LENGTH: 20
<212> TYPE: PRT
<213> ORGANISM: Unknown
<220> FEATURE:
<223> OTHER INFORMATION: Viral immunosuppression sequence

<400> SEQUENCE: 24

Ser Ser Ala Tyr Trp Ser Ser Ser Glu Pro Phe Thr Ser Ala Gly Ile
1               5                   10                  15

Met Arg Ile Leu
            20


<210> SEQ ID NO 25
<211> LENGTH: 20
<212> TYPE: PRT
<213> ORGANISM: Unknown
<220> FEATURE:
<223> OTHER INFORMATION: Viral immunosuppression sequence

<400> SEQUENCE: 25

Gly Ser Ser Ser Trp Asp Phe Ser Ser Ala Gly Gly Phe Phe Gly Ser
1               5                   10                  15

Ile Gly Lys Ala
            20


<210> SEQ ID NO 26
<211> LENGTH: 20
<212> TYPE: PRT
<213> ORGANISM: Unknown
<220> FEATURE:
<223> OTHER INFORMATION: Viral immunosuppression sequence

<400> SEQUENCE: 26

Gly Asp Ala Ala Trp Asp Phe Gly Ser Val Gly Gly Phe Met Thr Ser
1               5                   10                  15

Ile Gly Arg Ala
            20


<210> SEQ ID NO 27
```

<211> LENGTH: 14
<212> TYPE: PRT
<213> ORGANISM: Unknown
<220> FEATURE:
<223> OTHER INFORMATION: Viral immunosuppression sequence

<400> SEQUENCE: 27

Asp Arg Gly Trp Gly Asn His Cys Gly Leu Phe Gly Lys Gly
1 5 10

<210> SEQ ID NO 28
<211> LENGTH: 20
<212> TYPE: PRT
<213> ORGANISM: Unknown
<220> FEATURE:
<223> OTHER INFORMATION: Viral immunosuppression sequence

<400> SEQUENCE: 28

Gly Glu Thr Ala Trp Asp Phe Gly Ser Ala Gly Gly Phe Phe Thr Ser
1 5 10 15

Val Gly Arg Gly
20

<210> SEQ ID NO 29
<211> LENGTH: 20
<212> TYPE: PRT
<213> ORGANISM: Unknown
<220> FEATURE:
<223> OTHER INFORMATION: Viral immunosuppression sequence

<400> SEQUENCE: 29

Gly Glu Ala Ala Trp Asp Phe Gly Ser Ala Gly Gly Phe Phe Gln Ser
1 5 10 15

Val Gly Arg Gly
20

<210> SEQ ID NO 30
<211> LENGTH: 20
<212> TYPE: PRT
<213> ORGANISM: Unknown
<220> FEATURE:
<223> OTHER INFORMATION: Viral immunosuppression sequence

<400> SEQUENCE: 30

Leu Gly Asp Thr Ala Trp Asp Phe Gly Ser Val Gly Gly Val Phe Asn
1 5 10 15

Ser Leu Gly Lys
20

<210> SEQ ID NO 31
<211> LENGTH: 19
<212> TYPE: PRT
<213> ORGANISM: Unknown
<220> FEATURE:
<223> OTHER INFORMATION: Viral immunosuppression sequence

<400> SEQUENCE: 31

Val Gly Glu His Ala Trp Asp Phe Gly Ser Val Gly Gly Met Leu Ser
1 5 10 15

Ser Val Gly

<210> SEQ ID NO 32
<211> LENGTH: 20
<212> TYPE: PRT
<213> ORGANISM: Unknown

<220> FEATURE:
<223> OTHER INFORMATION: Viral immunosuppression sequence

<400> SEQUENCE: 32

Val Leu Gly Glu His Ala Trp Asp Phe Gly Ser Val Gly Gly Val Met
1 5 10 15

Thr Ser Ile Gly
20

<210> SEQ ID NO 33
<211> LENGTH: 19
<212> TYPE: PRT
<213> ORGANISM: Unknown
<220> FEATURE:
<223> OTHER INFORMATION: Viral immunosuppression sequence

<400> SEQUENCE: 33

Ile Gly Glu His Ala Trp Asp Phe Gly Ser Ala Gly Gly Phe Phe Ser
1 5 10 15

Ser Ile Gly

<210> SEQ ID NO 34
<211> LENGTH: 19
<212> TYPE: PRT
<213> ORGANISM: Unknown
<220> FEATURE:
<223> OTHER INFORMATION: Viral immunosuppression sequence

<400> SEQUENCE: 34

Leu Gly Glu His Ala Trp Asp Phe Gly Ser Thr Gly Gly Phe Leu Ser
1 5 10 15

Ser Ile Gly

<210> SEQ ID NO 35
<211> LENGTH: 19
<212> TYPE: PRT
<213> ORGANISM: Unknown
<220> FEATURE:
<223> OTHER INFORMATION: Viral immunosuppression sequence

<400> SEQUENCE: 35

Val Gly Glu His Ala Trp Asp Phe Gly Ser Val Gly Gly Ile Leu Ser
1 5 10 15

Ser Val Gly

<210> SEQ ID NO 36
<211> LENGTH: 14
<212> TYPE: PRT
<213> ORGANISM: Unknown
<220> FEATURE:
<223> OTHER INFORMATION: Viral immunosuppression sequence

<400> SEQUENCE: 36

Asp Arg Gly Trp Gly Asn His Cys Gly Phe Phe Gly Lys Gly
1 5 10

<210> SEQ ID NO 37
<211> LENGTH: 19
<212> TYPE: PRT
<213> ORGANISM: Unknown
<220> FEATURE:
<223> OTHER INFORMATION: Viral immunosuppression sequence

<400> SEQUENCE: 37

Ile Gly Glu His Ala Trp Asp Phe Gly Ser Ala Gly Gly Phe Leu Ser
1 5 10 15

Ser Ile Gly

<210> SEQ ID NO 38
<211> LENGTH: 19
<212> TYPE: PRT
<213> ORGANISM: Unknown
<220> FEATURE:
<223> OTHER INFORMATION: Viral immunosuppression sequence

<400> SEQUENCE: 38

Ile Gly Glu His Ala Trp Asp Phe Gly Ser Thr Gly Gly Phe Leu Thr
1 5 10 15

Ser Val Gly

<210> SEQ ID NO 39
<211> LENGTH: 19
<212> TYPE: PRT
<213> ORGANISM: Unknown
<220> FEATURE:
<223> OTHER INFORMATION: Viral immunosuppression sequence

<400> SEQUENCE: 39

Ile Gly Glu His Ala Trp Asp Phe Gly Ser Thr Gly Gly Phe Leu Ala
1 5 10 15

Ser Val Gly

<210> SEQ ID NO 40
<211> LENGTH: 19
<212> TYPE: PRT
<213> ORGANISM: Unknown
<220> FEATURE:
<223> OTHER INFORMATION: Viral immunosuppression sequence

<400> SEQUENCE: 40

Leu Gly Asp Thr Ala Trp Asp Phe Gly Ser Ile Gly Gly Val Phe Thr
1 5 10 15

Ser Leu Gly

<210> SEQ ID NO 41
<211> LENGTH: 19
<212> TYPE: PRT
<213> ORGANISM: Unknown
<220> FEATURE:
<223> OTHER INFORMATION: Viral immunosuppression sequence

<400> SEQUENCE: 41

Val Gly Ser Ser Ser Trp Asp Phe Ser Ser Thr Ser Gly Phe Phe Ser
1 5 10 15

Ser Val Gly

<210> SEQ ID NO 42
<211> LENGTH: 19
<212> TYPE: PRT
<213> ORGANISM: Unknown
<220> FEATURE:
<223> OTHER INFORMATION: Viral immunosuppression sequence

<400> SEQUENCE: 42

Val Gly Arg Ser Ser Trp Asp Phe Ser Ser Ala Gly Gly Phe Phe Ser
1 5 10 15

Ser Val Gly

<210> SEQ ID NO 43
<211> LENGTH: 19
<212> TYPE: PRT
<213> ORGANISM: Unknown
<220> FEATURE:
<223> OTHER INFORMATION: Viral immunosuppression sequence

<400> SEQUENCE: 43

Met Gly Asp Thr Ala Trp Asp Phe Ser Ser Ala Gly Gly Phe Phe Thr
1               5                   10                  15

Ser Val Gly

<210> SEQ ID NO 44
<211> LENGTH: 14
<212> TYPE: PRT
<213> ORGANISM: Unknown
<220> FEATURE:
<223> OTHER INFORMATION: Viral immunosuppression sequence

<400> SEQUENCE: 44

Asn Arg Gly Trp Gly Thr Gly Cys Phe Lys Trp Gly Ile Gly
1               5                   10

<210> SEQ ID NO 45
<211> LENGTH: 14
<212> TYPE: PRT
<213> ORGANISM: Unknown
<220> FEATURE:
<223> OTHER INFORMATION: Viral immunosuppression sequence

<400> SEQUENCE: 45

Asn Arg Gly Trp Gly Thr Gly Cys Phe Glu Trp Gly Leu Gly
1               5                   10

<210> SEQ ID NO 46
<211> LENGTH: 23
<212> TYPE: PRT
<213> ORGANISM: Unknown
<220> FEATURE:
<223> OTHER INFORMATION: Viral immunosuppression sequence

<400> SEQUENCE: 46

His Val Ala Gly Arg Tyr Ser Lys His Gly Met Ala Gly Ile Gly Ser
1               5                   10                  15

Val Trp Glu Asp Leu Val Arg
            20

<210> SEQ ID NO 47
<211> LENGTH: 14
<212> TYPE: PRT
<213> ORGANISM: Unknown
<220> FEATURE:
<223> OTHER INFORMATION: Viral immunosuppression sequence

<400> SEQUENCE: 47

Val Asp Lys Tyr Arg Arg Phe Gly Thr Ala Gly Val Gly Gly
1               5                   10

<210> SEQ ID NO 48
<211> LENGTH: 17
<212> TYPE: PRT
<213> ORGANISM: Unknown
<220> FEATURE:
<223> OTHER INFORMATION: Viral immunosuppression sequence

<400> SEQUENCE: 48

Gly Leu Ile His Leu His Arg Asn Ile Val Asp Val Gln Tyr Leu Tyr
1               5                   10                  15

Gly

<210> SEQ ID NO 49
<211> LENGTH: 17
<212> TYPE: PRT
<213> ORGANISM: Unknown
<220> FEATURE:
<223> OTHER INFORMATION: Viral immunosuppression sequence

<400> SEQUENCE: 49

Gly Leu Ile His Leu His Gln Asn Ile Val Asp Val Gln Tyr Met Tyr
1               5                   10                  15

Gly

<210> SEQ ID NO 50
<211> LENGTH: 17
<212> TYPE: PRT
<213> ORGANISM: Unknown
<220> FEATURE:
<223> OTHER INFORMATION: Viral immunosuppression sequence

<400> SEQUENCE: 50

Gly Leu Ile His Leu His Gln Asn Ile Val Asp Thr Gln Tyr Leu Tyr
1               5                   10                  15

Gly

<210> SEQ ID NO 51
<211> LENGTH: 24
<212> TYPE: PRT
<213> ORGANISM: Unknown
<220> FEATURE:
<223> OTHER INFORMATION: Viral immunosuppression sequence

<400> SEQUENCE: 51

Asn Thr Thr Leu Leu Asn Gly Ser Ala Phe Gln Leu Ile Cys Pro Tyr
1               5                   10                  15

Gly Trp Val Gly Arg Val Glu Cys
            20

<210> SEQ ID NO 52
<211> LENGTH: 19
<212> TYPE: PRT
<213> ORGANISM: Unknown
<220> FEATURE:
<223> OTHER INFORMATION: Viral immunosuppression sequence

<400> SEQUENCE: 52

Ser Tyr Phe Gln Gln Tyr Met Leu Lys Gly Gln Tyr Gln Tyr Trp Phe
1               5                   10                  15

Asp Leu Glu

<210> SEQ ID NO 53
<211> LENGTH: 24
<212> TYPE: PRT
<213> ORGANISM: Unknown
<220> FEATURE:
<223> OTHER INFORMATION: Viral immunosuppression sequence

<400> SEQUENCE: 53

Asn Thr Thr Leu Leu Asn Gly Pro Ala Phe Gln Met Val Cys Pro Leu

```
1               5                   10                  15

Gly Trp Thr Gly Thr Val Ser Cys
            20


<210> SEQ ID NO 54
<211> LENGTH: 19
<212> TYPE: PRT
<213> ORGANISM: Unknown
<220> FEATURE:
<223> OTHER INFORMATION: Viral immunosuppression sequence

<400> SEQUENCE: 54

Ser Tyr Phe Gln Gln Tyr Met Leu Lys Gly Glu Tyr Gln Tyr Trp Phe
1               5                   10                  15

Asp Leu Glu


<210> SEQ ID NO 55
<211> LENGTH: 22
<212> TYPE: PRT
<213> ORGANISM: Unknown
<220> FEATURE:
<223> OTHER INFORMATION: Viral immunosuppression sequence

<400> SEQUENCE: 55

Ser Leu Leu Asn Gly Pro Ala Phe Gln Met Val Cys Pro Gln Gly Trp
1               5                   10                  15

Thr Gly Thr Ile Glu Cys
            20


<210> SEQ ID NO 56
<211> LENGTH: 20
<212> TYPE: PRT
<213> ORGANISM: Unknown
<220> FEATURE:
<223> OTHER INFORMATION: Viral immunosuppression sequence

<400> SEQUENCE: 56

Asp Arg Tyr Phe Gln Gln Tyr Met Leu Lys Gly Lys Trp Gln Tyr Trp
1               5                   10                  15

Phe Asp Leu Asp
            20


<210> SEQ ID NO 57
<211> LENGTH: 22
<212> TYPE: PRT
<213> ORGANISM: Unknown
<220> FEATURE:
<223> OTHER INFORMATION: Viral immunosuppression sequence

<400> SEQUENCE: 57

Thr Leu Leu Asn Gly Ser Ala Phe Tyr Leu Val Cys Pro Ile Gly Trp
1               5                   10                  15

Thr Gly Val Ile Glu Cys
            20


<210> SEQ ID NO 58
<211> LENGTH: 19
<212> TYPE: PRT
<213> ORGANISM: Unknown
<220> FEATURE:
<223> OTHER INFORMATION: Viral immunosuppression sequence

<400> SEQUENCE: 58

Ser Tyr Phe Gln Gln Tyr Met Leu Lys Gly Glu Tyr Gln Tyr Trp Phe
```

1 5 10 15

Asp Leu Asp

<210> SEQ ID NO 59
<211> LENGTH: 22
<212> TYPE: PRT
<213> ORGANISM: Unknown
<220> FEATURE:
<223> OTHER INFORMATION: Viral immunosuppression sequence

<400> SEQUENCE: 59

Thr Leu Leu Asn Gly Pro Ala Phe Gln Leu Val Cys Pro Tyr Gly Trp
1 5 10 15

Thr Gly Thr Ile Glu Cys
20

<210> SEQ ID NO 60
<211> LENGTH: 23
<212> TYPE: PRT
<213> ORGANISM: Unknown
<220> FEATURE:
<223> OTHER INFORMATION: Viral immunosuppression sequence

<400> SEQUENCE: 60

Asp Asn Tyr Phe Gln Gln Tyr Met Leu Lys Gly Lys Tyr Gln Tyr Trp
1 5 10 15

Phe Asp Leu Glu Ala Thr Asp
20

<210> SEQ ID NO 61
<211> LENGTH: 22
<212> TYPE: PRT
<213> ORGANISM: Unknown
<220> FEATURE:
<223> OTHER INFORMATION: Viral immunosuppression sequence

<400> SEQUENCE: 61

Thr Leu Leu Asn Gly Ser Ala Phe Gln Met Val Cys Pro Phe Gly Trp
1 5 10 15

Thr Gly Gln Val Glu Cys
20

<210> SEQ ID NO 62
<211> LENGTH: 23
<212> TYPE: PRT
<213> ORGANISM: Unknown
<220> FEATURE:
<223> OTHER INFORMATION: Viral immunosuppression sequence

<400> SEQUENCE: 62

Asp Ser Tyr Phe Gln Gln Tyr Met Leu Lys Gly Glu Tyr Gln Tyr Trp
1 5 10 15

Phe Asp Leu Asp Ala Lys Asp
20

<210> SEQ ID NO 63
<211> LENGTH: 22
<212> TYPE: PRT
<213> ORGANISM: Unknown
<220> FEATURE:
<223> OTHER INFORMATION: Viral immunosuppression sequence

<400> SEQUENCE: 63

Gly Val Tyr Pro Phe Met Trp Gly Gly Ala Tyr Cys Phe Cys Asp Thr

```
1               5                   10                  15

Glu Asn Thr Gln Val Ser
            20


<210> SEQ ID NO 64
<211> LENGTH: 23
<212> TYPE: PRT
<213> ORGANISM: Unknown
<220> FEATURE:
<223> OTHER INFORMATION: Viral immunosuppression sequence

<400> SEQUENCE: 64

Ala Pro Phe Gly Cys Glu Ile Tyr Thr Asn Pro Ile Arg Ala Glu Asn
1               5                   10                  15

Cys Ala Val Gly Ser Ile Pro
            20


<210> SEQ ID NO 65
<211> LENGTH: 22
<212> TYPE: PRT
<213> ORGANISM: Unknown
<220> FEATURE:
<223> OTHER INFORMATION: Viral immunosuppression sequence

<400> SEQUENCE: 65

Ser Asp Phe Gly Gly Ile Ala Thr Val Lys Tyr Ser Ala Ser Lys Ser
1               5                   10                  15

Gly Lys Cys Ala Val His
            20


<210> SEQ ID NO 66
<211> LENGTH: 28
<212> TYPE: PRT
<213> ORGANISM: Unknown
<220> FEATURE:
<223> OTHER INFORMATION: Viral immunosuppression sequence

<400> SEQUENCE: 66

Phe Ser Thr Ala Asn Ile His Pro Glu Phe Arg Leu Gln Ile Cys Thr
1               5                   10                  15

Ser Tyr Val Thr Cys Lys Gly Asp Cys His Pro Pro
            20                  25


<210> SEQ ID NO 67
<211> LENGTH: 15
<212> TYPE: PRT
<213> ORGANISM: Unknown
<220> FEATURE:
<223> OTHER INFORMATION: Viral immunosuppression sequence

<400> SEQUENCE: 67

Gly Val Tyr Pro Phe Met Trp Gly Gly Ala Tyr Cys Phe Cys Asp
1               5                   10                  15


<210> SEQ ID NO 68
<211> LENGTH: 19
<212> TYPE: PRT
<213> ORGANISM: Unknown
<220> FEATURE:
<223> OTHER INFORMATION: Viral immunosuppression sequence

<400> SEQUENCE: 68

Gly Asp Cys His Pro Pro Lys Asp His Ile Val Thr His Pro Gln Tyr
1               5                   10                  15
```

His Ala Gln

<210> SEQ ID NO 69
<211> LENGTH: 12
<212> TYPE: PRT
<213> ORGANISM: Unknown
<220> FEATURE:
<223> OTHER INFORMATION: Viral immunosuppression sequence

<400> SEQUENCE: 69

Ala Val Ser Lys Thr Ala Trp Thr Trp Leu Thr Ser
1 5 10

<210> SEQ ID NO 70
<211> LENGTH: 17
<212> TYPE: PRT
<213> ORGANISM: Unknown
<220> FEATURE:
<223> OTHER INFORMATION: Viral immunosuppression sequence

<400> SEQUENCE: 70

Val His Cys Ala Ala Glu Cys His Pro Pro Lys Asp His Ile Val Asn
1 5 10 15

Tyr

<210> SEQ ID NO 71
<211> LENGTH: 20
<212> TYPE: PRT
<213> ORGANISM: Unknown
<220> FEATURE:
<223> OTHER INFORMATION: Viral immunosuppression sequence

<400> SEQUENCE: 71

Pro Ala Ser His Thr Thr Leu Gly Val Gln Asp Ile Ser Ala Thr Ala
1 5 10 15

Met Ser Trp Val
20

<210> SEQ ID NO 72
<211> LENGTH: 30
<212> TYPE: PRT
<213> ORGANISM: Unknown
<220> FEATURE:
<223> OTHER INFORMATION: Viral immunosuppression sequence

<400> SEQUENCE: 72

Ala Cys Thr Phe Trp Ala Val Asn Ala Tyr Ser Ser Gly Gly Tyr Ala
1 5 10 15

Gln Leu Ala Ser Tyr Phe Asn Pro Gly Gly Ser Tyr Tyr Lys
20 25 30

<210> SEQ ID NO 73
<211> LENGTH: 27
<212> TYPE: PRT
<213> ORGANISM: Unknown
<220> FEATURE:
<223> OTHER INFORMATION: Viral immunosuppression sequence

<400> SEQUENCE: 73

Gln Tyr His Pro Thr Ala Cys Glu Val Glu Pro Ala Phe Gly His Ser
1 5 10 15

Asp Ala Ala Cys Trp Gly Phe Pro Thr Asp Thr
20 25

<210> SEQ ID NO 74
<211> LENGTH: 23
<212> TYPE: PRT
<213> ORGANISM: Unknown
<220> FEATURE:
<223> OTHER INFORMATION: Viral immunosuppression sequence

<400> SEQUENCE: 74

Met Ser Val Phe Ala Leu Ala Ser Tyr Val Gln His Pro His Lys Thr
1 5 10 15

Val Arg Val Lys Phe His Thr
20

<210> SEQ ID NO 75
<211> LENGTH: 14
<212> TYPE: PRT
<213> ORGANISM: Unknown
<220> FEATURE:
<223> OTHER INFORMATION: Viral immunosuppression sequence

<400> SEQUENCE: 75

Glu Thr Arg Thr Val Trp Gln Ser Val Ala Gly Val Ser Cys
1 5 10

<210> SEQ ID NO 76
<211> LENGTH: 22
<212> TYPE: PRT
<213> ORGANISM: Unknown
<220> FEATURE:
<223> OTHER INFORMATION: Viral immunosuppression sequence

<400> SEQUENCE: 76

Asn Val Thr Thr Glu His Pro Phe Cys Asn Met Pro His Gly Gln Leu
1 5 10 15

Glu Val Gln Val Pro Pro
20

<210> SEQ ID NO 77
<211> LENGTH: 20
<212> TYPE: PRT
<213> ORGANISM: Unknown
<220> FEATURE:
<223> OTHER INFORMATION: Viral immunosuppression sequence

<400> SEQUENCE: 77

Asp Pro Gly Asp Leu Val Glu Tyr Ile Met Asn Tyr Thr Gly Asn Gln
1 5 10 15

Gln Ser Arg Trp
20

<210> SEQ ID NO 78
<211> LENGTH: 23
<212> TYPE: PRT
<213> ORGANISM: Unknown
<220> FEATURE:
<223> OTHER INFORMATION: Viral immunosuppression sequence

<400> SEQUENCE: 78

Gly Ser Pro Asn Cys His Gly Pro Asp Trp Ala Ser Pro Val Cys Gln
1 5 10 15

Arg His Ser Pro Asp Cys Ser
20

<210> SEQ ID NO 79
<211> LENGTH: 15

```
<212> TYPE: PRT
<213> ORGANISM: Unknown
<220> FEATURE:
<223> OTHER INFORMATION: Viral immunosuppression sequence

<400> SEQUENCE: 79

Arg Leu Val Gly Ala Thr Pro Glu Arg Pro Arg Leu Arg Leu Val
1               5                   10                  15


<210> SEQ ID NO 80
<211> LENGTH: 13
<212> TYPE: PRT
<213> ORGANISM: Unknown
<220> FEATURE:
<223> OTHER INFORMATION: Viral immunosuppression sequence

<400> SEQUENCE: 80

Asp Ala Asp Asp Pro Leu Leu Arg Thr Ala Pro Gly Pro
1               5                   10


<210> SEQ ID NO 81
<211> LENGTH: 18
<212> TYPE: PRT
<213> ORGANISM: Unknown
<220> FEATURE:
<223> OTHER INFORMATION: Viral immunosuppression sequence

<400> SEQUENCE: 81

Gly Glu Val Trp Val Thr Pro Val Ile Gly Ser Gln Ala Arg Lys Cys
1               5                   10                  15

Gly Leu


<210> SEQ ID NO 82
<211> LENGTH: 22
<212> TYPE: PRT
<213> ORGANISM: Unknown
<220> FEATURE:
<223> OTHER INFORMATION: Viral immunosuppression sequence

<400> SEQUENCE: 82

Thr Leu Leu Asn Gly Pro Ala Phe Gln Leu Val Cys Pro Tyr Gly Trp
1               5                   10                  15

Thr Gly Thr Ile Glu Cys
            20


<210> SEQ ID NO 83
<211> LENGTH: 19
<212> TYPE: PRT
<213> ORGANISM: Unknown
<220> FEATURE:
<223> OTHER INFORMATION: Viral immunosuppression sequence

<400> SEQUENCE: 83

Leu Gly Asp Thr Ala Trp Asp Phe Gly Ser Val Gly Gly Val Leu Thr
1               5                   10                  15

Ser Ile Gly


<210> SEQ ID NO 84
<211> LENGTH: 19
<212> TYPE: PRT
<213> ORGANISM: Unknown
<220> FEATURE:
<223> OTHER INFORMATION: Viral immunosuppression sequence

<400> SEQUENCE: 84
```

Leu Gly Asp Thr Ala Trp Asp Phe Gly Ser Val Gly Gly Ile Phe Asn
1 5 10 15

Ser Ile Gly

<210> SEQ ID NO 85
<211> LENGTH: 14
<212> TYPE: PRT
<213> ORGANISM: Unknown
<220> FEATURE:
<223> OTHER INFORMATION: Viral immunosuppression sequence

<400> SEQUENCE: 85

Asn Arg Gly Trp Asn Asn Gly Cys Gly Leu Phe Gly Lys Gly
1 5 10

<210> SEQ ID NO 86
<211> LENGTH: 14
<212> TYPE: PRT
<213> ORGANISM: Unknown
<220> FEATURE:
<223> OTHER INFORMATION: Viral immunosuppression sequence

<400> SEQUENCE: 86

His Ile Arg Ala Gly Pro Tyr Gly His Ala Thr Val Glu Met
1 5 10

<210> SEQ ID NO 87
<211> LENGTH: 15
<212> TYPE: PRT
<213> ORGANISM: Unknown
<220> FEATURE:
<223> OTHER INFORMATION: Viral immunosuppression sequence

<400> SEQUENCE: 87

Pro Glu Trp Ile His Ala His Thr Thr Ser Asp Pro Trp His Pro
1 5 10 15

<210> SEQ ID NO 88
<211> LENGTH: 18
<212> TYPE: PRT
<213> ORGANISM: Unknown
<220> FEATURE:
<223> OTHER INFORMATION: Viral immunosuppression sequence

<400> SEQUENCE: 88

Pro Gly Pro Leu Gly Leu Lys Phe Lys Thr Val Arg Pro Val Ala Leu
1 5 10 15

Pro Arg

<210> SEQ ID NO 89
<211> LENGTH: 21
<212> TYPE: PRT
<213> ORGANISM: Unknown
<220> FEATURE:
<223> OTHER INFORMATION: Viral immunosuppression sequence

<400> SEQUENCE: 89

Ala Leu Ala Pro Pro Arg Asn Val Arg Val Thr Gly Cys Tyr Gln Cys
1 5 10 15

Gly Thr Pro Ala Leu
20

<210> SEQ ID NO 90
<211> LENGTH: 20
<212> TYPE: PRT

-continued

<213> ORGANISM: Unknown
<220> FEATURE:
<223> OTHER INFORMATION: Viral immunosuppression sequence

<400> SEQUENCE: 90

Glu Gly Leu Ala Pro Gly Gly Gly Asn Cys His Leu Thr Val Asn Gly
1 5 10 15

Glu Asp Val Gly
20

<210> SEQ ID NO 91
<211> LENGTH: 20
<212> TYPE: PRT
<213> ORGANISM: Unknown
<220> FEATURE:
<223> OTHER INFORMATION: Viral immunosuppression sequence

<400> SEQUENCE: 91

Glu Gly Leu Ala Pro Gly Gly Gly Asn Cys His Leu Thr Val Asn Gly
1 5 10 15

Glu Asp Val Gly
20

<210> SEQ ID NO 92
<211> LENGTH: 23
<212> TYPE: PRT
<213> ORGANISM: Unknown
<220> FEATURE:
<223> OTHER INFORMATION: Viral immunosuppression sequence

<400> SEQUENCE: 92

Arg Ala Ser Ala Arg Val Ile Asp Pro Ala Ala Gln Ser Phe Thr Gly
1 5 10 15

Val Val Tyr Gly Thr His Thr
20

<210> SEQ ID NO 93
<211> LENGTH: 24
<212> TYPE: PRT
<213> ORGANISM: Unknown
<220> FEATURE:
<223> OTHER INFORMATION: Viral immunosuppression sequence

<400> SEQUENCE: 93

Thr Ala Val Ser Glu Thr Arg Gln Thr Trp Ala Glu Trp Ala Ala Ala
1 5 10 15

His Trp Trp Gln Leu Thr Leu Gly
20

<210> SEQ ID NO 94
<211> LENGTH: 20
<212> TYPE: PRT
<213> ORGANISM: Unknown
<220> FEATURE:
<223> OTHER INFORMATION: Viral immunosuppression sequence

<400> SEQUENCE: 94

Asn Pro Pro Asp Cys Pro Gly Val Gly Thr Gly Cys Thr Ala Cys Gly
1 5 10 15

Val Tyr Leu Asp
20

<210> SEQ ID NO 95
<211> LENGTH: 21

```
<212> TYPE: PRT
<213> ORGANISM: Unknown
<220> FEATURE:
<223> OTHER INFORMATION: Viral immunosuppression sequence

<400> SEQUENCE: 95

Arg Lys Val Cys Ile Gln Leu Gly Thr Glu Gln Thr Cys Lys Thr Ile
1               5                   10                  15

Asp Ser Asn Asp Cys
            20


<210> SEQ ID NO 96
<211> LENGTH: 33
<212> TYPE: PRT
<213> ORGANISM: Unknown
<220> FEATURE:
<223> OTHER INFORMATION: Viral immunosuppression sequence

<400> SEQUENCE: 96

Asp Thr Leu Leu Phe Leu Gly Pro Leu Glu Glu Gly Gly Met Ile Phe
1               5                   10                  15

Lys Gln Trp Cys Thr Thr Thr Cys Gln Phe Gly Asp Pro Gly Asp Ile
            20                  25                  30

Met


<210> SEQ ID NO 97
<211> LENGTH: 24
<212> TYPE: PRT
<213> ORGANISM: Unknown
<220> FEATURE:
<223> OTHER INFORMATION: Viral immunosuppression sequence

<400> SEQUENCE: 97

Gly Ser Phe Arg Lys Lys Cys Ser Phe Ala Thr Leu Pro Ser Cys Gln
1               5                   10                  15

Tyr Asp Gly Asn Thr Val Ser Gly
            20


<210> SEQ ID NO 98
<211> LENGTH: 15
<212> TYPE: PRT
<213> ORGANISM: Unknown
<220> FEATURE:
<223> OTHER INFORMATION: Viral immunosuppression sequence

<400> SEQUENCE: 98

Ala Thr Lys Asp Ser Phe Gln Ser Phe Asn Ile Thr Glu Pro His
1               5                   10                  15


<210> SEQ ID NO 99
<211> LENGTH: 17
<212> TYPE: PRT
<213> ORGANISM: Unknown
<220> FEATURE:
<223> OTHER INFORMATION: Viral immunosuppression sequence

<400> SEQUENCE: 99

Gly Ser Gly Val Gly Phe Asn Leu Val Cys Ser Val Ser Leu Thr Glu
1               5                   10                  15

Cys


<210> SEQ ID NO 100
<211> LENGTH: 22
<212> TYPE: PRT
```

-continued

<213> ORGANISM: Unknown
<220> FEATURE:
<223> OTHER INFORMATION: Viral immunosuppression sequence

<400> SEQUENCE: 100

Lys Ala Cys Asp Ser Ala Met Cys Tyr Gly Ser Ser Thr Ala Asn Leu
1 5 10 15

Val Arg Gly Gln Asn Thr
20

<210> SEQ ID NO 101
<211> LENGTH: 30
<212> TYPE: PRT
<213> ORGANISM: Unknown
<220> FEATURE:
<223> OTHER INFORMATION: Viral immunosuppression sequence

<400> SEQUENCE: 101

Gly Lys Gly Gly His Ser Gly Ser Lys Phe Met Cys Cys His Asp Lys
1 5 10 15

Lys Cys Ser Ala Thr Gly Leu Val Ala Ala Ala Pro His Leu
20 25 30

<210> SEQ ID NO 102
<211> LENGTH: 19
<212> TYPE: PRT
<213> ORGANISM: Unknown
<220> FEATURE:
<223> OTHER INFORMATION: Viral immunosuppression sequence

<400> SEQUENCE: 102

Asp Asp Gly Ala Pro Gln Cys Gly Val His Cys Trp Phe Lys Lys Ser
1 5 10 15

Gly Glu Trp

<210> SEQ ID NO 103
<211> LENGTH: 22
<212> TYPE: PRT
<213> ORGANISM: Unknown
<220> FEATURE:
<223> OTHER INFORMATION: Viral immunosuppression sequence

<400> SEQUENCE: 103

Lys His Asp Glu Leu Cys Thr Gly Pro Cys Pro Val Asn Ile Asn His
1 5 10 15

Gln Thr Gly Trp Leu Thr
20

<210> SEQ ID NO 104
<211> LENGTH: 22
<212> TYPE: PRT
<213> ORGANISM: Unknown
<220> FEATURE:
<223> OTHER INFORMATION: Viral immunosuppression sequence

<400> SEQUENCE: 104

Trp Gly Cys Glu Glu Phe Gly Cys Leu Ala Val Ser Asp Gly Cys Val
1 5 10 15

Phe Gly Ser Cys Gln Asp
20

<210> SEQ ID NO 105
<211> LENGTH: 24
<212> TYPE: PRT

<213> ORGANISM: Unknown
<220> FEATURE:
<223> OTHER INFORMATION: Viral immunosuppression sequence

<400> SEQUENCE: 105

Gly Asn Gly Val Pro Arg Phe Asp Tyr Leu Cys His Leu Ala Ser Arg
1 5 10 15

Lys Glu Val Ile Val Arg Lys Cys
20

<210> SEQ ID NO 106
<211> LENGTH: 14
<212> TYPE: PRT
<213> ORGANISM: Unknown
<220> FEATURE:
<223> OTHER INFORMATION: Viral immunosuppression sequence

<400> SEQUENCE: 106

Ser Cys Ala Gly Cys Ile Asn Cys Phe Gln Asn Ile His Cys
1 5 10

<210> SEQ ID NO 107
<211> LENGTH: 17
<212> TYPE: PRT
<213> ORGANISM: Unknown
<220> FEATURE:
<223> OTHER INFORMATION: Viral immunosuppression sequence

<400> SEQUENCE: 107

Lys Thr Val Ser Ser Glu Leu Ser Cys Arg Glu Gly Gln Ser Tyr Trp
1 5 10 15

Thr

<210> SEQ ID NO 108
<211> LENGTH: 13
<212> TYPE: PRT
<213> ORGANISM: Unknown
<220> FEATURE:
<223> OTHER INFORMATION: Viral immunosuppression sequence

<400> SEQUENCE: 108

Gly Ser Phe Ser Pro Lys Cys Leu Ser Ser Arg Arg Cys
1 5 10

<210> SEQ ID NO 109
<211> LENGTH: 27
<212> TYPE: PRT
<213> ORGANISM: Unknown
<220> FEATURE:
<223> OTHER INFORMATION: Viral immunosuppression sequence

<400> SEQUENCE: 109

Glu Asn Lys Cys Phe Glu Gln Cys Gly Gly Trp Gly Cys Gly Cys Phe
1 5 10 15

Asn Val Asn Pro Ser Cys Leu Phe Val His Thr
20 25

<210> SEQ ID NO 110
<211> LENGTH: 21
<212> TYPE: PRT
<213> ORGANISM: Unknown
<220> FEATURE:
<223> OTHER INFORMATION: Viral immunosuppression sequence

<400> SEQUENCE: 110

Trp Gly Ser Val Ser Leu Ser Leu Asp Ala Glu Gly Ile Ser Gly Ser
1 5 10 15

Asn Ser Phe Ser Phe
20

<210> SEQ ID NO 111
<211> LENGTH: 13
<212> TYPE: PRT
<213> ORGANISM: Unknown
<220> FEATURE:
<223> OTHER INFORMATION: Viral immunosuppression sequence

<400> SEQUENCE: 111

Arg Gln Gly Phe Leu Gly Glu Ile Arg Cys Asn Ser Glu
1 5 10

<210> SEQ ID NO 112
<211> LENGTH: 23
<212> TYPE: PRT
<213> ORGANISM: Unknown
<220> FEATURE:
<223> OTHER INFORMATION: Viral immunosuppression sequence

<400> SEQUENCE: 112

Ala His Glu Ser Cys Leu Arg Ala Pro Asn Leu Val Ser Tyr Lys Pro
1 5 10 15

Met Ile Asp Gln Leu Glu Cys
20

<210> SEQ ID NO 113
<211> LENGTH: 15
<212> TYPE: PRT
<213> ORGANISM: Unknown
<220> FEATURE:
<223> OTHER INFORMATION: Viral immunosuppression sequence

<400> SEQUENCE: 113

Asp Pro Phe Val Val Phe Glu Arg Gly Ser Leu Pro Gln Thr Arg
1 5 10 15

<210> SEQ ID NO 114
<211> LENGTH: 17
<212> TYPE: PRT
<213> ORGANISM: Unknown
<220> FEATURE:
<223> OTHER INFORMATION: Viral immunosuppression sequence

<400> SEQUENCE: 114

Gln Ala Phe Ser Lys Gly Ser Val Gln Ala Asp Leu Thr Leu Met Phe
1 5 10 15

Asp

<210> SEQ ID NO 115
<211> LENGTH: 17
<212> TYPE: PRT
<213> ORGANISM: Unknown
<220> FEATURE:
<223> OTHER INFORMATION: Viral immunosuppression sequence

<400> SEQUENCE: 115

Cys Asp Ala Ala Phe Leu Asn Leu Thr Gly Cys Tyr Ser Cys Asn Ala
1 5 10 15

Gly

<210> SEQ ID NO 116
<211> LENGTH: 19
<212> TYPE: PRT
<213> ORGANISM: Unknown
<220> FEATURE:
<223> OTHER INFORMATION: Viral immunosuppression sequence

<400> SEQUENCE: 116

Cys Gln Ile Leu His Phe Thr Val Pro Glu Val Glu Glu Glu Phe Met
1               5                   10                  15

Tyr Ser Cys

<210> SEQ ID NO 117
<211> LENGTH: 12
<212> TYPE: PRT
<213> ORGANISM: Unknown
<220> FEATURE:
<223> OTHER INFORMATION: Viral immunosuppression sequence

<400> SEQUENCE: 117

Ser Thr Val Val Asn Pro Lys Ser Gly Ser Trp Asn
1               5                   10

<210> SEQ ID NO 118
<211> LENGTH: 17
<212> TYPE: PRT
<213> ORGANISM: Unknown
<220> FEATURE:
<223> OTHER INFORMATION: Viral immunosuppression sequence

<400> SEQUENCE: 118

Phe Phe Asp Trp Phe Ser Gly Leu Met Ser Trp Phe Gly Gly Pro Leu
1               5                   10                  15

Lys

<210> SEQ ID NO 119
<211> LENGTH: 16
<212> TYPE: PRT
<213> ORGANISM: Unknown
<220> FEATURE:
<223> OTHER INFORMATION: Viral immunosuppression sequence

<400> SEQUENCE: 119

Gly Leu Phe Gly Ala Ile Ala Gly Phe Ile Glu Gly Gly Trp Thr Gly
1               5                   10                  15

<210> SEQ ID NO 120
<211> LENGTH: 16
<212> TYPE: PRT
<213> ORGANISM: Unknown
<220> FEATURE:
<223> OTHER INFORMATION: Viral immunosuppression sequence

<400> SEQUENCE: 120

Gly Leu Phe Gly Ala Ile Ala Gly Phe Ile Glu Gly Gly Trp Gln Gly
1               5                   10                  15

<210> SEQ ID NO 121
<211> LENGTH: 16
<212> TYPE: PRT
<213> ORGANISM: Unknown
<220> FEATURE:
<223> OTHER INFORMATION: Viral immunosuppression sequence

<400> SEQUENCE: 121

Gly Ile Phe Gly Ala Ile Ala Gly Phe Ile Glu Asn Gly Trp Glu Gly 1 5 10 15

<210> SEQ ID NO 122
<211> LENGTH: 16
<212> TYPE: PRT
<213> ORGANISM: Unknown
<220> FEATURE:
<223> OTHER INFORMATION: Viral immunosuppression sequence

<400> SEQUENCE: 122

Gly Leu Phe Gly Ala Ile Ala Gly Phe Ile Glu Asn Gly Trp Gln Gly
1 5 10 15

<210> SEQ ID NO 123
<211> LENGTH: 16
<212> TYPE: PRT
<213> ORGANISM: Unknown
<220> FEATURE:
<223> OTHER INFORMATION: Viral immunosuppression sequence

<400> SEQUENCE: 123

Gly Ile Phe Gly Ala Ile Ala Gly Phe Ile Glu Gly Gly Trp Thr Gly
1 5 10 15

<210> SEQ ID NO 124
<211> LENGTH: 16
<212> TYPE: PRT
<213> ORGANISM: Unknown
<220> FEATURE:
<223> OTHER INFORMATION: Viral immunosuppression sequence

<400> SEQUENCE: 124

Gly Leu Phe Gly Ala Ile Ala Gly Phe Ile Glu Gly Gly Trp Ser Gly
1 5 10 15

<210> SEQ ID NO 125
<211> LENGTH: 16
<212> TYPE: PRT
<213> ORGANISM: Unknown
<220> FEATURE:
<223> OTHER INFORMATION: Viral immunosuppression sequence

<400> SEQUENCE: 125

Gly Leu Phe Gly Ala Ile Ala Gly Phe Ile Glu Gly Gly Trp Pro Gly
1 5 10 15

<210> SEQ ID NO 126
<211> LENGTH: 16
<212> TYPE: PRT
<213> ORGANISM: Unknown
<220> FEATURE:
<223> OTHER INFORMATION: Viral immunosuppression sequence

<400> SEQUENCE: 126

Gly Phe Phe Gly Ala Ile Ala Gly Phe Leu Glu Gly Gly Trp Glu Gly
1 5 10 15

<210> SEQ ID NO 127
<211> LENGTH: 16
<212> TYPE: PRT
<213> ORGANISM: Unknown
<220> FEATURE:
<223> OTHER INFORMATION: Viral immunosuppression sequence

<400> SEQUENCE: 127

Gly Ala Ile Ala Leu Gly Val Ala Thr Ala Ala Ala Val Thr Ala Gly
1 5 10 15

<210> SEQ ID NO 128
<211> LENGTH: 17
<212> TYPE: PRT
<213> ORGANISM: Unknown
<220> FEATURE:
<223> OTHER INFORMATION: Viral immunosuppression sequence

<400> SEQUENCE: 128

Phe Leu Gly Leu Ile Leu Gly Leu Gly Ala Ala Val Thr Ala Gly Val
1 5 10 15

Ala

<210> SEQ ID NO 129
<211> LENGTH: 15
<212> TYPE: PRT
<213> ORGANISM: Unknown
<220> FEATURE:
<223> OTHER INFORMATION: Viral immunosuppression sequence

<400> SEQUENCE: 129

Thr Asn Glu Ala Val Val Ser Leu Thr Asn Gly Met Ser Val Leu
1 5 10 15

<210> SEQ ID NO 130
<211> LENGTH: 13
<212> TYPE: PRT
<213> ORGANISM: Unknown
<220> FEATURE:
<223> OTHER INFORMATION: Viral immunosuppression sequence

<400> SEQUENCE: 130

Val Ile Arg Phe Gln Gln Leu Asn Lys Arg Leu Leu Glu
1 5 10

<210> SEQ ID NO 131
<211> LENGTH: 10
<212> TYPE: PRT
<213> ORGANISM: Unknown
<220> FEATURE:
<223> OTHER INFORMATION: Viral immunosuppression sequence

<400> SEQUENCE: 131

Arg Glu Phe Ser Ser Asn Ala Gly Leu Thr
1 5 10

<210> SEQ ID NO 132
<211> LENGTH: 14
<212> TYPE: PRT
<213> ORGANISM: Unknown
<220> FEATURE:
<223> OTHER INFORMATION: Viral immunosuppression sequence

<400> SEQUENCE: 132

Met Leu Thr Asp Arg Glu Leu Thr Ser Ile Val Gly Gly Met
1 5 10

<210> SEQ ID NO 133
<211> LENGTH: 16
<212> TYPE: PRT
<213> ORGANISM: Unknown
<220> FEATURE:
<223> OTHER INFORMATION: Viral immunosuppression sequence

<400> SEQUENCE: 133

Tyr Val Ile Gln Leu Pro Leu Phe Gly Val Met Asp Thr Asp Cys Trp 1 5 10 15

<210> SEQ ID NO 134
<211> LENGTH: 21
<212> TYPE: PRT
<213> ORGANISM: Unknown
<220> FEATURE:
<223> OTHER INFORMATION: Viral immunosuppression sequence

<400> SEQUENCE: 134

Cys Leu Ala Arg Ala Asp Asn Gly Trp Tyr Cys His Asn Ala Gly Ser
1 5 10 15

Leu Ser Tyr Phe Pro
20

<210> SEQ ID NO 135
<211> LENGTH: 16
<212> TYPE: PRT
<213> ORGANISM: Unknown
<220> FEATURE:
<223> OTHER INFORMATION: Viral immunosuppression sequence

<400> SEQUENCE: 135

Asp Thr Leu Lys Ser Leu Thr Val Pro Val Thr Ser Arg Glu Cys Asn
1 5 10 15

<210> SEQ ID NO 136
<211> LENGTH: 21
<212> TYPE: PRT
<213> ORGANISM: Unknown
<220> FEATURE:
<223> OTHER INFORMATION: Viral immunosuppression sequence

<400> SEQUENCE: 136

Tyr Asp Cys Lys Ile Ser Thr Ser Lys Thr Tyr Val Ser Thr Ala Val
1 5 10 15

Leu Thr Thr Met Gly
20

<210> SEQ ID NO 137
<211> LENGTH: 13
<212> TYPE: PRT
<213> ORGANISM: Unknown
<220> FEATURE:
<223> OTHER INFORMATION: Viral immunosuppression sequence

<400> SEQUENCE: 137

Val Ser Cys Tyr Gly His Asn Ser Cys Thr Val Ile Asn
1 5 10

<210> SEQ ID NO 138
<211> LENGTH: 13
<212> TYPE: PRT
<213> ORGANISM: Unknown
<220> FEATURE:
<223> OTHER INFORMATION: Viral immunosuppression sequence

<400> SEQUENCE: 138

Val Ser Cys Tyr Gly His Asn Ser Cys Thr Val Ile Asn
1 5 10

<210> SEQ ID NO 139
<211> LENGTH: 34
<212> TYPE: PRT
<213> ORGANISM: Unknown
<220> FEATURE:

<223> OTHER INFORMATION: Viral immunosuppression sequence

<400> SEQUENCE: 139

Pro Leu Ser Phe Pro Asp Asp Lys Phe Asp Val Ala Ile Arg Asp Val
1 5 10 15

Glu His Ser Ile Asn Gln Thr Arg Thr Phe Leu Lys Ala Ser Asp Gln
20 25 30

Leu Leu

<210> SEQ ID NO 140
<211> LENGTH: 25
<212> TYPE: PRT
<213> ORGANISM: Unknown
<220> FEATURE:
<223> OTHER INFORMATION: Viral immunosuppression sequence

<400> SEQUENCE: 140

Lys Ile Met Thr Ser Lys Thr Asp Ile Ser Ser Ser Val Ile Thr Ser
1 5 10 15

Ile Gly Ala Ile Val Ser Cys Tyr Gly
20 25

<210> SEQ ID NO 141
<211> LENGTH: 18
<212> TYPE: PRT
<213> ORGANISM: Unknown
<220> FEATURE:
<223> OTHER INFORMATION: Viral immunosuppression sequence

<400> SEQUENCE: 141

Arg Ser Ala Ile Glu Asp Leu Leu Phe Asp Lys Val Lys Leu Ser Asp
1 5 10 15

Val Gly

<210> SEQ ID NO 142
<211> LENGTH: 17
<212> TYPE: PRT
<213> ORGANISM: Unknown
<220> FEATURE:
<223> OTHER INFORMATION: Viral immunosuppression sequence

<400> SEQUENCE: 142

Val Pro Phe Tyr Leu Asn Val Gln Tyr Arg Ile Asn Gly Leu Gly Val
1 5 10 15

Thr

<210> SEQ ID NO 143
<211> LENGTH: 21
<212> TYPE: PRT
<213> ORGANISM: Unknown
<220> FEATURE:
<223> OTHER INFORMATION: Viral immunosuppression sequence

<400> SEQUENCE: 143

Val Leu Ser Gln Asn Gln Lys Leu Ile Ala Asn Ala Phe Asn Asn Ala
1 5 10 15

Leu His Ala Ile Gln
20

<210> SEQ ID NO 144
<211> LENGTH: 16
<212> TYPE: PRT
<213> ORGANISM: Unknown

<220> FEATURE:
<223> OTHER INFORMATION: Viral immunosuppression sequence

<400> SEQUENCE: 144

Thr Asn Ser Ala Leu Val Lys Ile Gln Ala Val Val Asn Ala Asn Ala
1 5 10 15

<210> SEQ ID NO 145
<211> LENGTH: 24
<212> TYPE: PRT
<213> ORGANISM: Unknown
<220> FEATURE:
<223> OTHER INFORMATION: Viral immunosuppression sequence

<400> SEQUENCE: 145

Ala Glu Ala Gln Ile Asp Arg Leu Ile Asn Gly Arg Leu Thr Ala Leu
1 5 10 15

Asn Ala Tyr Val Ser Gln Gln Leu
20

<210> SEQ ID NO 146
<211> LENGTH: 31
<212> TYPE: PRT
<213> ORGANISM: Unknown
<220> FEATURE:
<223> OTHER INFORMATION: Viral immunosuppression sequence

<400> SEQUENCE: 146

Ser Ala Ala Gln Ala Met Glu Lys Val Asn Glu Cys Val Lys Ser Gln
1 5 10 15

Ser Ser Arg Ile Asn Phe Cys Gly Asn Gly Asn His Ile Ile Ser
20 25 30

<210> SEQ ID NO 147
<211> LENGTH: 14
<212> TYPE: PRT
<213> ORGANISM: Unknown
<220> FEATURE:
<223> OTHER INFORMATION: Viral immunosuppression sequence

<400> SEQUENCE: 147

Ala Pro Tyr Gly Leu Tyr Phe Ile His Phe Asn Tyr Val Pro
1 5 10

<210> SEQ ID NO 148
<211> LENGTH: 32
<212> TYPE: PRT
<213> ORGANISM: Unknown
<220> FEATURE:
<223> OTHER INFORMATION: Viral immunosuppression sequence

<400> SEQUENCE: 148

Leu Gln Glu Ala Ile Lys Val Leu Asn His Ser Tyr Ile Asn Leu Lys
1 5 10 15

Asp Ile Gly Thr Tyr Glu Tyr Tyr Val Lys Trp Pro Trp Tyr Val Trp
20 25 30

<210> SEQ ID NO 149
<211> LENGTH: 23
<212> TYPE: PRT
<213> ORGANISM: Unknown
<220> FEATURE:
<223> OTHER INFORMATION: Viral immunosuppression sequence

<400> SEQUENCE: 149

```
Asn Ala Leu Ile Asn Asp Gln Leu Ile Met Lys Asn His Leu Arg Asp
1               5                   10                  15

Ile Met Gly Ile Pro Tyr Cys
            20


<210> SEQ ID NO 150
<211> LENGTH: 20
<212> TYPE: PRT
<213> ORGANISM: Unknown
<220> FEATURE:
<223> OTHER INFORMATION: Viral immunosuppression sequence

<400> SEQUENCE: 150

Phe Thr Trp Thr Leu Ser Asp Ser Glu Gly Lys Asp Thr Pro Gly Gly
1               5                   10                  15

Tyr Cys Leu Thr
            20


<210> SEQ ID NO 151
<211> LENGTH: 29
<212> TYPE: PRT
<213> ORGANISM: Unknown
<220> FEATURE:
<223> OTHER INFORMATION: Viral immunosuppression sequence

<400> SEQUENCE: 151

Lys Cys Phe Gly Asn Thr Ala Ile Ala Lys Cys Asn Gln Lys His Asp
1               5                   10                  15

Glu Glu Phe Cys Asp Met Leu Arg Leu Phe Asp Phe Asn
            20                  25


<210> SEQ ID NO 152
<211> LENGTH: 24
<212> TYPE: PRT
<213> ORGANISM: Unknown
<220> FEATURE:
<223> OTHER INFORMATION: Viral immunosuppression sequence

<400> SEQUENCE: 152

Met Leu Gln Lys Glu Tyr Met Glu Arg Gln Gly Lys Thr Pro Leu Gly
1               5                   10                  15

Leu Val Asp Leu Phe Val Phe Ser
            20


<210> SEQ ID NO 153
<211> LENGTH: 16
<212> TYPE: PRT
<213> ORGANISM: Unknown
<220> FEATURE:
<223> OTHER INFORMATION: Viral immunosuppression sequence

<400> SEQUENCE: 153

Phe Asn Pro Leu Gly Phe Phe Pro Ser His Gln Leu Asp Pro Leu Phe
1               5                   10                  15


<210> SEQ ID NO 154
<211> LENGTH: 13
<212> TYPE: PRT
<213> ORGANISM: Unknown
<220> FEATURE:
<223> OTHER INFORMATION: Viral immunosuppression sequence

<400> SEQUENCE: 154

Ala Asp Trp Asp Lys Asn Pro Asn Lys Asp Pro Trp Pro
1               5                   10
```

<210> SEQ ID NO 155
<211> LENGTH: 20
<212> TYPE: PRT
<213> ORGANISM: Unknown
<220> FEATURE:
<223> OTHER INFORMATION: Viral immunosuppression sequence

<400> SEQUENCE: 155

Met Glu Ser Ile Thr Ser Gly Phe Leu Gly Pro Leu Leu Val Leu Gln
1 5 10 15

Ala Val Phe Phe
20

<210> SEQ ID NO 156
<211> LENGTH: 25
<212> TYPE: PRT
<213> ORGANISM: Unknown
<220> FEATURE:
<223> OTHER INFORMATION: Viral immunosuppression sequence

<400> SEQUENCE: 156

Leu Leu Thr Arg Ile Leu Thr Ile Pro Gln Ser Leu Asp Ser Trp Trp
1 5 10 15

Thr Ser Leu Asn Phe Leu Gly Gly Ala
20 25

<210> SEQ ID NO 157
<211> LENGTH: 12
<212> TYPE: PRT
<213> ORGANISM: Unknown
<220> FEATURE:
<223> OTHER INFORMATION: Viral immunosuppression sequence

<400> SEQUENCE: 157

Cys Pro Pro Thr Cys Pro Gly Tyr Arg Trp Met Cys
1 5 10

<210> SEQ ID NO 158
<211> LENGTH: 18
<212> TYPE: PRT
<213> ORGANISM: Unknown
<220> FEATURE:
<223> OTHER INFORMATION: Viral immunosuppression sequence

<400> SEQUENCE: 158

Leu Phe Ile Leu Leu Leu Cys Leu Ile Phe Leu Leu Val Leu Leu Asp
1 5 10 15

Tyr Gln

<210> SEQ ID NO 159
<211> LENGTH: 15
<212> TYPE: PRT
<213> ORGANISM: Unknown
<220> FEATURE:
<223> OTHER INFORMATION: Viral immunosuppression sequence

<400> SEQUENCE: 159

Glu Thr Arg Thr Val Trp Gln Leu Ser Val Ala Gly Val Ser Cys
1 5 10 15

<210> SEQ ID NO 160
<211> LENGTH: 24
<212> TYPE: PRT
<213> ORGANISM: Unknown

<220> FEATURE:
<223> OTHER INFORMATION: Viral immunosuppression sequence

<400> SEQUENCE: 160

Leu Asp Gly Tyr Leu Cys Arg Lys Gln Lys Trp Glu Val Thr Cys Thr
1 5 10 15

Glu Thr Trp Tyr Phe Val Thr Asp
20

<210> SEQ ID NO 161
<211> LENGTH: 14
<212> TYPE: PRT
<213> ORGANISM: Unknown
<220> FEATURE:
<223> OTHER INFORMATION: Viral immunosuppression sequence

<400> SEQUENCE: 161

Lys Tyr Gln Ile Ile Glu Val Ile Pro Thr Glu Asn Glu Cys
1 5 10

<210> SEQ ID NO 162
<211> LENGTH: 24
<212> TYPE: PRT
<213> ORGANISM: Unknown
<220> FEATURE:
<223> OTHER INFORMATION: Viral immunosuppression sequence

<400> SEQUENCE: 162

Leu Lys Gly Glu Tyr Ile Pro Pro Tyr Tyr Pro Pro Thr Asn Cys Val
1 5 10 15

Trp Asn Ala Ile Asp Thr Gln Glu
20

<210> SEQ ID NO 163
<211> LENGTH: 18
<212> TYPE: PRT
<213> ORGANISM: Unknown
<220> FEATURE:
<223> OTHER INFORMATION: Viral immunosuppression sequence

<400> SEQUENCE: 163

Ile Glu Asp Pro Val Thr Met Thr Leu Met Asp Ser Lys Phe Thr Lys
1 5 10 15

Pro Cys

<210> SEQ ID NO 164
<211> LENGTH: 13
<212> TYPE: PRT
<213> ORGANISM: Unknown
<220> FEATURE:
<223> OTHER INFORMATION: Viral immunosuppression sequence

<400> SEQUENCE: 164

Leu His Cys Gln Ile Lys Ser Trp Glu Cys Ile Pro Val
1 5 10

<210> SEQ ID NO 165
<211> LENGTH: 15
<212> TYPE: PRT
<213> ORGANISM: Unknown
<220> FEATURE:
<223> OTHER INFORMATION: Viral immunosuppression sequence

<400> SEQUENCE: 165

Ser His Arg Asn Met Met Glu Ala Leu Tyr Leu Glu Ser Pro Asp

-continued 1 5 10 15

<210> SEQ ID NO 166
<211> LENGTH: 20
<212> TYPE: PRT
<213> ORGANISM: Unknown
<220> FEATURE:
<223> OTHER INFORMATION: Viral immunosuppression sequence

<400> SEQUENCE: 166

Leu Thr Phe Cys Gly Tyr Asn Gly Ile Leu Leu Asp Asn Gly Glu Trp
1 5 10 15

Trp Ser Ile Tyr
20

<210> SEQ ID NO 167
<211> LENGTH: 18
<212> TYPE: PRT
<213> ORGANISM: Unknown
<220> FEATURE:
<223> OTHER INFORMATION: Viral immunosuppression sequence

<400> SEQUENCE: 167

Glu Leu Glu His Glu Lys Cys Leu Gly Thr Leu Glu Lys Leu Gln Asn
1 5 10 15

Gly Glu

<210> SEQ ID NO 168
<211> LENGTH: 17
<212> TYPE: PRT
<213> ORGANISM: Unknown
<220> FEATURE:
<223> OTHER INFORMATION: Viral immunosuppression sequence

<400> SEQUENCE: 168

Leu Asp Leu Ser Tyr Leu Ser Pro Ser Asn Pro Gly Lys His Tyr Ala
1 5 10 15

Tyr

<210> SEQ ID NO 169
<211> LENGTH: 15
<212> TYPE: PRT
<213> ORGANISM: Unknown
<220> FEATURE:
<223> OTHER INFORMATION: Viral immunosuppression sequence

<400> SEQUENCE: 169

Ile Arg Ala Val Cys Tyr Tyr His Thr Phe Ser Met Asn Leu Asp
1 5 10 15

<210> SEQ ID NO 170
<211> LENGTH: 20
<212> TYPE: PRT
<213> ORGANISM: Unknown
<220> FEATURE:
<223> OTHER INFORMATION: Viral immunosuppression sequence

<400> SEQUENCE: 170

Glu Trp Lys Thr Thr Cys Asp Tyr Arg Trp Tyr Gly Pro Gln Tyr Ile
1 5 10 15

Thr His Ser Ile
20

<210> SEQ ID NO 171

<211> LENGTH: 15
<212> TYPE: PRT
<213> ORGANISM: Unknown
<220> FEATURE:
<223> OTHER INFORMATION: Viral immunosuppression sequence

<400> SEQUENCE: 171

Leu Gly Phe Pro Pro Gln Ser Cys Gly Trp Ala Ser Val Thr Thr
1               5                   10                  15

<210> SEQ ID NO 172
<211> LENGTH: 23
<212> TYPE: PRT
<213> ORGANISM: Unknown
<220> FEATURE:
<223> OTHER INFORMATION: Viral immunosuppression sequence

<400> SEQUENCE: 172

Lys Gly Ser Ser Ile Gly Lys Met Phe Glu Ser Thr Tyr Arg Gly Ala
1               5                   10                  15

Lys Arg Met Ala Ile Leu Gly
            20

<210> SEQ ID NO 173
<211> LENGTH: 23
<212> TYPE: PRT
<213> ORGANISM: Unknown
<220> FEATURE:
<223> OTHER INFORMATION: Viral immunosuppression sequence

<400> SEQUENCE: 173

Lys Gly Ser Ser Ile Gly Lys Met Phe Glu Ala Thr Ala Arg Gly Ala
1               5                   10                  15

Arg Arg Met Ala Ile Leu Gly
            20

<210> SEQ ID NO 174
<211> LENGTH: 23
<212> TYPE: PRT
<213> ORGANISM: Unknown
<220> FEATURE:
<223> OTHER INFORMATION: Viral immunosuppression sequence

<400> SEQUENCE: 174

Lys Gly Ser Ser Ile Gly Gln Met Phe Glu Thr Thr Met Arg Gly Ala
1               5                   10                  15

Lys Arg Met Ala Ile Leu Gly
            20

<210> SEQ ID NO 175
<211> LENGTH: 18
<212> TYPE: PRT
<213> ORGANISM: Unknown
<220> FEATURE:
<223> OTHER INFORMATION: Viral immunosuppression sequence

<400> SEQUENCE: 175

Pro Ala Leu Ser Thr Gly Leu Ile His Leu His Gln Asn Ile Val Asp
1               5                   10                  15

Val Gln

<210> SEQ ID NO 176
<211> LENGTH: 18
<212> TYPE: PRT
<213> ORGANISM: Unknown

<220> FEATURE:
<223> OTHER INFORMATION: Viral immunosuppression sequence

<400> SEQUENCE: 176

Pro Ala Leu Ser Thr Gly Leu Ile His Leu His Arg Asn Ile Val Asp
1 5 10 15

Val Gln

<210> SEQ ID NO 177
<211> LENGTH: 18
<212> TYPE: PRT
<213> ORGANISM: Unknown
<220> FEATURE:
<223> OTHER INFORMATION: Viral immunosuppression sequence

<400> SEQUENCE: 177

Pro Ala Leu Ser Thr Gly Leu Ile His Leu His Gln Asn Ile Val Asp
1 5 10 15

Thr Gln

<210> SEQ ID NO 178
<211> LENGTH: 18
<212> TYPE: PRT
<213> ORGANISM: Unknown
<220> FEATURE:
<223> OTHER INFORMATION: Viral immunosuppression sequence

<400> SEQUENCE: 178

Trp Thr Tyr Asn Ala Glu Leu Leu Val Leu Leu Glu Asn Glu Arg Thr
1 5 10 15

Leu Asp

<210> SEQ ID NO 179
<211> LENGTH: 18
<212> TYPE: PRT
<213> ORGANISM: Unknown
<220> FEATURE:
<223> OTHER INFORMATION: Viral immunosuppression sequence

<400> SEQUENCE: 179

Asn Ala Glu Leu Leu Val Leu Leu Glu Asn Glu Arg Thr Leu Asp Tyr
1 5 10 15

His Asp

<210> SEQ ID NO 180
<211> LENGTH: 18
<212> TYPE: PRT
<213> ORGANISM: Unknown
<220> FEATURE:
<223> OTHER INFORMATION: Viral immunosuppression sequence

<400> SEQUENCE: 180

Trp Thr Tyr Asn Ala Glu Leu Leu Val Leu Met Glu Asn Glu Arg Thr
1 5 10 15

Leu Asp

<210> SEQ ID NO 181
<211> LENGTH: 18
<212> TYPE: PRT
<213> ORGANISM: Unknown
<220> FEATURE:
<223> OTHER INFORMATION: Viral immunosuppression sequence

<400> SEQUENCE: 181

Asn Ala Glu Leu Leu Val Leu Met Glu Asn Glu Arg Thr Leu Asp Tyr
1 5 10 15

His Asp

<210> SEQ ID NO 182
<211> LENGTH: 18
<212> TYPE: PRT
<213> ORGANISM: Unknown
<220> FEATURE:
<223> OTHER INFORMATION: Viral immunosuppression sequence

<400> SEQUENCE: 182

Trp Ser Tyr Asn Ala Glu Leu Leu Val Ala Leu Glu Asn Gln His Thr
1 5 10 15

Ile Asp

<210> SEQ ID NO 183
<211> LENGTH: 18
<212> TYPE: PRT
<213> ORGANISM: Unknown
<220> FEATURE:
<223> OTHER INFORMATION: Viral immunosuppression sequence

<400> SEQUENCE: 183

Asn Ala Glu Leu Leu Val Ala Leu Glu Asn Gln His Thr Ile Asp Leu
1 5 10 15

Thr Asp

<210> SEQ ID NO 184
<211> LENGTH: 18
<212> TYPE: PRT
<213> ORGANISM: Unknown
<220> FEATURE:
<223> OTHER INFORMATION: Viral immunosuppression sequence

<400> SEQUENCE: 184

Asn Ala Glu Leu Leu Val Ala Leu Glu Asn Gln His Thr Ile Asp Val
1 5 10 15

Thr Asp

<210> SEQ ID NO 185
<211> LENGTH: 18
<212> TYPE: PRT
<213> ORGANISM: Unknown
<220> FEATURE:
<223> OTHER INFORMATION: Viral immunosuppression sequence

<400> SEQUENCE: 185

Asn Ala Glu Leu Leu Val Leu Met Glu Asn Glu Arg Thr Leu Asp Phe
1 5 10 15

His Asp

<210> SEQ ID NO 186
<211> LENGTH: 18
<212> TYPE: PRT
<213> ORGANISM: Unknown
<220> FEATURE:
<223> OTHER INFORMATION: Viral immunosuppression sequence

<400> SEQUENCE: 186

Asn Ala Glu Leu Leu Val Leu Leu Glu Asn Glu Arg Thr Leu Asp Met
1 5 10 15

His Asp

<210> SEQ ID NO 187
<211> LENGTH: 18
<212> TYPE: PRT
<213> ORGANISM: Unknown
<220> FEATURE:
<223> OTHER INFORMATION: Viral immunosuppression sequence

<400> SEQUENCE: 187

Trp Ser Tyr Asn Ala Glu Leu Leu Val Ala Met Glu Asn Gln His Thr
1 5 10 15

Ile Asp

<210> SEQ ID NO 188
<211> LENGTH: 18
<212> TYPE: PRT
<213> ORGANISM: Unknown
<220> FEATURE:
<223> OTHER INFORMATION: Viral immunosuppression sequence

<400> SEQUENCE: 188

Asn Ala Glu Leu Leu Val Ala Met Glu Asn Gln His Thr Ile Asp Leu
1 5 10 15

Ala Asp

<210> SEQ ID NO 189
<211> LENGTH: 18
<212> TYPE: PRT
<213> ORGANISM: Unknown
<220> FEATURE:
<223> OTHER INFORMATION: Viral immunosuppression sequence

<400> SEQUENCE: 189

Trp Ala Tyr Asn Ala Glu Leu Leu Val Leu Leu Glu Asn Gln Lys Thr
1 5 10 15

Leu Asp

<210> SEQ ID NO 190
<211> LENGTH: 18
<212> TYPE: PRT
<213> ORGANISM: Unknown
<220> FEATURE:
<223> OTHER INFORMATION: Viral immunosuppression sequence

<400> SEQUENCE: 190

Asn Ala Glu Leu Leu Val Leu Leu Glu Asn Gln Lys Thr Leu Asp Glu
1 5 10 15

His Asp

<210> SEQ ID NO 191
<211> LENGTH: 18
<212> TYPE: PRT
<213> ORGANISM: Unknown
<220> FEATURE:
<223> OTHER INFORMATION: Viral immunosuppression sequence

<400> SEQUENCE: 191

Trp Thr Tyr Gln Ala Glu Leu Leu Val Ala Met Glu Asn Gln His Thr
1 5 10 15

Ile Asp

<210> SEQ ID NO 192

<211> LENGTH: 18
<212> TYPE: PRT
<213> ORGANISM: Unknown
<220> FEATURE:
<223> OTHER INFORMATION: Viral immunosuppression sequence

<400> SEQUENCE: 192

Gln Ala Glu Leu Leu Val Ala Met Glu Asn Gln His Thr Ile Asp Met
1 5 10 15

Ala Asp

<210> SEQ ID NO 193
<211> LENGTH: 18
<212> TYPE: PRT
<213> ORGANISM: Unknown
<220> FEATURE:
<223> OTHER INFORMATION: Viral immunosuppression sequence

<400> SEQUENCE: 193

Trp Ser Tyr Asn Ala Gln Leu Leu Val Leu Leu Glu Asn Glu Lys Thr
1 5 10 15

Leu Asp

<210> SEQ ID NO 194
<211> LENGTH: 18
<212> TYPE: PRT
<213> ORGANISM: Unknown
<220> FEATURE:
<223> OTHER INFORMATION: Viral immunosuppression sequence

<400> SEQUENCE: 194

Asn Ala Gln Leu Leu Val Leu Leu Glu Asn Glu Lys Thr Leu Asp Leu
1 5 10 15

His Asp

<210> SEQ ID NO 195
<211> LENGTH: 18
<212> TYPE: PRT
<213> ORGANISM: Unknown
<220> FEATURE:
<223> OTHER INFORMATION: Viral immunosuppression sequence

<400> SEQUENCE: 195

Trp Ser Tyr Asn Ala Lys Leu Leu Val Leu Leu Glu Asn Asp Lys Thr
1 5 10 15

Leu Asp

<210> SEQ ID NO 196
<211> LENGTH: 18
<212> TYPE: PRT
<213> ORGANISM: Unknown
<220> FEATURE:
<223> OTHER INFORMATION: Viral immunosuppression sequence

<400> SEQUENCE: 196

Asn Ala Lys Leu Leu Val Leu Leu Glu Asn Asp Lys Thr Leu Asp Met
1 5 10 15

His Asp

<210> SEQ ID NO 197
<211> LENGTH: 18
<212> TYPE: PRT
<213> ORGANISM: Unknown
<220> FEATURE:

<223> OTHER INFORMATION: Viral immunosuppression sequence

<400> SEQUENCE: 197

Trp Ser Tyr Asn Ala Lys Leu Leu Val Leu Ile Glu Asn Asp Arg Thr
1 5 10 15

Leu Asp

<210> SEQ ID NO 198
<211> LENGTH: 18
<212> TYPE: PRT
<213> ORGANISM: Unknown
<220> FEATURE:
<223> OTHER INFORMATION: Viral immunosuppression sequence

<400> SEQUENCE: 198

Asn Ala Lys Leu Leu Val Leu Ile Glu Asn Asp Arg Thr Leu Asp Leu
1 5 10 15

His Asp

<210> SEQ ID NO 199
<211> LENGTH: 18
<212> TYPE: PRT
<213> ORGANISM: Unknown
<220> FEATURE:
<223> OTHER INFORMATION: Viral immunosuppression sequence

<400> SEQUENCE: 199

Ile Ser Ser Gln Ile Glu Leu Ala Val Leu Leu Ser Asn Glu Gly Ile
1 5 10 15

Ile Asn

<210> SEQ ID NO 200
<211> LENGTH: 18
<212> TYPE: PRT
<213> ORGANISM: Unknown
<220> FEATURE:
<223> OTHER INFORMATION: Viral immunosuppression sequence

<400> SEQUENCE: 200

Gln Ile Glu Leu Ala Val Leu Leu Ser Asn Glu Gly Ile Ile Asn Ser
1 5 10 15

Glu Asp

<210> SEQ ID NO 201
<211> LENGTH: 15
<212> TYPE: PRT
<213> ORGANISM: Unknown
<220> FEATURE:
<223> OTHER INFORMATION: Viral immunosuppression sequence

<400> SEQUENCE: 201

Gly Leu Phe Gly Ala Ala Gly Phe Ile Glu Asn Gly Trp Glu Gly
1 5 10 15

<210> SEQ ID NO 202
<211> LENGTH: 14
<212> TYPE: PRT
<213> ORGANISM: Unknown
<220> FEATURE:
<223> OTHER INFORMATION: Viral immunosuppression sequence

<400> SEQUENCE: 202

Asp Arg Gly Trp Gly Asn Gly Cys Gly Asp Phe Gly Lys Gly
1 5 10

<210> SEQ ID NO 203
<211> LENGTH: 18
<212> TYPE: PRT
<213> ORGANISM: Unknown
<220> FEATURE:
<223> OTHER INFORMATION: Viral immunosuppression sequence

<400> SEQUENCE: 203

```
Asn Ala Glu Leu Leu Val Leu Leu Glu Asn Glu Arg Thr Leu Asp Phe
1               5                   10                  15

His Asp
```

<210> SEQ ID NO 204
<211> LENGTH: 19
<212> TYPE: PRT
<213> ORGANISM: Unknown
<220> FEATURE:
<223> OTHER INFORMATION: Viral immunosuppression sequence

<400> SEQUENCE: 204

```
Gly Asp Thr Ala Trp Asp Phe Gly Ser Val Gly Gly Val Leu Asn Ser
1               5                   10                  15

Leu Gly Lys
```

<210> SEQ ID NO 205
<211> LENGTH: 27
<212> TYPE: PRT
<213> ORGANISM: Unknown
<220> FEATURE:
<223> OTHER INFORMATION: Viral immunosuppression sequence

<400> SEQUENCE: 205

```
Thr Leu Leu Asn Gly Pro Ala Phe Gln Leu Val Cys Pro Tyr Gly Trp
1               5                   10                  15

Thr Gly Thr Ile Glu Cys Asp Ser Tyr Tyr Gln
            20                  25
```

<210> SEQ ID NO 206
<211> LENGTH: 18
<212> TYPE: PRT
<213> ORGANISM: Unknown
<220> FEATURE:
<223> OTHER INFORMATION: Viral immunosuppression sequence

<400> SEQUENCE: 206

```
Gln Tyr Ile Ile Lys Ser Gly Tyr Gln Tyr Trp Phe Asp Leu Thr Ala
1               5                   10                  15

Lys Asp
```

<210> SEQ ID NO 207
<211> LENGTH: 14
<212> TYPE: PRT
<213> ORGANISM: Unknown
<220> FEATURE:
<223> OTHER INFORMATION: Viral immunosuppression sequence

<400> SEQUENCE: 207

```
Leu Leu Asn Thr Pro Pro Pro Tyr Gln Val Ser Cys Gly Gly
1               5                   10
```

<210> SEQ ID NO 208
<211> LENGTH: 18
<212> TYPE: PRT

<213> ORGANISM: Unknown
<220> FEATURE:
<223> OTHER INFORMATION: Viral immunosuppression sequence

<400> SEQUENCE: 208

Trp Ser Tyr Asn Ala Glu Leu Leu Val Ala Met Glu Asn Gln His Leu
1               5                   10                  15

Ala Asp

<210> SEQ ID NO 209
<211> LENGTH: 36
<212> TYPE: PRT
<213> ORGANISM: Unknown
<220> FEATURE:
<223> OTHER INFORMATION: Viral immunosuppression sequence

<400> SEQUENCE: 209

Gly Ile Ile Arg Thr Leu Pro Asp Gly Cys His Tyr Ile Ser Asn Lys
1               5                   10                  15

Gly Val Asp Arg Val Gln Val Gly Asn Thr Val Tyr Tyr Leu Ser Lys
            20                  25                  30

Glu Val Gly Lys
        35

<210> SEQ ID NO 210
<211> LENGTH: 22
<212> TYPE: PRT
<213> ORGANISM: Unknown
<220> FEATURE:
<223> OTHER INFORMATION: Viral immunosuppression sequence

<400> SEQUENCE: 210

Glu Ser Leu Val Ile Ile Ser Pro Ser Val Ala Asp Leu Asp Pro Tyr
1               5                   10                  15

Asp Arg Ser Leu His Ser
            20

<210> SEQ ID NO 211
<211> LENGTH: 17
<212> TYPE: PRT
<213> ORGANISM: Unknown
<220> FEATURE:
<223> OTHER INFORMATION: Viral immunosuppression sequence

<400> SEQUENCE: 211

Cys Lys Leu Lys Leu Cys Gly Val Leu Gly Leu Arg Leu Met Asp Gly
1               5                   10                  15

Thr

<210> SEQ ID NO 212
<211> LENGTH: 16
<212> TYPE: PRT
<213> ORGANISM: Unknown
<220> FEATURE:
<223> OTHER INFORMATION: Viral immunosuppression sequence

<400> SEQUENCE: 212

Ile Leu Gly Pro Asp Gly Asn Val Leu Ile Pro Glu Met Gln Ser Ser
1               5                   10                  15

<210> SEQ ID NO 213
<211> LENGTH: 17
<212> TYPE: PRT
<213> ORGANISM: Unknown

<220> FEATURE:
<223> OTHER INFORMATION: Viral immunosuppression sequence

<400> SEQUENCE: 213

Gln His Met Glu Leu Leu Glu Ser Ser Val Ile Pro Leu Val His Pro
1 5 10 15

Leu

<210> SEQ ID NO 214
<211> LENGTH: 25
<212> TYPE: PRT
<213> ORGANISM: Unknown
<220> FEATURE:
<223> OTHER INFORMATION: Viral immunosuppression sequence

<400> SEQUENCE: 214

Gly Leu Phe Gly Ala Ile Ala Gly Phe Ile Glu Asn Gly Trp Glu Gly
1 5 10 15

Cys Gly Gly Glu Lys Glu Lys Glu Lys
20 25

<210> SEQ ID NO 215
<211> LENGTH: 24
<212> TYPE: PRT
<213> ORGANISM: Unknown
<220> FEATURE:
<223> OTHER INFORMATION: Viral immunosuppression sequence

<400> SEQUENCE: 215

Gly Leu Phe Gly Ala Ala Gly Phe Ile Glu Asn Gly Trp Glu Gly Cys
1 5 10 15

Gly Gly Glu Lys Glu Lys Glu Lys
20

<210> SEQ ID NO 216
<211> LENGTH: 22
<212> TYPE: PRT
<213> ORGANISM: Unknown
<220> FEATURE:
<223> OTHER INFORMATION: Viral immunosuppression sequence

<400> SEQUENCE: 216

Gly Leu Phe Ala Gly Phe Ile Glu Asn Gly Trp Glu Gly Cys Gly Gly
1 5 10 15

Glu Lys Glu Lys Glu Lys
20

<210> SEQ ID NO 217
<211> LENGTH: 27
<212> TYPE: PRT
<213> ORGANISM: Unknown
<220> FEATURE:
<223> OTHER INFORMATION: Viral immunosuppression sequence

<400> SEQUENCE: 217

Pro Ala Leu Ser Thr Gly Leu Ile His Leu His Gln Asn Ile Val Asp
1 5 10 15

Val Gln Cys Gly Gly Glu Lys Glu Lys Glu Lys
20 25

<210> SEQ ID NO 218
<211> LENGTH: 28
<212> TYPE: PRT
<213> ORGANISM: Unknown

-continued

```
<220> FEATURE:
<223> OTHER INFORMATION: Viral immunosuppression sequence

<400> SEQUENCE: 218

Gly Asp Thr Ala Trp Asp Phe Gly Ser Ile Gly Gly Val Phe Thr Ser
1               5                   10                  15

Val Gly Lys Cys Gly Gly Glu Lys Glu Lys Glu Lys
            20                  25
```

IDENTIFICATION AND ATTENUATION OF THE IMMUNOSUPPRESSIVE DOMAINS IN FUSION PROTEINS OF ENVELOPED RNA VIRUSES

The present invention relates to enveloped RNA viruses. In particular, the invention relates to the generation of superior antigens for mounting an immune response by first identifying then mutating the immunosuppressive domains in fusion proteins of enveloped RNA viruses resulting in decreased immunosuppressive properties of viral envelope proteins from said viruses.

TECHNICAL BACKGROUND

Classification of Viruses

ICTV Classification

The International Committee on Taxonomy of Viruses (ICTV) developed the current classification system and wrote guidelines that put a greater weight on certain virus properties to maintain family uniformity. A unified taxonomy (a universal system for classifying viruses) has been established. The 7th ICTV Report formalized for the first time the concept of the virus species as the lowest taxon (group) in a branching hierarchy of viral taxa. However, at present only a small part of the total diversity of viruses has been studied, with analyses of samples from humans finding that about 20% of the virus sequences recovered have not been seen before, and samples from the environment, such as from seawater and ocean sediments, finding that the large majority of sequences are completely novel.

The general taxonomic structure is as follows:

Order (-virales)

Family (-viridae)

Subfamily (-virinae)

Genus (-virus)

Species (-virus)

In the current (2008) ICTV taxonomy, five orders have been established, the Caudovirales, Herpesvirales, Mononegavirales, Nidovirales, and Picornavirales. The committee does not formally distinguish between subspecies, strains, and isolates. In total there are 5 orders, 82 families, 11 subfamilies, 307 genera, 2,083 species and about 3,000 types yet unclassified.

Baltimore Classification

The Baltimore Classification of viruses is based on the method of viral mRNA synthesis.

The ICTV classification system is used in conjunction with the Baltimore classification system in modern virus classification.

The Baltimore classification of viruses is based on the mechanism of mRNA production. Viruses must generate mRNAs from their genomes to produce proteins and replicate themselves, but different mechanisms are used to achieve this in each virus family. Viral genomes may be single-stranded (ss) or double-stranded (ds), RNA or DNA, and may or may not use reverse transcriptase (RT). Additionally, ssRNA viruses may be either sense (+) or antisense (−). This classification places viruses into seven groups:

I: dsDNA viruses (e.g. Adenoviruses, Herpesviruses, Poxviruses)

II: ssDNA viruses (+)sense DNA (e.g. Parvoviruses)

III: dsRNA viruses (e.g. Reoviruses)

IV: (+)ssRNA viruses (+)sense RNA (e.g. Picornaviruses, Togaviruses)

V: (−)ssRNA viruses (−)sense RNA (e.g. Orthomyxoviruses, Rhabdoviruses)

VI: ssRNA-RT viruses (+)sense RNA with DNA intermediate in life-cycle (e.g. Retroviruses)

VII: dsDNA-RT viruses (e.g. Hepadnaviruses)

As an example of viral classification, the chicken pox virus, varicella zoster (VZV), belongs to the order Herpesvirales, family Herpesviridae, subfamily Alphaherpesvirinae, and genus Varicellovirus. VZV is in Group I of the Baltimore Classification because it is a dsDNA virus that does not use reverse transcriptase.

Many viruses (e.g. influenza and many animal viruses) have viral envelopes covering their protein cores. The envelopes typically are derived from portions of the host cell membranes (phospholipids and proteins), but include some viral glycoproteins. Functionally, viral envelopes are used to enable viruses to enter host cells. Glycoproteins on the surface of the envelope serve to identify and bind to receptor sites on the host's membrane. Subsequently the viral envelope then fuses with that of the host's, allowing the viral capsid and viral genome to enter and infect the host.

Typically, in RNA viruses a single transmembrane glycoprotein, a fusion protein, undergoes a conformational transition triggered by receptor recognition or low pH, leading to the insertion of a fusion peptide into the plasma membrane or the membrane of an endocytic vesicle. For some RNA viruses, including members of the paramyxovirus family, separate envelope proteins mediate attachment and fusion.

Membrane fusion can occur either at the plasma membrane or at an intracellular location following internalization of virus by receptor-mediated endocytosis. Fusion is mediated by viral transmembrane proteins known as fusion proteins. Upon appropriate triggering, the fusion protein interacts with the target membrane through a hydrophobic fusion peptide and undergoes a conformational change that drives the membrane fusion reaction. There are a variety of fusion triggers, including various combinations of receptor binding, receptor/coreceptor binding, and exposure to the mildly acidic pH within the endocytic pathway. Fusion proteins from different viruses have different names in spite of the common functionality.

Based on important structural features, many virus membrane fusion proteins are currently annotated to either the "class I" membrane fusion proteins exemplified by the influenza hemagglutinin (HA) or HIV-1 gp41, or the "class II" proteins of the alphaviruses and flaviviruses. The alphaviruses and flaviviruses are members of the Togaviridae and Flaviviridae families, respectively. These small enveloped positive-sense RNAviruses are composed of a capsid protein that assembles with the RNA into the nucleocapsid, and a lipid bilayer containing the viral transmembrane (TM) proteins.

Class I fusion proteins are synthesized as single chain precursors, which then assemble into trimers. The polypeptides are then cleaved by host proteases, which is an essential step in rendering the proteins fusion competent. This proteolytic event occurs late in the biosynthetic process because the fusion proteins, once cleaved are metastable and readily activated. Once activated, the protein refolds into a highly stable conformation. The timing of this latter event is of crucial importance in the fusion process. Maintenance of the intact precursor polypeptide during folding and assembly of the oligomeric structure is essential if the free energy that is released during the refolding event is to be available to overcome the inherent barriers to membrane fusion. The new amino-terminal region that is created by the cleavage event contains a hydrophobic sequence, which is known as the fusion peptide. The authentic carboxy-terminal region of the precursor polypeptide contains the transmembrane anchor. In the carboxy-terminal polypeptide, there are sequences known as the heptad repeat that are predicted to have an alpha helical structure and to form a coiled coil structure. These sequences participate in the formation of highly stable structure that characterizes the post-fusion conformation of the fusion protein.

The class II fusion proteins are elongated finger-like molecules with three globular domains composed almost entirely of R-sheets. Domain I is a ß-barrel that contains the N-terminus and two long insertions that connect adjacent ß-strands and together form the elongated domain II. The first of these insertions contains the highly conserved fusion peptide loop at its tip, connecting the c and d ß-strands of domain II (termed the cd loop) and containing 4 conserved disulfide bonds including several that are located at the base of the fusion loop. The second insertion contains the ij loop at its tip, adjacent to the fusion loop, and one conserved disulfide bond at its base. A hinge region is located between domains I and II. A short linker region connects domain I to domain III, a ß-barrel with an immunoglobulin-like fold stabilized by three conserved disulfide bonds. In the full-length molecule, domain III is followed by a stem region that connects the protein to the virus TM anchor. Fitting of the structure of alphavirus E1 to cryo-electron microscopy reconstructions of the virus particle reveals that E1 is located almost parallel to the virus membrane, and that E1-E1 interactions form the an icosahedral lattice.

Immunosuppressive Properties of Enveloped Viruses with Type I Fusion Proteins

Fusion proteins of a subset of enveloped Type I [1] viruses (retrovirus, lentivirus and filoviruses) have previously been shown to feature an immune suppressive activity. Inactivated retroviruses are able to inhibit proliferation of immune cells upon stimulation [2-4]. Expression of these proteins is enough to enable allogenic cells to grow to a tumor in immune competent mice. In one study, introduction of ENV expressing construct into MCA205 murine tumor cells, which do not proliferate upon s.c. injection into an allogeneic host, or into CL8.1 murine tumor cells (which overexpress class I antigens and are rejected in a syngeneic host) resulted in tumor growth in both cases [5]. Such immunosuppressive domains have been found in a variety of different viruses with type 1 fusion mechanism such as gammaretroviruses like Mason pfeizer monkey virus (MPMV) and murine leukemia virus (MLV), lentiviruses such as HIV and in filoviruses such as Ebola and Marburg viruses [6-9].

This immune suppressive activity was in all cases located to a very well-defined structure within the class I fusion proteins, more precisely at the bend in the heptad repeat just N-terminale of the transmembrane structure in the fusion protein. The immunosuppressive effects range from significant inhibition of lymphocyte proliferation [7,8], cytokine skewing (up regulating IL-10; down regulating TNF-$\alpha$, IL-12, IFN-$\gamma$) [10] and inhibition of monocytic burst [11] to cytotoxic T cell killing [12]. Importantly, peptides spanning ISD in these assays must either be linked as dimers or coupled to a carrier (i.e. >monomeric) to be active. Such peptides derived from immune-suppressive domains are able to reduce or abolish immune responses such as cytokine secretion or proliferation of T-cells upon stimulation. The protection mediated by the immunosuppressive properties of the fusion protein from the immune system of the host is not limited to the fusion protein but covers all the viral envelope proteins displayed at viral or cellular membranes in particular also the protein mediating attachment of the virus to the cell.

Co-Location of the Immunosuppression Domain and the Fusion Domain

The immunosuppressive domain of retro-, lenti- and filoviruses overlap a structurally important part of the fusion subunits of the envelope proteins. Although the primary structure (sequence) of this part of the fusion proteins can vary greatly from virus to virus, the secondary structure, which is very well preserved among different virus families, is that of an alpha helix that bends in different ways during the fusion process This structure plays a crucial role during events that result in fusion of viral and cellular membranes. It is evident that the immunosuppressive domains of these (retroviral, lentiviral and filoviral) class I fusion proteins overlap with a very important protein structure needed for the fusion proteins mechanistic function.

The energy needed for mediating the fusion of viral and cellular membranes is stored in the fusion proteins, which are thus found in a meta-stable conformation on the viral surface. Once the energy is released to drive the fusion event, the protein will find its most energetically stable conformation. In this regard fusion proteins can be compared with loaded springs that are ready to be sprung. This high energy conformation makes the viral fusion proteins very susceptible to modifications; Small changes in the primary structure of the protein often result in the protein to be folded in its stable post fusion conformation. The two conformations present very different tertiary structures of the same protein.

It has been shown in the case of simple retroviruses that small structural changes in the envelope protein are sufficient to remove the immune suppressive effect without changing structure and hence the antigenic profile.

The mutated non-immune suppressive envelope proteins are much better antigens for vaccination. The proteins can induce a 30-fold enhancement of anti-env antibody titers when used for vaccination and are much better at launching an effective CTL response [6]. Furthermore, viruses that contain the non-immunosuppressive form of the friend murine leukemia virus envelope protein, although fully infectious in irradiated immunocompromised mice cannot establish an infection in immunocompetent animals. Interestingly in the latter group the non-immunosuppressive viruses induce both a higher cellular and humeral immune response, which fully protect the animals from subsequent challenge by wild type viruses [13].

Immunosuppressive domains in the fusion proteins (viral envelope proteins) from Retroviruses, lentiviruses and Filoviruses have been known since 1985 for retrovirus [7], since 1988 for lentivirus [8] and since 1992 for filoviruses [14]. These viruses, as mentioned above, all belong to enveloped RNA viruses with a type I fusion mechanism. The immunosuppressive domains of lentivirus, retroviruses and filoviruses show large structural similarity. Furthermore the immunosuppressive domain of these viruses are all located at the same position in the structure of the fusion protein, more precisely in the linker between the two heptad repeat structures just N-terminal of the transmembrane domain in the fusion protein. These heptad repeat regions constitute two alpha helices that play a critical role in the active mechanism of membrane fusion by these proteins. The immune suppressive domains can be located in relation to two well conserved cystein residues that are found in these structures. These cystein residues are between 4 and 6 amino acid residues from one another and in many cases are believed to form disulfide bridges that stabilize the fusion proteins. The immune suppressive domains in all three cases include at least some of the first 22 amino acids that are located N-terminal to the first cysteine residue. Recently the immunosuppressive domains in the fusion protein of these viruses have been successfully altered in such a way that the fusogenic properties of the fusion protein have been preserved. Such mutated fusion proteins with decreased immunosuppressive properties have been shown to be superior antigens for vaccination purposes [13].

SUMMARY OF THE INVENTION

The inventors have been able to devise methods for the identification of new immunosuppressive domains or potentially immunosuppressive domains located in proteins displayed at the surface of enveloped RNA viruses. The inventors of the present invention have surprisingly found immunosuppressive domains or potentially immunosuppressive domains in fusion proteins in a large number of other enveloped RNA viruses in addition to lentivirus, retrovirus and filovirus, where such immunosuppressive domains had not been described previously. In addition, the inventors have been able to develop methods for mutating said immunosuppressive domains in order to reduce the immunosuppressive properties of viral surface proteins, which are useful for providing strategies for producing new vaccines with improved properties by making superior antigens, or for generation of neutralizing antibodies. Through such approaches, the inventors have been able to propose vaccination regimes against different types of viruses such as e.g. Hepatitis C, Dengue virus and Influenza where effective vaccination regimes have been in great demand for many years. This may allow the production of vaccines against virus for which no vaccines has been known e.g. hepatitis C and Dengue, as well as improved versions of known vaccines, e.g. for Influenza.

According to an aspect, the inventors propose the use of up to four parameters for the identification of immunosuppressive domain in enveloped RNA viruses with hitherto un-described immunosuppressive properties. Proposed parameters used as part of a strategy for identifying a peptide sequence or a peptide which likely acts as immunosuppressive domains may comprise one or more of the following parameters (preferably all parameters are used):

1): The peptide is preferably located in the fusion protein of enveloped RNA viruses;

2): The peptide is preferably capable of interacting with membranes;

3): Preferably a high degree of homology in the primary structure (sequence) of the peptide of said domain exists either within the Order, Family, Subfamily, Genus, or Species of viruses. This feature is due to the immunosuppressive domain being under a dual selection pressures, one as an immunosuppressive entity ensuring protection of the viral particle from the host immune system, another as a peptide interacting with membranes;

4): The position at the surface of the fusion protein at a given conformation is preferably a feature of immunosuppressive domains. This can be revealed either by position in a 3D structure or by antibody staining of cells expressing the fusion protein or on viral surfaces displaying the fusion protein.

Based upon these parameters the inventors have inter alia identified three new groups of enveloped RNA viruses with immunosuppressive domains in their fusion protein:

1: The inventors have identified immunosuppressive domains among enveloped RNA viruses with type II fusion mechanism. Hitherto, immunosuppressive domains have not been described for any enveloped RNA viruses with a type II fusion mechanism. Immunosuppressive domains have been identified by the inventors at two positions in two different groups of viruses:

i. Co-localizing with the fusion peptide exemplified by the identification of an common immunosuppressive domain in the fusion peptide of Flavirius (Dengue virus, west Nile virus etc), and ii. In the hydrophobic alpha helix N-terminal of the transmembrane domain in the fusion protein exemplified by the finding of an immunosuppressive domain in said helixes of all flaviridae e.g. Hepatitis C virus, Dengue, west nile etc.

2: The inventors have identified immunosuppressive domains in the fusion protein among enveloped RNA viruses with type I fusion mechanism (excluding lentivirus, retrovirus and filovirus). This position co-localizes with the fusion peptide of said fusion protein as demonstrated by the identification of a common immunosuppressive domain in the fusion peptide of all Influenza A and B types.

3: The inventors have identified potential immunosuppressive domains located at various positions of type I enveloped RNA viruses (excluding lentivirus, retrovirus and filovirus) as well as in enveloped RNA viruses featuring a fusion protein with neither a type I nor a type II fusion structure.

After identification of the immunosuppressive domains these must be mutated in order to decrease or completely abrogate the immunosuppressive properties of the whole envelope protein (preferably both the attachment and fusion part of the envelope protein if these are separate proteins). Such viral envelope proteins with reduced immunosuppressive properties are ideal candidates for use as antigens in vaccine compositions or for the production of neutralizing antibodies.

According to an aspect, the invention concerns a method for identifying an immunosuppressive domain of an enveloped RNA virus containing a lipid membrane, said method comprising the following steps:

a. Identifying the fusion protein of said virus;
b. Identifying at least one well conserved domain preferably among the membrane associated domains of said fusion protein (where the immunosuppressive domain is preferably located at the surface of the protein in one or more of the different conformations of the fusion protein undergoing fusion);
c. Optionally multimerizing or dimerizing said peptide; and
d. Confirming the immunosuppressive activity of at least one optionally multimerized or dimerized peptide by testing said optionally dimerized or multimerized peptide for immunosuppressive activity.

Concerning step a., fusion proteins or putative fusion proteins are usually identified by searching scientific databases, e.g. such as searching NCBI taxonomy database (ncbi.nlm.nih.gov/Taxonomy/) and selecting proteins of the Family, Subfamily, Genus or Species to be investigated and subsequently searching these for fusion, or the specific fusion protein, such as the protein listed in Table 1 below.

Concerning step b., vira are divided according to the following classification: Order (-virales), Family (-viridae), Subfamily (-virinae), Genus (-virus), Species (-virus). In order to localize conserved regions in the fusion proteins one or a few candidates from all viruses within an order are aligned first using an alignment tool such as the cobalt alignment tool (ncbi.nlm.nih.gov/tools/cobalt/). If stretches of conserved amino acids, such as ranging from 6 to 30 amino acids long, can be identified these are considered as candidates for immunosuppressive regions and are subjected to further investigation. If no candidates are found in an order, the same procedure is applied to the family of viruses. If still no candidates are found by testing different viruses belonging to a family of viruses we move on to the subfamily of viruses. If we cannot localize regions of homology among the subfamily we then test viruses from a genus and if we still cannot localize regions of homology we ultimately align as many possible individual viral sequences from a single species of virus (up to 1400 individual viral sequences). In general regions of homology are identified by having at least 25%, more preferred at least 30%, preferably at least 40%, more preferred at least 50%, more preferred at least 60%, preferably at least 70%, and even more preferably at least 75% homology (i.e. sequence identity) within a given region.

Concerning step c., the dimerized peptide could be synthetic, the multimerized peptide could be displayed as dimerized or trimerized fusion proteins either displayed alone or on membranes such as a viral particle. Alternatively the multimerized peptides can be coupled to a carrier protein.

According to another aspect, the invention concerns a method for decreasing or completely abrogating the immunosuppressive properties of an immunosuppressive domain of a fusion protein of an enveloped RNA virus containing a lipid membrane, said method comprising the steps of:

e. Mutating an immunosuppressive domain to produce at least one, preferably a plurality of mutated peptides
f. Optionally dimerizing or multimerizing said at least one, preferably plurality of mutated peptides;
g. Selecting at least one of said, preferably a plurality of said mutated peptides by testing for reduced immunosuppressive properties, preferably as shown by at least 25% reduction as compared to a wildtype peptide mono-, di- or multimer corresponding to the multimerization status of said mutated peptides;
h. Mutating a fusion protein of an enveloped RNA virus containing a lipid membrane to contain said selected mutated peptide having reduced immunosuppressive properties;
i. Confirming expression by testing the whole viral envelope protein encompassing said mutated fusion protein for capability of being expressed by at least one of cellular or viral surfaces.

According to an aspect, the invention concerns a method, further comprising the step of:

j. Using said viral envelope protein encompassing said mutated fusion protein with reduced immunosuppressive properties as an antigen for generation of an enhanced immune response.

A number of strategies are proposed for knock-out (i.e. decreasing or completely abrogating) of the immunosuppressive domain, these strategies comprise, but are not limited to, mutating or modifying the immunosuppressive domain into having the sequence of a mutant. A knock-out may be achieved e.g. by mutation, deletion or insertion in an immunosuppressive domain. A mutation may be at least one exchange of an amino acid with another amino acid, at least one insertion, at least one deletion, or a combination of one or more of these.

Mutants decreasing or completely abrogating the immunosuppressive properties will be identified by performing a complete or partly scanning of said immunosuppressive peptide with either Isoleucine, Alanine Leucine, Asparagine, Lysine, Aspartic acid, Methionine, Cysteine, Phenylalanine, Glutamic acid, Threonine, Glutamine, Tryptophan, Glycine, Valine, Proline, Serine, Tyrosine, Arginine, Histidine, insertions, deletions or point mutations. Alternatively the literature will be searched for mutations in said regions where said mutation did not eliminate expression of the fusion protein on the surface of the cell or viral envelope. Dimerized versions of said mutants may be tested in a cell proliferation assay. The literature provides further details (as an example see Cross K J, Wharton S A, Skehel J J, Wiley D C, Steinhauer D A. Studies on influenza haemagglutinin fusion peptide mutants generated by reverse genetics. EMBO J. 2001 Aug. 15; 20(16):4432-42).

According to an aspect, the invention concerns a method for identifying an immunosuppressive domain in the fusion protein of an enveloped RNA virus having a lipid membrane, said method comprising:

a. Identifying at least one well conserved domain among the group consisting of the membrane associated domains of the fusion protein and the surface associated domains of the fusion protein;
b. Providing at least one peptide with the sequence of said identified at least one well conserved domain;
c. Optionally dimerizing or multimerizing said at least one peptide; and
d. Confirming the immunosuppressive activity of said at least one optionally dimerized or multimerized peptide by testing said at least one optionally dimerized or multimerized peptide for immunosuppressive activity.

According to another aspect, the invention concerns an immunosuppressive domain identified according to the invention.

According to another aspect, the invention concerns an immunosuppressive domain selected among the sequences of Table 1 and Seq. Id. 1-200.

According to an aspect, the invention concerns a method for decreasing or completely abrogating the immunosuppressive properties of an immunosuppressive domain of the fusion protein of an enveloped RNA virus having a lipid membrane, said method comprising the steps of:

e. Mutating an immunosuppressive domain to provide at least one mutated peptide;
f. Optionally dimerizing or multimerizing said at least one mutated peptide;
g. Selecting one of said optionally dimerized or multimerized mutated peptides showing reduced immunosuppressive properties;
h. Mutating the fusion protein of the enveloped RNA virus to contain said selected mutated peptide having reduced immunosuppressive properties;
i. Confirming expression by testing the viral envelope protein encompassing said mutated fusion protein for capability of being expressed by at least one of cellular or viral surfaces.

According to an aspect, the invention concerns a mutated peptide providing reduced immunosuppressive properties, said mutated peptide having a sequence according to Table 1 or any of Seq. Id. 201-203 or obtainable as said selected mutated peptide of the method according to the invention.

According to an aspect, the invention concerns a method for generating an enhanced immune response further comprising the step of:

j. Using said viral envelope protein encompassing said mutated fusion protein with reduced immunosuppressive properties as an antigen for generation of an enhanced immune response.

According to an aspect, the invention concerns a method for making an envelope protein having diminished immunosuppressive activity, comprising: Mutating or modifying an immunosuppressive domain, identifiable according to the invention, of an enveloped RNA virus with a lipid membrane surrounding the core, to include a peptide obtainable according to the invention.

According to an aspect, the invention concerns an envelope protein obtainable according to the invention.

According to an aspect, the invention concerns a mutated envelope protein obtainable according to the invention.

According to an aspect, the invention concerns a viral fusion protein from an enveloped RNA virus with reduced immunosuppressive properties, said fusion protein encompassing a mutated peptide, said mutated peptide displaying reduced immunosuppression, and said mutated peptide replacing an un-mutated wildtype peptide having a sequence of an ISU of Table 1 or is selected among Seq. Id. 1-200.

According to an aspect, the invention concerns an envelope protein comprising a mutated peptide according to the invention, said mutated fusion protein being displayed on the surface of cells wherein said mutated fusion protein is expressed.

According to an aspect, the invention concerns an enveloped RNA virus, different from a viruses selected among the group consisting of Retrovirus, Lentivirus and Filovirus, wherein an immunosuppressive domain has been modified or mutated to decrease or completely abrogate the immunosuppressive properties of an immunosuppressive domain of the fusion protein.

According to an aspect, the invention concerns a virus selected among the vira of Table 1, wherein an immunosuppressive domain has been modified or mutated to decrease or completely abrogate the immunosuppressive properties of an immunosuppressive domain of the fusion protein.

According to an aspect, the invention concerns an antigen obtainable by selecting a part of a mutated envelope protein according to the invention, said part comprising the mutated domain of said envelope protein.

According to an aspect, the invention concerns a nucleic acid sequence, preferably recombinant, encoding a mutated envelope protein, an envelope polypeptide or an antigen according to the invention.

According to an aspect, the invention concerns an isolated eukaryotic expression vector comprising a nucleic acid sequence according to the invention.

According to an aspect, the invention concerns a method for producing an antibody, said method comprising the steps of: Administering an entity selected among a mutated envelope, an envelope polypeptide, an antigen, a nucleic acid sequence or a vector according to the invention to a host, such as an animal; and obtaining the antibody from said host.

According to an aspect, the invention concerns an antibody obtainable according to the invention.

According to an aspect, the invention concerns neutralizing antibodies obtained or identified by the use of at least one envelope protein according to the invention.

According to an aspect, the invention concerns a method for manufacturing neutralizing antibodies comprising the use of at least one protein according to the invention.

According to an aspect, the invention concerns a method for manufacturing humanized neutralizing antibodies, comprising the use of at least one sequence selected among the sequences of Table 1 and sequences 201 to 203.

According to an aspect, the invention concerns a vaccine comprising a virus according to the invention.

According to an aspect, the invention concerns a vaccine composition comprising an envelope protein according to the invention.

According to an aspect, the invention concerns a vaccine composition comprising an entity selected among the group consisting of a mutated envelope protein, an envelope polypeptide, an antigen, a nucleic acid sequence, a vector and an antibody according to the invention, and in addition at least one excipient, carrier or diluent.

According to an aspect, the invention concerns a medical composition comprising antibodies raised using a virus according to the invention.

According to an aspect, the invention concerns a pharmaceutical composition comprising a mutated peptide, an envelope protein, a mutated envelope protein, an antigen, a nucleic acid sequence, a vector, an antibody or a vaccine composition according to the invention, and at least one pharmaceutically acceptable excipient, diluents or carrier.

According to an aspect, the invention concerns a use of a mutated peptide, an envelope protein, a mutated envelope protein, an antigen, a nucleic acid sequence, a vector or an antibody according to the invention, for a medical purpose, such as for the treatment, amelioration or prevention of a clinical condition, and/or such as for the manufacture of a medicament for the treatment, amelioration or prevention of a clinical condition.

According to an aspect, the invention concerns a method of treating or ameliorating the symptoms of an individual, or prophylactic treating an individual, comprising administering an amount of mutated peptide, an envelope protein, a mutated envelope protein, antigen, nucleic acid sequence, vector or vaccine composition according to the invention.

DETAILED DISCLOSURE

Table 1 provides a list of viruses and their immunosuppressive domain(s). Asterix denotes extremely conserved sequence in the immunosuppressive domain for a given class, group, family or species of viruses. New immunosuppressive domains identified and tested in CTLL-2 assay for a given class, group, family or species of viruses are listed. Both the columns with “Putative ISU as described in this application for identification of immunosuppressive domains” and “Peptides from domains from fusion proteins exhibiting immunosuppressive activity (ISU)” are candidates for domains which are immunosuppressive. Note that all of the entries of the latter column, were originally identified by the inventors as a member of the former column. Due to the redundancy, the entries of the latter column were not included in the former column.

1: The inventors have identified immunosuppressive domains in the fusion proteins among enveloped RNA viruses with a type II fusion mechanism. Insofar immunosuppressive domains have not been previously described for type II enveloped RNA viruses. The immunosuppressive domain has been identified at two positions in the fusion protein in two different groups of viruses A: Co-localizing with the fusion peptide exemplified by the identification of an common immunosuppressive domain in the fusion peptide of Flavirus (Dengue virus, westNile virus etc.) and B: in the hydrophobic alpha helix N-terminal of the transmembrane domain in the fusion protein exemplified by the finding of an immunosuppressive domain in said helixes of Flaviridae e.g. Hepatitis C virus, Dengue, WestNile virus etc, cf. Table 1.

2: The inventors have identified immunosuppressive domains in the fusion protein among enveloped RNA viruses with type I fusion mechanism (excluding lentivirus, retrovirus and filovirus). This new position co-localizes with the fusion peptide of said fusion protein as demonstrated by the identification of a common immunosuppressive domain in the fusion peptide of all Influenza A and B types, cf. Table 1.

3: The inventors have identified potential immunosuppressive domains located at various positions of type I enveloped RNA viruses (excluding lentivirus, retrovirus and filovirus) and enveloped RNA viruses with neither Type I nor type II fusion mechanism, cf. Table 1.

TABLE 1

| Family | Genus | Species (group) | Species (Strain) | Putative ISU as identified using the criteria described in this application for identification of immunosuppressive domains |
|---|---|---|---|---|
| Flavi-viridae | Flavi-virus | Aroa virus | Bussuquara virus<br>guape virus<br>Naranjal virus | SEQ ID NO: 85<br>NRGWNNGCGLFGKG<br>**************<br>SEQ ID NO: 7<br>GDAAWDFGSVGGVFNSLGK<br>**○****○*****○○*○** |
| | | Dengue virus | Dengue 1 | SEQ ID NO: 8<br>GGTAWDFGSIGGVFTSVGK<br>*○***************** |
| | | | Dengue 2 | SEQ ID NO: 9<br>GDTAWDFGSLGGVFTSVGK<br>****************○**<br>SEQ ID NO: 173<br>KGSSIGKMFEATARGARRMAILG |
| | | | Dengue 3 | SEQ ID NO: 174<br>KGSSIGQMFETTMRGAKRMAILG |
| | | | Dengue 4 | SEQ ID NO: 10<br>GETAWDFGSVGGLLTSLGK<br>************○○*****<br>SEQ ID NO: 173<br>KGSSIGKMFEATARGARRMAILG |
| | | Japanese encephalitis virus group | Japanese encephalitis virus | SEQ ID NO: 11<br>LGDTAWDFGSIGGVFNSIG<br>***○*************** |
| | | | Koutango virus | SEQ ID NO: 12<br>LGDTAWDFGSVGGIFTSLG |
| | | | Murray Valley encephalitis Virus | SEQ ID NO: 13<br>LGDTAWDFGSVGGVFNSIG |
| | | | St. Louis encephalitis virus | SEQ ID NO: 11<br>LGDTAWDFGSIGGVFNSIG<br>******************* |
| | | | Usutu virus | SEQ ID NO: 14<br>LGDTAWDFGSVGGIFNSVG<br>******************* |
| | | | West Nile virus | SEQ ID NO: 15<br>LGDTAWDFGSVGGVFTSVG<br>**********○******** |
| | | Kokobera virus group | Kokobera Virus unclassified Kokobera virus group | SEQ ID NO: 16<br>IGDDAWDFGSVGGILNSVG |
| | | Modoc Virus group | Modoc Virus | SEQ ID NO: 17<br>VGSAFWNSDQRFSAINLMD<br>SEQ ID NO: 18<br>DRGWGNGCALFGKG |

TABLE 1-continued

| | | |
|---|---|---|
| | Cowbone Ridge virus | |
| | Jutiapa virus | |
| | Sal Vieja virus | |
| | San Perlita virus | |
| mosquito-borne viruses | Ilheus virus | SEQ ID NO: 84<br>LGDTAWDFGSVGGIFNSIG |
| | Sepik virus | SEQ ID NO: 19<br>TGEHSWDFGSTGGFFASVG |
| Ntaya virus group | Bagaza virus | SEQ ID NO: 20<br>LGDTAWDFGSVGGFFTSLG |
| | Tembusu virus | SEQ ID NO: 83<br>LGDTAWDFGSVGGVLTSIG |
| | Yokose virus | SEQ ID NO: 21<br>IGDDAWDFGSTGGIFNTIG |
| Rio Bravo virus group | Apoi virus | SEQ ID NO: 22<br>SSAFWNSDEPFHFSNLISII |
| | Entebbe bat virus | SEQ ID NO: 23<br>GDDAWDFGSTGGIFNTIGKA |
| | Rio Bravo virus | SEQ ID NO: 24<br>SSAYWSSSEPFTSAGIMRIL |
| | Saboya virus | SEQ ID NO: 18<br>DRGWGNGCALFGKG<br>SEQ ID NO: 25<br>GSSSWDFSSAGGFFGSIGKA |
| Seaborne tick-borne virus group | Meaban virus | SEQ ID NO: 26<br>GDAAWDFGSVGGFMTSIGRA<br>SEQ ID NO: 27<br>DRGWGNHCGLFGKG |
| | Saumarez Reef virus | SEQ ID NO: 28<br>GETAWDFGSAGGFFTSVGRG<br>SEQ ID NO: 27<br>DRGWGNHCGLFGKG |
| | Tyuleniy virus | SEQ ID NO: 29<br>GEAAWDFGSAGGFFQSVGRG<br>SEQ ID NO: 27<br>DRGWGNHCGLFGKG |
| Spondweni virus group | Zika virus | SEQ ID NO: 30<br>LGDTAWDFGSVGGVFNSLGK<br>*************○○**○** |
| | Kyasanur forest disease virus | SEQ ID NO: 31<br>VGEHAWDFGSVGGMLSSVG<br>*************○*****<br>SEQ ID NO: 27<br>DRGWGNHCGLFGKG |
| | Langat virus | SEQ ID NO: 32<br>VLGEHAWDFGSVGGVMTSIG<br>SEQ ID NO: 27<br>DRGWGNHCGLFGKG |
| | Louping ill virus | SEQ ID NO: 33<br>IGEHAWDFGSAGGFFSSIG<br>**********○***○○*○*<br>SEQ ID NO: 27<br>DRGWGNHCGLFGKG |

TABLE 1-continued

| | | |
|---|---|---|
| | Omsk hemorrhagic fever virus | SEQ ID NO: 34<br>LGEHAWDFGSTGGFLSSIG<br>SEQ ID NO: 27<br>DRGWGNHCGLFGKG |
| | Powassan virus | SEQ ID NO: 35<br>VGEHAWDFGSVGGILSSVG<br>*************○*****<br>SEQ ID NO: 36<br>DRGWGNHCGFFGKG<br>************* |
| | Royal Farm virus | SEQ ID NO: 27<br>DRGWGNHCGLFGKG |
| | Tick-borne encephalitis virus | SEQ ID NO: 37<br>IGEHAWDFGSAGGFLSSIG<br>SEQ ID NO: 38<br>IGEHAWDFGSTGGFLTSVG<br>SEQ ID NO: 39<br>IGEHAWDFGSTGGFLASVG<br>SEQ ID NO: 27<br>DRGWGNHCGLFGKG |
| Yaounde virus | | SEQ ID NO: 40<br>LGDTAWDFGSIGGVFTSLG |
| Yellow fever virus group | Banzi virus | SEQ ID NO: 41<br>VGSSSWDFSSTSGFFSSVG |
| | Bouboui virus | SEQ ID NO: 42<br>VGRSSWDFSSAGGFFSSVG |
| | Edge Hill virus | |
| | Uganda S virus | |
| | Wesselsbron virus | |
| | Yellow fever virus | SEQ ID NO: 43<br>MGDTAWDFSSAGGFFTSVG<br>***○*************** |
| unclassified Flavivirus | Batu Cave virus | SEQ ID NO: 44 |
| | Cacipacore virus | NRGWGTGCFKWGIG |
| | Calbertado virus | SEQ ID NO: 45 |
| | Cell fusing agent virus | NRGWGTGCFEWGLG |
| | Chaoyang virus | |
| | Chimeric Tick-borne encephalitis virus/Dengue virus 4 | |
| | Culex theileri flavivirus | |
| | Donggang virus | |
| | Duck hemorrhagic ovaritis virus | |
| | Flavivirus Aedes/MO-Ac/ITA/2009 | |
| | Flavivirus Anopheles/PV-Am/ITA/2009 | |
| | Flavivirus CbaAr4001 | |
| | Flavivirus FSME | |
| | Flavivirus Phlebotomine/76/Arrabida/2007 | |
| | Gadgets Gully virus | |
| | Greek goat encephalitis virus | |
| | Jugra virus | |
| | Kadam virus | |
| | Kamiti River virus | |
| | Kedougou virus | |

TABLE 1-continued

| | | | |
|---|---|---|---|
| | | Montana myotis leukoencephalitis virus | |
| | | Mosquito flavivirus | |
| | | Ngoye virus | |
| | | Nounane virus | |
| | | Phlebotomus flavivirus Alg_F19 | |
| | | Phlebotomus flavivirus Alg_F8 | |
| | | Quang Binh virus | |
| | | Russian Spring-Summer encephalitis virus | |
| | | Sokoluk virus | |
| | | Spanish sheep encephalitis virus | |
| | | T'Ho virus | |
| | | Tai forest virus B31 | |
| | | Tamana bat virus | |
| | | Tick-borne flavivirus | |
| | | Wang Thong virus | |
| | | Flavivirus sp. | |
| | | Aedes flavivirus | SEQ ID NO: 45 |
| | | | NRGWGTGCFEWGLG |
| | | | SEQ ID NO: 46 |
| | | | HVAGRYSKHGMAGIGSVWEDLVR |
| | | Culex flavivirus | SEQ ID NO: 44 |
| | | | NRGWGTGCFKWGIG |
| | | | SEQ ID NO: 47 |
| | | | VDKYRRFGTAGVGG |
| Hepacivirus | Hepatitis C virus | Hepatitis C virus genotype 1 a | |
| | | Hepatitis C virus genotype 1b | SEQ ID NO: 48 |
| | | | GLIHLHRNIVDVQYLYG |
| | | | SEQ ID NO: 176 |
| | | | PALSTGLIHLHRNIVDVQ |
| | | Hepatitis C virus genotype 2 | SEQ ID NO: 49 |
| | | | GLIHLHQNIVDVQYMYG |
| | | | SEQ ID NO: 175 |
| | | | PALSTGLIHLHQNIVDVQ |
| | | Hepatitis C virus genotype 3 | SEQ ID NO: 175 |
| | | | PALSTGLIHLHQNIVDVQ |
| | | Hepatitis C virus genotype 4 | SEQ ID NO: 175 |
| | | | PALSTGLIHLHQNIVDVQ |
| | | Hepatitis C virus genotype 5 | SEQ ID NO: 50 |
| | | | GLIHLHQNIVDTQYLYG |
| | | | SEQ ID NO: 177 |
| | | | PALSTGLIHLHQNIVDTQ |
| | | Hepatitis C virus genotype 6 | SEQ ID NO: 175 |
| | | | PALSTGLIHLHQNIVDVQ |
| | | All Hepatitis C virus | |
| Pesti virus | Border disease | Border disease virus - | SEQ ID NO: 51 |
| | virus | Border disease virus - X818 | NTTLLNGSAFQLICPYGWVGRVEC |
| | | Border disease virus 1 | SEQ ID NO: 52 |
| | | Border disease virus 2 | SYFQQYMLKGQYQYWFDLE |
| | | Border disease virus 3 | |
| | | Border disease virus isolates | |
| | Bovine viral | Bovine viral diarrhea virus 1-CP7 | SEQ ID NO: 53 |
| | diarrhea virus 1 | Bovine viral diarrhea virus 1-NADL | NTTLLNGPAFQMVCPLGWTGTVSC |
| | | Bovine viral diarrhea virus 1-Osloss | SEQ ID NO: 54 |

TABLE 1-continued

| | | | | |
|---|---|---|---|---|
| | | | Bovine viral diarrhea virus 1-SD1 | SYFQQYMLKGEYQYWFDLE |
| | | | Bovine viral diarrhea virus isolates and | |
| | | | strains | |
| | | | Bovine viral diarrhea virus type 1a | |
| | | | Bovine viral diarrhea virus type 1b | |
| | | | Pestivirus isolate 97-360 | |
| | | | Pestivirus isolate Hay 87/2210 | |
| | | | Pestivirus strain mousedeer | |
| | | | Pestivirus type 1 isolates | |
| | | Bovine viral | Bovine viral diarrhea virus 2 | SEQ ID NO: 55 |
| | | diarrhea virus 2 | Pestivirus sp. strain 178003 | SLLNGPAFQMVCPQGWTGTIEC |
| | | (BVDV-2) | Pestivirus sp. strain 5250Giessen-3 | SEQ ID NO: 56 |
| | | | Bovine viral diarrhea virus-2 isolate | DRYFQQYMLKGKWQYWFDLD |
| | | | SCP | |
| | | Classical swine | Classical swine fever virus | SEQ ID NO: 57 |
| | | fever virus | Hog cholera virus strain Zoelen | TLLNGSAFYLVCPIGWTGVIEC |
| | | | | SEQ ID NO: 58 |
| | | | | SYFQQYMLKGEYQYWFDLD |
| | | unclassified | Bovine viral diarrhea virus 3 | SEQ ID NO: 59 |
| | | Pestivirus | | SEQ ID NO: 82 |
| | | | | TLLNGPAFQLVCPYGWTGTIEC |
| | | | | SEQ ID NO: 60 |
| | | | | DNYFQQYMLKGKYQYWFDLEATD |
| | | | Chamois pestivirus 1 | SEQ ID NO: 61 |
| | | | | TLLNGSAFQMVCPFGWTGQVEC |
| | | | | SEQ ID NO: 62 |
| | | | | DSYFQQYMLKGEYQYWFDLDAKD |
| | | | Porcine pestivirus isolate Bungowannah | SEQ ID NO: 205 |
| | | | | TLLNGPAFQLVCPYGWTGTIECDSYYQ |
| | | | | SEQ ID NO: 206 |
| | | | | QYIIKSGYQYWFDLTAKD |
| | Unnclassified | | Barkedji virus | |
| | Flaviviridae | | Canine hepacivirus AAK-2011 | |
| | | | GB virus A | |
| | | | Douroucouli hepatitis GB virus A | |
| | | | GBV-A-like agents | |
| | | | GB virus D | |
| | | | GBV-C/HGV group | |
| | | | GB virus C | |
| | | | Hepatitis GB virus C-like virus | |
| | | | Hepatitis GB virus B | |
| | | | Lammi virus | |
| | | | Marmoset hepatitis GB virus A | |
| | | | Nakiwogo virus | |
| | | | Turkey meningoencephalitis virus | |
| Togaviridae | Alpha-virus | Aura virus | | SEQ ID NO: 63 |
| | | Barmah Forest | | GVYPFMWGGAYCFCDTENTQVS |
| | | virus | | **********○****○**○*○* |
| | | Middelburg virus | | SEQ ID NO: 64 |
| | | Ndumu virus | | APFGCEIYTNPIRAENCAVGSIP |
| | | Salmon pancreas | | *****○*○○○*○**○○*○○*○○* |
| | | disease virus | | SEQ ID NO: 65 |

TABLE 1-continued

| | | | |
|---|---|---|---|
| | Getah virus | | SDFGGIATVKYSASKSGKCAVH |
| | Mayaro virus | | ○***○○○○○○*○○○○○*○*○○* |
| | Trocara virus | | SEQ ID NO: 66 |
| | EEEV complex | | FSTANIHPEFRLQICTSYVTCKGDCHPP |
| | WEEV complex | Fort Morgan virus | *○○○○○○○○*○○○○*○○○○○*○○○*○** |
| | | Highlands J virus | |
| | | Sindbis virus | |
| | | Western equine encephalomyelitis virus | |
| | | Whataroa virus | |
| | VEEV complex | Cabassou virus | |
| | | Mucambo virus | |
| | | Pixuna virus | |
| | | Venezuelan equine encephalitis virus | SEQ ID NO: 67 |
| | | | GVYPFMWGGAYCFCD |
| | | | *************** |
| | | | SEQ ID NO: 68 |
| | | | GDCHPPKDHIVTHPQYHAQ |
| | | | ************○**○*○* |
| | | | SEQ ID NO: 69 |
| | | | AVSKTAWTWLTS |
| | | | *********○○* |
| | SFV complex | Bebaru virus | SEQ ID NO: 63 |
| | | O'nyong-nyong virus | GVYPFMWGGAYCFCDTENTQVS |
| | | Ross River virus | **********○****○**○*○* |
| | | Semliki forest virus | SEQ ID NO: 64 |
| | | Una virus | APFGCEIYTNPIRAENCAVGSIP |
| | | | *****○*○○○*○**○○*○○*○○* |
| | | | SEQ ID NO: 65 |
| | | | SDFGGIATVKYSASKSGKCAVH |
| | | | ○***○○○○○○*○○○○○*○*○○* |
| | | | SEQ ID NO: 66 |
| | | | FSTANIHPEFRLQICTSYVTCKGDCHPP |
| | | | *○○○○○○○○*○○○○*○○○○○*○○○*○** |
| | | Chikungunya virus | SEQ ID NO: 67 |
| | | | GVYPFMWGGAYCFCD |
| | | | *************** |
| | | | SEQ ID NO: 70 |
| | | | VHCAAECHPPKDHIVNY |
| | | | ○○*○*○**○******** |
| | | | SEQ ID NO: 71 |
| | | | PASHTTLGVQDISATAMSWV |
| | | | ○****○○******○****** |
| Rubivirus | Rubella virus | Rubella virus (strain BRD1) | SEQ ID NO: 72 |
| | | Rubella virus (strain BRDII) | ACTFWAVNAYSSGGYAQLASYFNPGGSYYK |
| | | Rubella virus (strain Cendehill) | ***○*○****○**○○****○**○******○ |
| | | Rubella virus (strain M33) | SEQ ID NO: 73 |
| | | Rubella virus (strain RN-UK86) | QYHPTACEVEPAFGHSDAACWGFPTDT |
| | | Rubella virus (strain THERIEN) | ***○*○*○*○****○********○*** |
| | | Rubella virus (strain TO-336 vaccine) | SEQ ID NO: 74 |
| | | Rubella virus (strain TO-336) | MSVFALASYVQHPHKTVRVKFHT |
| | | Rubella virus (vaccine strain RA27/3) | ***○○*****○**○**○****** |
| | | | SEQ ID NO: 159 |
| | | | ETRTVWQLSVAGVSC |

TABLE 1-continued

| | | | |
|---|---|---|---|
| | | | ○*○*********○○* |
| | | | SEQ ID NO: 76 |
| | | | NVTTEHPFCNMPHGQLEVQVPP |
| | | | ○*○*○**○○*○*○****○*○○* |
| | | | SEQ ID NO: 77 |
| | | | DPGDLVEYIMNYTGNQQSRW |
| | | | ****○******○*○****** |
| | | | SEQ ID NO: 78 |
| | | | GSPNCHGPDWASPVCQRHSPDCS |
| | | | ****○***○************** |
| | | | SEQ ID NO: 79 |
| | | | RLVGATPERPRLRLV |
| | | | ○***○**○**○**** |
| | | | SEQ ID NO: 80 |
| | | | DADDPLLRTAPGP |
| | | | *○○********** |
| | | | SEQ ID NO: 81 |
| | | | GEVWVTPVIGSQARKCGL |
| | | | ○○*○**○**○*****○** |
| | | | SEQ ID NO: 86 |
| | | | HIRAGPYGHATVEM |
| | | | ○○***********○ |
| | | | SEQ ID NO: 87 |
| | | | PEWIHAHTTSDPWHP |
| | | | ○**○○○○*○***○*○ |
| | | | SEQ ID NO: 88 |
| | | | PGPLGLKFKTVRPVALPR |
| | | | ****○***○**○*○○*** |
| | | | SEQ ID NO: 89 |
| | | | ALAPPRNVRVTGCYQCGTPAL |
| | | | ○○○○**○*○*○**○******* |
| | | | SEQ ID NO: 90 and SEQ ID NO: 91 |
| | | | EGLAPGGGNCHLTVNGEDVG |
| | | | ***○*****○**○○*○*○○* |
| | | | SEQ ID NO: 207 |
| | | | LLNTPPPYQVSCGG |
| | | | ******○*○*○*** |
| | | | SEQ ID NO: 92 |
| | | | RASARVIDPAAQSFTGWYGTHT |
| | | | **○***○○*○************* |
| | | | SEQ ID NO: 93 |
| | | | TAVSETRQTWAEWAAAHWWQLTLG |
| | | | ○*******○○○*****○******* |
| Bunya-viridae | Hanta-virus (continued on next page) | Amur virus | SEQ ID NO: 94 |
| | | Bayou virus | NPPDCPGVGTGCTACGVYLD |
| | | Black Creek Canal virus | **○****○********○*** |
| | | | SEQ ID NO: 95 |
| | | Cano Delgadito virus | RKVCIQLGTEQTCKTIDSNDC |
| | | | *○○*○*○*○*○○**○○*○*** |
| | | Calabazo virus | SEQ ID NO: 96 |
| | | Catacamas virus | DTLLFLGPLEEGGMIFKQWCTTTCQFGDPGDIM |
| | | Choclo virus | SEQ ID NO: 97 |

TABLE 1-continued

| | | |
|---|---|---|
| | Dobrava-Belgrade | GSFRKKCSFATLPSCQYDGNTVSG |
| | virus | *○***○*○***○*○*○○○**○○** |
| | El Moro Canyon | SEQ ID NO: 98 |
| | virus | ATKDSFQSFNITEPH |
| | Hantaan virus | **○****○**○○○○* |
| | Isla Vista virus | SEQ ID NO: 99 |
| | Khabarovsk virus | GSGVGFNLVCSVSLTEC |
| | Laguna Negra | ******○*○*○○○**** |
| | virus | SEQ ID NO: 100 |
| | Limestone Canyon | KACDSAMCYGSSTANLVRGQNT |
| | virus | ****○*○***○○○○○*○**○** |
| | Monongahela virus | SEQ ID NO: 101 |
| | Muleshoe virus | GKGGHSGSKFMCCHDKKCSATGLVAAAPHL |
| | Muju virus | ********○*○***○○○*○○○**○*○○*** |
| | New York virus | SEQ ID NO: 102 |
| | Oran virus | DDGAPQCGVHCWFKKSGEW |
| | Playa de Oro | ***○*○*○○○***○○**** |
| | virus | |
| | Prospect Hill | |
| | virus | |
| | Puumala virus | |
| | Rio Mamore virus | |
| | Rio Segundo virus | |
| | Saaremaa virus | |
| | Seoul virus | |
| | Sin Nombre virus | |
| | Soochong virus | |
| | Thailand virus | |
| | Thottapalayam | |
| | virus | |
| | Topografov virus | |
| | Tula virus | |
| Ortho-bunya-virus | Anopheles A virus | SEQ ID NO: 103 |
| | Anopheles B virus | KHDELCTGPCPVNINHQTGWLT |
| | Bakau virus | *○*○***○**○○○○○○○○*○*○ |
| | Batama virus | SEQ ID NO: 104 |
| | Bwamba virus | WGCEEFGCLAVSDGCVFGSCQD |
| | Caraparu virus | **○*○○**○*○○○**○○***** |
| | Kaeng Khoi virus | SEQ ID NO: 105 |
| | Kairi virus | GNGVPRFDYLCHLASRKEVIVRKC |
| | Madrid virus | *○*○○○*○○○*○○○○*○○○○○*○* |
| | Main Drain virus | SEQ ID NO: 106 |
| | Marituba virus | SCAGCINCFQNIHC |
| | Nyando virus | *○**○○○○○○○○○* |
| | Oriboca virus | |
| | Oropouche virus | |
| | Sathuperi virus | |
| | Shamonda virus | |
| | Shuni virus | |
| | Simbu virus | |
| | Tacaiuma virus | |
| | Tete virus | |
| | Turlock virus | |

TABLE 1-continued

| | |
|---|---|
| unclassified Orthobunyavirus | |
| Akabane virus | Sabo virus |
| | Tinaroo virus |
| | Yaba-7 virus |
| Bunyamwera virus | Batai virus |
| | Birao virus |
| | Bozo virus |
| | Cache Valley virus |
| | Fort Sherman virus |
| | Germiston virus |
| | Guaroa virus |
| | Iaco virus |
| | Ilesha virus |
| | Lokern virus |
| | Maguari virus |
| | Mboke virus |
| | Ngari virus |
| | Northway virus |
| | Playas virus |
| | Potosi virus |
| | Shokwe virus |
| | Tensaw virus |
| | Tlacotalpan virus |
| | Xingu virus |
| California Encephalitis virus | California encephalitis serogroup virus |
| | LEIV |
| | California encephalitis virus - BFS-283 |
| | Chatanga virus |
| | Inkoo virus |
| | Jamestown Canyon virus |
| | Jamestown Canyon-like virus |
| | Jerry Slough virus |
| | Keystone virus |
| | La Crosse virus |
| | Lumbo virus |
| | Melao virus |
| | Morro Bay virus |
| | San Angelo virus |
| | Serra do Navio virus |
| | Snowshoe hare virus |
| | South River virus |
| | Tahyna virus |
| | Trivittatus virus |
| Caraparu virus | Apeu virus |
| | Bruconha virus |
| | Ossa virus |
| | Vinces virus |
| Manzanilla virus | Buttonwillow virus |
| | Ingwavuma virus |
| | Mermet virus |
| Marituba virus | Gumbo Limbo virus |
| | Murutucu virus |

TABLE 1-continued

| | | | |
|---|---|---|---|
| | | Nepuyo virus | |
| | | Restan virus | |
| | Wyeomyia virus | Anhembi virus | |
| | | BeAr328208 virus | |
| | | Macaua virus | |
| | | Sororoca virus | |
| | | Taiassui virus | |
| Phlebovirus | Bujaru virus<br>Candiruvirus<br>Chilibre virus<br>Frijoles virus<br>Punta<br>Tor_\|Salehabad<br>virus<br>Sandflyfever<br>Naples virus<br>Uukuniemi viruso<br>virus | | |
| | Rift Valley<br>fever virus | | SEQ ID NO: 107<br>KTVSSELSCREGQSYWT<br>**○○**○○*○**○*○**<br>SEQ ID NO: 108<br>GSFSPKCLSSRRC<br>*******○○○○○○<br>SEQ ID NO: 109<br>ENKCFEQCGGWGCGCFNVNPSCLFVHT<br>**○*○**○*○○*○○***○○○***○**○<br>SEQ ID NO: 110<br>WGSVSLSLDAEGISGSNSFSF<br>**○○○*○**○*○*○*○*○○**<br>SEQ ID NO: 111<br>RQGFLGEIRCNSE<br>*○*****○**○○*<br>SEQ ID NO: 112<br>AHESCLRAPNLVSYKPMIDQLEC<br>*○○**○○**○○○○*○*○○*○○○*<br>SEQ ID NO: 113<br>DPFVVFERGSLPQTR<br>**○○○*○○*○***○*<br>SEQ ID NO: 114<br>QAFSKGSVQADLTLMFD<br>**○○○*○○○*○○○○○○*<br>SEQ ID NO: 115<br>CDAAFLNLTGCYSCNAG<br>*○*○*○*○○*****○○*<br>SEQ ID NO: 116<br>CQILHFTVPEVEEEFMYSC<br>*○○○*○○○*○○○○○○○*○*<br>SEQ ID NO: 117<br>STVVNPKSGSWN<br>*○*○**○○○○○○<br>SEQ ID NO: 118<br>FFDWFSGLMSWFGGPLK |

TABLE 1-continued

| | | |
|---|---|---|
| | | *○***○○*○**○○○○○○ |
| unclassified | Anhanga virus | |
| Phlebovirus (continued on next page) | Arumowot virus | |
| | Chagres virus | |
| | Corfou virus | |
| | Gabek Forest virus | |
| | Itaporanga virus | |
| | Phlebovirus Adria/ALB1/2005 | |
| | Phlebovirus Adria/ALB5/2005 | |
| | Phlebovirus AH12 | |
| | Phlebovirus AH12/China/2010 | |
| | Phlebovirus AH15/China/2010 | |
| | Phlebovirus B105-05 | |
| | Phlebovirus B151-04 | |
| | Phlebovirus B43-02 | |
| | Phlebovirus B68-03 | |
| | Phlebovirus B79-02 | |
| | Phlebovirus Chios-A | |
| | Phlebovirus Cyprus | |
| | Phlebovirus HB29/China/2010 | |
| | Phlebovirus HN13/China/2010 | |
| | Phlebovirus HN6/China/2010 | |
| | Phlebovirus Hu/Xinyang1/China/2010 | |
| | Phlebovirus Hu/Xinyang2/China/2010 | |
| | Phlebovirus IB13-04 | |
| | Phlebovirus JS2007-01 | |
| | Phlebovirus JS24 | |
| | Phlebovirus JS26 | |
| | Phlebovirus JS3/China/2010 | |
| | Phlebovirus JS4/China/2010 | |
| | Phlebovirus JS6 | |
| | Phlebovirus JSD1 | |
| | Phlebovirus LN2/China/2010 | |
| | Phlebovirus LN3/China/2010 | |
| | Phlebovirus sandflies/Gr29/Spain/2004 | |
| | Phlebovirus sandflies/Gr36/Spain/2004 | |
| | Phlebovirus sandflies/Gr44/Spain/2004 | |
| | Phlebovirus sandflies/Gr49/Spain/2004 | |
| | Phlebovirus sandflies/Gr52/Spain/2004 | |
| | Phlebovirus sandflies/Gr65/Spain/2004 | |
| | Phlebovirus sandflies/Gr98/Spain/2004 | |
| | Phlebovirus SD24/China/2010 | |
| | Phlebovirus SD4/China/2010 | |
| | Phlebovirus tick/XCQ-2011 | |
| | Phlebovirus XLL/China/2009 | |
| | Rio Grande virus | |
| | Salobo virus | |
| | Sandfly fever sicilian virus | |
| | Sandfly Sicilian Turkey virus | |
| | Utique virus | |
| | Phlebovirus sp. | |
| | Phlebovirus sp. Be An 24262 | |
| | Phlebovirus sp. Be An 356637 | |

TABLE 1-continued

| | | | | |
|---|---|---|---|---|
| | | | Phlebovirus sp. Be An 416992 | |
| | | | Phlebovirus sp. Be An 578142 | |
| | | | Phlebovirus sp. Be Ar 371637 | |
| | | | Phlebovirus sp. Co Ar 170255 | |
| | | | Phlebovirus sp. Co Ar 171616 | |
| | | | Phlebovirus sp. GML 902878 | |
| | | | Phlebovirus sp. Pa Ar 2381 | |
| | | | Phlebovirus sp. PAN 479603 | |
| | | | Phlebovirus sp. PAN 483391 | |
| | | | Phlebovirus sp. VP-161A | |
| | | | Phlebovirus sp. VP-334K | |
| | | | Phlebovirus sp. VP-366G | |
| Orthomyxoviridae | Influenzavirus A | Influenza A virus | INFA H1 | SEQ ID NO: 119<br>GLFGAIAGFIEGGWTG<br>SEQ ID NO: 178<br>WTYNAELLVLLENERTLD<br>SEQ ID NO: 179<br>NAELLVLLENERTLDYHD |
| | | | INFA H2 | SEQ ID NO: 120<br>GLFGAIAGFIEGGWQG<br>SEQ ID NO: 180<br>WTYNAELLVLMENERTLD<br>SEQ ID NO: 181<br>NAELLVLMENERTLDYHD |
| | | | INFA H3 | SEQ ID NO: 121<br>GIFGAIAGFIENGWEG<br>SEQ ID NO: 182<br>WSYNAELLVALENQHTID<br>SEQ ID NO: 183<br>NAELLVALENQHTIDLTD |
| | | | INFA H4 | SEQ ID NO: 122<br>GLFGAIAGFIENGWQG<br>SEQ ID NO: 182<br>WSYNAELLVALENQHTID<br>SEQ ID NO: 184<br>NAELLVALENQHTIDVTD |
| | | | INFA H5 | SEQ ID NO: 120<br>GLFGAIAGFIEGGWQG<br>SEQ ID NO: 180<br>WTYNAELLVLMENERTLD<br>SEQ ID NO: 185<br>NAELLVLMENERTLDFHD |
| | | | INFA H6 | SEQ ID NO: 123<br>GIFGAIAGFIEGGWTG<br>SEQ ID NO: 119<br>GLFGAIAGFIEGGWTG<br>SEQ ID NO: 178<br>WTYNAELLVLLENERTLD<br>SEQ ID NO: 186<br>NAELLVLLENERTLDMHD |

TABLE 1-continued

| | |
|---|---|
| INFA H7 | SEQ ID NO: 187 |
| | WSYNAELLVAMENQHTID |
| | SEQ ID NO: 208 |
| | WSYNAELLVAMENQHLAD |
| INFA H8 | SEQ ID NO: 124 |
| | GLFGAIAGFIEGGWSG |
| | SEQ ID NO: 189 |
| | WAYNAELLVLLENQKTLD |
| | SEQ ID NO: 190 |
| | NAELLVLLENQKTLDEHD |
| INFA H9 | SEQ ID NO: 125 |
| | GLFGAIAGFIEGGWPG |
| | SEQ ID NO: 124 |
| | GLFGAIAGFIEGGWSG |
| | SEQ ID NO: 189 |
| | WAYNAELLVLLENQKTLD |
| | SEQ ID NO: 190 |
| | NAELLVLLENQKTLDEHD |
| INFA H10 | SEQ ID NO: 191 |
| | WTYQAELLVAMENQHTID |
| | SEQ ID NO: 192 |
| | QAELLVAMENQHTIDMAD |
| INFA H11 | SEQ ID NO: 125 |
| | GLFGAIAGFIEGGWPG |
| | SEQ ID NO: 193 |
| | WSYNAQLLVLLENEKTLD |
| | SEQ ID NO: 194 |
| | NAQLLVLLENEKTLDLHD |
| INFA H12 | SEQ ID NO: 125 |
| | GLFGAIAGFIEGGWPG |
| | SEQ ID NO: 189 |
| | WAYNAELLVLLENQKTLD |
| | SEQ ID NO: 190 |
| | NAELLVLLENQKTLDEHD |
| INFA H13 | SEQ ID NO: 125 |
| | GLFGAIAGFIEGGWPG |
| | SEQ ID NO: 195 |
| | WSYNAKLLVLLENDKTLD |
| | SEQ ID NO: 196 |
| | NAKLLVLLENDKTLDMHD |
| INFA H14 | SEQ ID NO: 122 |
| | GLFGAIAGFIENGWQG |
| | SEQ ID NO: 182 |
| | WSYNAELLVALENQHTID |
| | SEQ ID NO: 184 |
| | NAELLVALENQHTIDVTD |
| INFA H15 | SEQ ID NO: 187 |
| | WSYNAELLVAMENQHTID |
| | SEQ ID NO: 188 |
| | NAELLVAMENQHTIDLAD |

TABLE 1-continued

| | | | | |
|---|---|---|---|---|
| | | | INFA H16 | SEQ ID NO: 125 |
| | | | | GLFGAIAGFIEGGWPG |
| | | | | SEQ ID NO: 197 |
| | | | | WSYNAKLLVLIENDRTLD |
| | | | | SEQ ID NO: 198 |
| | | | | NAKLLVLIENDRTLDLHD |
| | Influenzavirus B | Influenza B virus | All strains | SEQ ID NO: 126 |
| | | | | GFFGAIAGFLEGGWEG |
| | | | | SEQ ID NO: 199 |
| | | | | ISSQIELAVLLSNEGIIN |
| | | | | SEQ ID NO: 200 |
| | | | | QIELAVLLSNEGIINSED |
| | Influenzavirus C | Influenza C virus | | |
| Paramyxoviridae | Paramyxovirinae | Avulavirus | Avian paramyxovirus 2 Yucaipa virus | SEQ ID NO: 127 |
| | | | Avian paramyxovirus 3 | GAIALGVATAAAVTAG |
| | | | Avian paramyxovirus 3b | oooo*o*oo*o*oo** |
| | | | Avian paramyxovirus 4 | |
| | | | Avian paramyxovirus 5 | |
| | | | Avian paramyxovirus 6 | |
| | | | Avian paramyxovirus 7 | |
| | | | Avian paramyxovirus 8 | |
| | | | Avian paramyxovirus 9 | |
| | | | Newcastle disease virus | |
| | | | Pigeon paramyxovirus 1 | |
| | | | unclassified Avulavirus | |
| | | | Avian paramyxovirus 10_Avian paramyxovirus duck/Miyagi/885/05 | |
| | | | Avian paramyxovirus penguin/Falkland Islands/324/2007 | |
| | | | Goosramyxovirus HZ | |
| | | | Goose paramyxovirus JS/1/97/Go | |
| | | | Goose paramyxovirus SF02 | |
| | | Henipavirus | Hendra virus Hendra virus horse/Australia/Hendra/1994 | |
| | | | Nipah virus | |
| | | | unclassified Henipavirus | |
| | | | Bat paramyxovirus Eid.hel/GH45/2008 | |
| | | Morbillivirus | Canine distemper virus | |
| | | | Cetacean morbillivirus_Dolphin morbillivirus_Pilot whale morbillivirus | |
| | | | Porpoise morbillivirus | |
| | | | Measles virus | |
| | | | Peste-des-petits-ruminants virus | |
| | | | Phocine distemper virus | |
| | | | Phocine distemper virus 1 | |
| | | | Phocine distemper virus-2 | |
| | | | Rinderpest virus | |
| | | Respirovirus | Bovine parainfluenza virus 3 | |
| | | | Porcine paramyxovirus strain Frost | |
| | | | Porcine paramyxovirus strain Texas | |
| | | | Human parainfluenza virus 1 | |

TABLE 1-continued

| | | | |
|---|---|---|---|
| | | Human parainfluenza virus 3 | |
| | | Simian Agent 10 | |
| | | Sendai virus | |
| | | unclassified Respirovirus | |
| | | Atlantic salmon respirovirus | |
| | | Guinea pig parainfluenza virus TS-9 | |
| | | Pacific salmon paramyxovirus | |
| | | Trask River 1983 Swine parainfluenza virus 3 | |
| | | Tursiops truncatus parainfluenza virus 1 | |
| | Rubulavirus | Human parainfluenza virus 2 | |
| | | Human parainfluenza virus 2 (strain Greer) | |
| | | Human parainfluenza virus 2 (strain Toshiba) | |
| | | Human parainfluenza virus 4 | |
| | | Human parainfluenza virus 4a | |
| | | Human parainfluenza virus 4b | |
| | | Mapuera virus | |
| | | Mumps virus | |
| | | Parainfluenza virus 5 | |
| | | Porcine rubulavirus | |
| | | Simian virus 41 | |
| | | unclassified Rubulavirus | |
| | | Porcine parainfluenza virus | |
| | | Tuhoko virus 1 | |
| | | Tuhoko virus 2 | |
| | | Tuhoko virus 3 | |
| | unclassified Paramyxovirinae | Atlantic salmon paramyxovirus | |
| | | Beilong virus | |
| | | Canine parainfluenza virus | |
| | | Chimeric human parainfluenza virus rPIV3-2 | |
| | | Fer-de-lance virus | |
| | | J-virus | |
| | | Menangle virus | |
| | | Mossman virus | |
| | | Murayama virus | |
| | | Ovine parainfluenza virus 3 | |
| | | Pacific salmon paramyxovirus | |
| | | Paramyxovirus GonoGER85 | |
| | | Recombinant PIV3/PIV1 virus | |
| | | Reptilian paramyxovirus | |
| | | Salem virus | |
| | | Salmo salar paramyxovirus | |
| | | Snake ATCC-VR-1408 paramyxovirus | |
| | | Snake ATCC-VR-1409 paramyxovirus | |
| | | Tioman virus | |
| | | Tupaia paramyxovirus | |
| Pneumovirus | Human respiratory syncytial virus | Human respiratory syncytial virus A | SEQ ID NO: 128 |
| | | Human respiratory syncytial virus (strain RSB1734) | FLGLILGLGAAVTAGVA<br>***○○**○*○*○○○*○* |

TABLE 1-continued

| | | | |
|---|---|---|---|
| | | Human respiratory syncytial virus (strain RSB5857)<br>Human respiratory syncytial virus (strain RSB6190)<br>Human respiratory syncytial virus (strain RSB6256)<br>Human respiratory syncytial virus (strain RSB642)<br>Human respiratory syncytial virus (strain RSB6614)<br>Human respiratory syncytial virus A strain Long LinkOut<br>Human respiratory syncytial virus A2<br>Human respiratory syncytial virus B<br>Human respiratory syncytial virus (subgroup B/strain 18537)<br>Human respiratory syncytial virus (subgroup B strain 8/60)<br>Human Respiratory syncytial virus 9320<br>Human respiratory syncytial virus B1<br>Human respiratory syncytial virus S2<br>Human respiratory syncytial virus strain RSS-2<br>unclassified Human respiratory syncytial virus | SEQ ID NO: 129<br>TNEAVVSLTNGMSVL<br>**○*****○**○***<br>SEQ ID NO: 130<br>VIRFQQLNKRLLE<br>**○***○*○****<br>SEQ ID NO: 131<br>REFSSNAGLT<br>****○***○*<br>SEQ ID NO: 132<br>MLTDRELTSIVGGM<br>***○○**○*○○○○*<br>SEQ ID NO: 133<br>YVIQLPLFGVMDTDCW<br>*○○***○○**○**○**<br>SEQ ID NO: 134<br>CLARADNGWYCHNAGSLSYFP<br>**○○○*○**○*○****○*○**<br>SEQ ID NO: 135<br>DTLKSLTVPVTSRECN<br>**○○***○*○○○○○**<br>SEQ ID NO: 136<br>YDCKISTSKTYVSTAVLTTMG<br>*○*○*○***○○○*○○*○*○○*<br>SEQ ID NO: 137<br>VSCYGHNSCTVIN<br>*****○○○**○○*<br>SEQ ID NO: 209<br>GIIRTLPDGCHYISNKGVDRVQVGNTVYYLSKE<br>VGK<br>***○*○○○**○*○**○*○*○*○****○**○○*○<br>○**<br>SEQ ID NO: 139<br>PLSFPDDKFDVAIRDVEHSINQTRTFLKASDQL<br>L<br>**○**○*○*○○○*○○*○○○***○○○*○○○**○*<br>*<br>SEQ ID NO: 140<br>KIMTSKTDISSSVITSIGAIVSCYG<br>○*○***○○○*○○*○*○○*○○***** |
| | Bovine respiratory syncytial virus | All strains | SEQ ID NO: 128<br>FLGLILGLGAAVTAGVA<br>***○○**○*○*○○○*○* |
| Metapneum | Avian metapneumo-virus | All strains | SEQ ID NO: 134<br>CLARADNGWYCHNAGSLSYFP<br>**○○○*○**○*○****○*○** |
| | Human metapneumo-virus | All strains | SEQ ID NO: 133<br>YVIQLPLFGVMDTDCW<br>*○○***○○**○**○** |

TABLE 1-continued

| | | | | |
|---|---|---|---|---|
| Coronaviridae | Coronavirinae | Alphacorona-virus | Alphacoronavirus 1 | SEQ ID NO: 141 |
| | | | Coronavirus group 1b | RSAIEDLLFDKVKLSDVG |
| | | | Human coronavirus 229E | **○○****○○**○○○*○* |
| | | | Human coronavirus NL63 | SEQ ID NO: 142 |
| | | | Miniopterus bat coronavirus 1 | VPFYLNVQYRINGLGVT |
| | | | Miniopterus bat coronavirus HKU8 | ○**○○○○○**○**○*** |
| | | | Porcine epidemic diarrhea virus | SEQ ID NO: 143 |
| | | | Rhinolophus bat coronavirus HKU2 | VLSQNQKLIANAFNNALHAIQ |
| | | | Scotophilus bat coronavirus 512 | **○○***○*○○○*○○*○○○** |
| | | | unclassified Alphacoronavirus | SEQ ID NO: 144 |
| | | Betacorona-virus | Betacoronavirus 1 | TNSALVKIQAVVNANA |
| | | | Coronavirus group 2b | *○○**○*○*○***○○* |
| | | | Coronavirus group 2c | SEQ ID NO: 145 |
| | | | Human coronavirus HKU1 | AEAQIDRLINGRLTALNAYVSQQL |
| | | | Murine coronavirus | *○○******○***○○*○○*○○*** |
| | | | Pipistrellus bat coronavirus HKU5 | SEQ ID NO: 146 |
| | | | Rousettus bat coronavirus HKU9 | SAAQAMEKVNECVKSQSSRINFCGNGNHIIS |
| | | | Severe acute respiratory syndrome-related coronavirus recombinant SARSr-CoV | ○*○○*○○*○○***○○*○○*○○***○*○*○○* |
| | | | | SEQ ID NO: 147 |
| | | | | APYGLYFIHFNYVP |
| | | | SARS coronavirus | **○*○○*○*○○*○* |
| | | | Tylonycteris bat coronavirus HKU4 | SEQ ID NO: 148 |
| | | | unclassified Betacoronavirus | LQEAIKVLNHSYINLKDIGTYEYYVKWPWYVW |
| | | | | ○○*○○*○**○*○○○*○○○*○○*○*○******○* |
| | | Gammacorona-virus | Avian coronavirus | |
| | | | Beluga Whale coronavirus SW1 | |
| | | unclassified coronaviruses | Alpaca coronavirus CA08-1/2008 | |
| | | | Bat coronavirus | |
| | | | Bird droppings coronavirus | |
| | | | Bovine respiratory coronavirus | |
| | | | Chicken enteric coronavirus | |
| | | | Coronavirus Anas | |
| | | | Coronavirus oystercatcher/p17/2006/GBR | |
| | | | Coronavirus red knot/p60/2006/GBR | |
| | | | Ferret enteric coronavirus 1202 | |
| | | | Ferret systemic coronavirus MSU-S | |
| | | | Ferret systemic coronavirus WADL | |
| | | | Guangxi coronaviridae | |
| | | | Human coronavirus NO | |
| | | | Human enteric coronavirus strain 4408 | |
| | | | Kenya bat coronavirus | |
| | | | Mink coronavirus strain WD1133 | |
| | | | Parrot coronavirus AV71/99 | |
| | | | Quail coronavirus Italy/Elvia/2005 | |
| | | | Tai Forest coronavirus | |
| | | | unidentified coronavirus | |
| | | | unidentified human coronavirus | |
| Arena-viridae | Arena-virus | LCMV-Lassa virus (Old World) complex | Ippy virus | SEQ ID NO: 149 |
| | | | Lassa virus | NALINDQLIMKNHLRDIMGIPYC |
| | | | Lujo virus | *○**○***○*○***○*○**○*** |
| | | | Lymphocytic choriomeningitis virus | SEQ ID NO: 150 |

TABLE 1-continued

| | | | | |
|---|---|---|---|---|
| | | | Mobala virus | FTWTLSDSEGKDTPGGYCLT |
| | | | Mopeia virus | ○○*○○○*○○*○○○***○**○ |
| | | | | SEQ ID NO: 151 |
| | | | | KCFGNTAIAKCNQKHDEEFCDMLRLFDFN |
| | | | | ***○*○○○****○○*○○****○○○*○○○* |
| | | | | SEQ ID NO: 152 |
| | | | | MLQKEYMERQGKTPLGLVDLFVFS |
| | | | | *○○○*○○**○○**○○*○*○○○○*○ |
| | | Tacaribe virus | Amapari virus | SEQ ID NO: 150 |
| | | (New World) | Chapare virus | FTWTLSDSEGKDTPGGYCLT |
| | | complex | Flexal virus | ○○*○○○*○○*○○○***○**○ |
| | | | Guanarito virus | SEQ ID NO: 151 |
| | | | Junin virus | KCFGNTAIAKCNQKHDEEFCDMLRLFDFN |
| | | | Latino virus | ***○*○○○****○○*○○****○○○*○○○* |
| | | | Machupo virus | SEQ ID NO: 152 |
| | | | Oliveros virus | MLQKEYMERQGKTPLGLVDLFVFS |
| | | | Parana virus | *○○○*○○**○○**○○*○*○○○○*○ |
| | | | Pichinde virus | |
| | | | Pirital virus | |
| | | | Sabia virus | |
| | | | Tacaribe virus | |
| | | | Tamiami virus | |
| | | | Whitewater Arroyo virus | |
| Hepadnaviridae | Genus | Hepatitis B virus | HBV genotype A | SEQ ID NO: 153 |
| | | Orthohepadnavirus | HBV genotype B | FNPLGFFPSHQLDPLF |
| | | | HBV genotype C | ○***○*○*○*○*○*○* |
| | | | HBV genotype D | SEQ ID NO: 154 |
| | | | HBV genotype E | ADWDKNPNKDPWP |
| | | | HBV genotype F | ○*○*○*○○*○○○○ |
| | | | HBV genotype G | SEQ ID NO: 155 |
| | | | HBV genotype H | MESITSGFLGPLLVLQAVFF |
| | | | Hepatitis B virus alpha1 | ○○○○○○○○*○○○○○**○○○○ |
| | | | Hepatitis B virus LSH/chimpanzee | SEQ ID NO: 156 |
| | | | Hepatitis B virus strain cpz | LLTRILTIPQSLDSWWTSLNFLGGA |
| | | | Hepatitis B virus subtype adr | ○○○○○○*○○○○*○○○○***○*○*○○ |
| | | | Hepatitis B virus subtype adw | SEQ ID NO: 157 |
| | | | Hepatitis B virus subtype adyw | CPPTCPGYRWMC |
| | | | Hepatitis B virus subtype ayw | ○○*○*****○*○ |
| | | | | SEQ ID NO: 158 |
| | | | | LFILLLCLIFLLVLLDYQ |
| | | | | *○○*○○○*○○*○○*○○○○ |
| Rhabdoviridae | Dimarhabdovirus | Ephemerovirus | Bovine ephemeral fever virus | SEQ ID NO: 160 |
| | | | | LDGYLCRKQKWEVTCTETWYFVTD |
| | | | | *○*○○****○*○○○*○*****○*○ |
| | | | | SEQ ID NO: 161 |
| | | | | KYQIIEVIPTENEC |
| | | | | ○***○**○*○○○○* |
| | | | | SEQ ID NO: 162 |
| | | | | LKGEYIPPYYPPTNCVWNAIDTQE |
| | | | | ○○*○○*******○○*○**○○○○** |
| | | | | SEQ ID NO: 163 |

TABLE 1-continued

| | | | |
|---|---|---|---|
| | | | IEDPVTMTLMDSKFTKPC |
| | | | ○○○*○○○○○○**○*○○** |
| | | | SEQ ID NO: 164 |
| | | | LHCQIKSWECIPV |
| | | | ○**○○*○****○* |
| | | | SEQ ID NO: 165 |
| | | | SHRNMMEALYLESPD |
| | | | *○○*○○*○*○○*○** |
| | | | SEQ ID NO: 166 |
| | | | LTFCGYNGILLDNGEWWSIY |
| | | | ○****○○**○○○○****** |
| | | | SEQ ID NO: 167 |
| | | | ELEHEKCLGTLEKLQNGE |
| | | | *****○**○*○○*○○*○* |
| | | | SEQ ID NO: 168 |
| | | | LDLSYLSPSNPGKHYAY |
| | | | **○***○*○○**○○*** |
| | | | SEQ ID NO: 169 |
| | | | IRAVCYYHTFSMNLD |
| | | | ○**○*○*○○*○○○○* |
| | Vesiculovirus | Carajas virus | SEQ ID NO: 170 |
| | | Chandipura virus | EWKTTCDYRWYGPQYITHSI |
| | | Cocal virus | ○*○****○*****○*○*○* |
| | | Isfahan virus | SEQ ID NO: 171 |
| | | Maraba virus | LGFPPQSCGWASVTT |
| | | Piry virus | ○****○○**○○○○○○ |
| | | recombinant Vesiculovirus | SEQ ID NO: 1 |
| | | Spring viraemia of carp virus | VQVTPHHVLVDEYTGEWVDSQFINGKC |
| | | Vesicular stomatitis Alagoas virus | ○○○○○*○*○○○○*○*○*○*○○○○○○○○ |
| | | Vesicular stomatitis Indiana virus | |
| | | Vesicular stomatitis New Jersey virus | |
| Lyssavirus | Aravan virus | | |
| | Australian bat lyssavirus | | |
| | Duvenhage virus | | |
| | European bat lyssavirus 1 | | |
| | European bat lyssavirus 2 | | |
| | Irkut virus | | |
| | Khujand virus | | |
| | Lagos bat virus | | |
| | Mokola virus | | |
| | West Caucasian bat virus | | |
| | Rabies virus | Rabies virus AB21 | SEQ ID NO: 5 |
| | | Rabies virus AB22 | GFTCTGVVTEAETYTNFVGYVT |
| | | Rabies virus AVO1 | *○****○**○*○○*○○○○*** |
| | | Rabies virus BNG4 | SEQ ID NO: 6 |
| | | Rabies virus BNG5 | SLHNPYPDYRWLRTVKTT |
| | | Rabies virus China/DRV | *○○○○○○○○○○○***○* |
| | | Rabies virus China/MRV | SEQ ID NO: 210 |
| | | Rabies virus CVS-11 | ESLVIISPSVADLDPYDRSLHS |

TABLE 1-continued

| | | | |
|---|---|---|---|
| | | Rabies virus ERA | *○○○***○○○○*○**○○○ |
| | | Rabies virus Eth2003 | SEQ ID NO: 211 |
| | | Rabies virus HEP-FLURY | CKLKLCGVLGLRLMDGT |
| | | Rabies virus India | *○○○****○○○○*○○○* |
| | | Rabies virus Nishigahara RCEH | SEQ ID NO: 212 |
| | | Rabies virus Ontario fox | ILGPDGNVLIPEMQSS |
| | | Rabies virus Ontario skunk | ○**○*○○○*******○ |
| | | Rabies virus PM | SEQ ID NO: 213 |
| | | Rabies virus red fox/08RS-1981/Udine/2008 | QHMELLESSVIPLVHPL<br>*○○○**○*○○○**○○** |
| | | Rabies virus SAD B19 | |
| | | Rabies virus silver-haired bat-associated SHBRV | |
| | | Rabies virus strain Pasteur vaccin | |
| | | Rabies virus strain Street | |
| | | Rabies virus vnukovo-32 | |
| | | Thailand genotype 1 dog lyssavirus | |
| | unclassified Lyssavirus | Bokeloh bat lyssavirus<br>European bat lyssavirus<br>Lyssavirus Ozernoe<br>Shimoni bat virus | |
| Novirhabdovirus | Hirame rhabdovirus<br>Infectious hematopoietic necrosis virus<br>Snakehead rhabdovirus<br>Viral hemorrhagic septicemia virus | | |
| unassigned Rhabdoviridae | Bangoran virus<br>Bimbo virus<br>Bivens Arm virus<br>Flanders virus<br>Garba virus<br>Klamath virus<br>Malpais Spring virus<br>Nasoule virus<br>Ngaingan virus<br>Ouango virus<br>Sigma virus<br>Tupaia virus<br>Wongabel virus | | |

| Family | Genus | Species (group) | Species (Strain) | Peptides from domains from fusion proteins exhibiting immunosuppressive activity (ISU) | knock-out (K.O.) mutants of the immunosuppressive domain (ISU) |
|---|---|---|---|---|---|
| Flavi-viridae | Flavi-virus | Aroa virus | Bussuquara virus<br>guape virus<br>Naranjal virus | | SEQ ID NO: 202<br>DRGWGNGCGDFGKG |

TABLE 1-continued

| | | |
|---|---|---|
| Dengue virus | Dengue 1 | SEQ ID NO: 2<br>DRGWGNGCGLFGKG<br>**************<br>SEQ ID NO: 172<br>KGSSIGKMFESTYRGAKRMAILG |
| | Dengue 2 | SEQ ID NO: 2<br>DRGWGNGCGLFGKG<br>************** |
| | Dengue 3 | SEQ ID NO: 2<br>DRGWGNGCGLFGKG<br>**************<br>SEQ ID NO: 204<br>GDTAWDFGSVGGVLNSLGK<br>******************* |
| | Dengue 4 | SEQ ID NO: 2<br>DRGWGNGCGLFGKG<br>************** |
| Japanese encephalitis virus group | Japanese encephalitis virus | SEQ ID NO: 2<br>DRGWGNGCGLFGKG<br>************** |
| | Koutango virus | SEQ ID NO: 2<br>DRGWGNGCGLFGKG<br>************** |
| | Murray Valley encephalitis Virus | SEQ ID NO: 2<br>DRGWGNGCGLFGKG<br>************** |
| | St. Louis encephalitis virus | SEQ ID NO: 2<br>DRGWGNGCGLFGKG<br>************** |
| | Usutu virus | SEQ ID NO: 2<br>DRGWGNGCGLFGKG<br>************** |
| | West Nile virus | SEQ ID NO: 2<br>DRGWGNGCGLFGKG<br>************** |
| Kokobera virus group | Kokobera Virus unclassified Kokobera virus group | SEQ ID NO: 2<br>DRGWGNGCGLFGKG |
| Modoc Virus group | Modoc Virus<br>Cowbone Ridge virus<br>Jutiapa virus<br>Sal Vieja virus<br>San Perlita virus | |
| mosquito-borne viruses | Ilheus virus | SEQ ID NO: 2<br>DRGWGNGCGLFGKG |
| | Sepik virus | SEQ ID NO: 2<br>DRGWGNGCGLFGKG |
| Ntaya virus group | Bagaza virus | SEQ ID NO: 2<br>DRGWGNGCGLFGKG |
| | Tembusu virus | SEQ ID NO: 2<br>DRGWGNGCGLFGKG |
| | Yokose virus | SEQ ID NO: 2<br>DRGWGNGCGLFGKG |
| Rio Bravo virus | Apoi virus | SEQ ID NO: 2 |

TABLE 1-continued

| | | |
|---|---|---|
| group | | DRGWGNGCGLFGKG |
| | Entebbe bat virus | SEQ ID NO: 2 DRGWGNGCGLFGKG |
| | Rio Bravo virus | SEQ ID NO: 2 DRGWGNGCGLFGKG |
| | Saboya virus | |
| Seaborne tick-borne virus group | Meaban virus | |
| | Saumarez Reef virus | |
| | Tyuleniy virus | |
| Spondweni virus group | Zika virus | SEQ ID NO: 2 DRGWGNGCGLFGKG |
| | Kyasanur forest disease virus | |
| | Langat virus | |
| | Louping ill virus | |
| | Omsk hemorrhagic fever virus | |
| | Powassan virus | |
| | Royal Farm virus | |
| | Tick-borne encephalitis virus | |
| Yaounde virus | | SEQ ID NO: 2 DRGWGNGCGLFGKG |
| Yellow fever virus group | Banzi virus | SEQ ID NO: 2 DRGWGNGCGLFGKG |
| | Bouboui virus | SEQ ID NO: 2 DRGWGNGCGLFGKG |
| | Edge Hill virus | |
| | Uganda S virus | |
| | Wesselsbron virus | |
| | Yellow fever virus | SEQ ID NO: 2 DRGWGNGCGLFGKG |
| unclassified Flavivirus | Batu Cave virus | SEQ ID NO: 2 DRGWGNGCGLFGKG |
| | Cacipacore virus | |
| | Calbertado virus | |
| | Cell fusing agent virus | |
| | Chaoyang virus | |
| | Chimeric Tick-borne encephalitis virus/Dengue virus 4 | |
| | Culex theileri flavivirus | |
| | Donggang virus | |
| | Duck hemorrhagic ovaritis virus | |
| | Flavivirus Aedes/MO-Ac/ITA/2009 | |
| | Flavivirus Anopheles/PV-Am/ITA/2009 | |
| | Flavivirus CbaAr4001 | |
| | Flavivirus FSME | |
| | Flavivirus Phlebotomine/76/Arrabida/2007 | |
| | Gadgets Gully virus | |
| | Greek goat encephalitis virus | |
| | Jugra virus | |
| | Kadam virus | |
| | Kamiti River virus | |
| | Kedougou virus | |
| | Montana myotis leukoencephalitis virus | |
| | Mosquito flavivirus | |

TABLE 1-continued

| | | | |
|---|---|---|---|
| | | Ngoye virus | |
| | | Nounane virus | |
| | | Phlebotomus flavivirus Alg_F19 | |
| | | Phlebotomus flavivirus Alg_F8 | |
| | | Quang Binh virus | |
| | | Russian Spring-Summer encephalitis virus | |
| | | Sokoluk virus | |
| | | Spanish sheep encephalitis virus | |
| | | T'Ho virus | |
| | | Tai forest virus B31 | |
| | | Tamana bat virus | |
| | | Tick-borne flavivirus | |
| | | Wang Thong virus | |
| | | Flavivirus sp. | |
| | | Aedes flavivirus | |
| | | Culex flavivirus | |
| Hepacivirus | Hepatitis C virus | Hepatitis C virus genotype 1 a | SEQ ID NO: 3<br>GLIHLHQNIVDVQYLYG<br>SEQ ID NO: 175<br>PALSTGLIHLHQNIVDVQ |
| | | Hepatitis C virus genotype 1b | |
| | | Hepatitis C virus genotype 2 | |
| | | Hepatitis C virus genotype 3 | SEQ ID NO: 3<br>GLIHLHQNIVDVQYLYG |
| | | Hepatitis C virus genotype 4 | SEQ ID NO: 3<br>GLIHLHQNIVDVQYLYG |
| | | Hepatitis C virus genotype 5 | |
| | | Hepatitis C virus genotype 6 | SEQ ID NO: 3<br>GLIHLHQNIVDVQYLYG |
| | | All Hepatitis C virus | SEQ ID NO: 3<br>GLIHLHQNIVDVQYLYG |
| Pesti virus | Border disease virus | Border disease virus - | |
| | | Border disease virus - X818 | |
| | | Border disease virus 1 | |
| | | Border disease virus 2 | |
| | | Border disease virus 3 | |
| | | Border disease virus isolates | |
| | Bovine viral diarrhea virus 1 | Bovine viral diarrhea virus 1-CP7 | |
| | | Bovine viral diarrhea virus 1-NADL | |
| | | Bovine viral diarrhea virus 1-Osloss | |
| | | Bovine viral diarrhea virus 1-SD1 | |
| | | Bovine viral diarrhea virus isolates and strains | |
| | | Bovine viral diarrhea virus type 1a | |
| | | Bovine viral diarrhea virus type 1b | |
| | | Pestivirus isolate 97-360 | |
| | | Pestivirus isolate Hay 87/2210 | |
| | | Pestivirus strain mousedeer | |
| | | Pestivirus type 1 isolates | |
| | Bovine viral diarrhea virus 2 (BVDV-2) | Bovine viral diarrhea virus 2 | |
| | | Pestivirus sp. strain 178003 | |
| | | Pestivirus sp. strain 5250Giessen-3 | |
| | | Bovine viral diarrhea virus-2 isolate | |

TABLE 1-continued

| | | | |
|---|---|---|---|
| | | | SCP |
| | | Classical swine fever virus | Classical swine fever virus |
| | | | Hog cholera virus strain Zoelen |
| | | unclassified Pestivirus | Bovine viral diarrhea virus 3 |
| | | | Chamois pestivirus 1 |
| | | | Porcine pestivirus isolate Bungowannah |
| | Unnclassified Flaviviridae | | Barkedji virus |
| | | | Canine hepacivirus AAK-2011 |
| | | | GB virus A |
| | | | Douroucouli hepatitis GB virus A |
| | | | GBV-A-like agents |
| | | | GB virus D |
| | | | GBV-C/HGV group |
| | | | GB virus C |
| | | | Hepatitis GB virus C-like virus |
| | | | Hepatitis GB virus B |
| | | | Lammi virus |
| | | | Marmoset hepatitis GB virus A |
| | | | Nakiwogo virus |
| | | | Turkey meningoencephalitis virus |
| Togaviridae | Alpha-virus | Aura virus | |
| | | Barmah Forest virus | |
| | | Middelburg virus | |
| | | Ndumu virus | |
| | | Salmon pancreas disease virus | |
| | | Getah virus | |
| | | Mayaro virus | |
| | | Trocara virus | |
| | | EEEV complex | |
| | | WEEV complex | Fort Morgan virus |
| | | | Highlands J virus |
| | | | Sindbis virus |
| | | | Western equine encephalomyelitis virus |
| | | | Whataroa virus |
| | | VEEV complex | Cabassou virus |
| | | | Mucambo virus |
| | | | Pixuna virus |
| | | | Venezuelan equine encephalitis virus |
| | | SFV complex | Bebaru virus |
| | | | O'nyong-nyong virus |
| | | | Ross River virus |
| | | | Semliki forest virus |
| | | | Una virus |
| | | | Chikungunya virus |
| | Rubivirus | Rubella virus | Rubella virus (strain BRD1) |
| | | | Rubella virus (strain BRDII) |
| | | | Rubella virus (strain Cendehill) |
| | | | Rubella virus (strain M33) |
| | | | Rubella virus (strain RN-UK86) |

TABLE 1-continued

| | | | |
|---|---|---|---|
| | | | Rubella virus (strain THERIEN) |
| | | | Rubella virus (strain TO-336 vaccine) |
| | | | Rubella virus (strain TO-336) |
| | | | Rubella virus (vaccine strain RA27/3) |
| Bunya-viridae | Hanta-virus (continued on next page) | Amur virus | |
| | | Bayou virus | |
| | | Black Creek Canal virus | |
| | | Cano Delgadito virus | |
| | | Calabazo virus | |
| | | Catacamas virus | |
| | | Choclo virus | |
| | | Dobrava-Belgrade virus | |
| | | El Moro Canyon virus | |
| | | Hantaan virus | |
| | | Isla Vista virus | |
| | | Khabarovsk virus | |
| | | Laguna Negra virus | |
| | | Limestone Canyon virus | |
| | | Monongahela virus | |
| | | Muleshoe virus | |
| | | Muju virus | |
| | | New York virus | |
| | | Oran virus | |
| | | Playa de Oro virus | |
| | | Prospect Hill virus | |
| | | Puumala virus | |
| | | Rio Mamore virus | |
| | | Rio Segundo virus | |
| | | Saaremaa virus | |
| | | Seoul virus | |
| | | Sin Nombre virus | |
| | | Soochong virus | |
| | | Thailand virus | |
| | | Thottapalayam virus | |
| | | Topografov virus | |
| | | Tula virus | |
| | Ortho-bunya-virus | Anopheles A virus | |
| | | Anopheles B virus | |
| | | Bakau virus | |
| | | Batama virus | |
| | | Bwamba virus | |
| | | Caraparu virus | |
| | | Kaeng Khoi virus | |

TABLE 1-continued

| | |
|---|---|
| Kairi virus | |
| Madrid virus | |
| Main Drain virus | |
| Marituba virus | |
| Nyando virus | |
| Oriboca virus | |
| Oropouche virus | |
| Sathuperi virus | |
| Shamonda virus | |
| Shuni virus | |
| Simbu virus | |
| Tacaiuma virus | |
| Tete virus | |
| Turlock virus | |
| unclassified Orthobunyavirus | |
| Akabane virus | Sabo virus |
| | Tinaroo virus |
| | Yaba-7 virus |
| Bunyamwera virus | Batai virus |
| | Birao virus |
| | Bozo virus |
| | Cache Valley virus |
| | Fort Sherman virus |
| | Germiston virus |
| | Guaroa virus |
| | Iaco virus |
| | Ilesha virus |
| | Lokern virus |
| | Maguari virus |
| | Mboke virus |
| | Ngari virus |
| | Northway virus |
| | Playas virus |
| | Potosi virus |
| | Shokwe virus |
| | Tensaw virus |
| | Tlacotalpan virus |
| | Xingu virus |
| California Encephalitis virus | California encephalitis serogroup virus |
| | LEIV |
| | California encephalitis virus - BFS-283 |
| | Chatanga virus |
| | Inkoo virus |
| | Jamestown Canyon virus |
| | Jamestown Canyon-like virus |
| | Jerry Slough virus |
| | Keystone virus |
| | La Crosse virus |
| | Lumbo virus |
| | Melao virus |
| | Morro Bay virus |
| | San Angelo virus |

TABLE 1-continued

| | | |
|---|---|---|
| | | Serra do Navio virus |
| | | Snowshoe hare virus |
| | | South River virus |
| | | Tahyna virus |
| | | Trivittatus virus |
| | Caraparu virus | Apeu virus |
| | | Bruconha virus |
| | | Ossa virus |
| | | Vinces virus |
| | Manzanilla virus | Buttonwillow virus |
| | | Ingwavuma virus |
| | | Mermet virus |
| | Marituba virus | Gumbo Limbo virus |
| | | Murutucu virus |
| | | Nepuyo virus |
| | | Restan virus |
| | Wyeomyia virus | Anhembi virus |
| | | BeAr328208 virus |
| | | Macaua virus |
| | | Sororoca virus |
| | | Taiassui virus |
| Phlebovirus | Bujaru virus | |
| | Candiruvirus | |
| | Chilibre virus | |
| | Frijoles virus | |
| | Punta Tor_|Salehabad virus | |
| | Sandflyfever Naples virus | |
| | Uukuniemi viruso virus | |
| | Rift Valley fever virus | |
| | unclassified Phlebovirus | Anhanga virus |
| | | Arumowot virus |
| | | Chagres virus |
| | | Corfou virus |
| | | Gabek Forest virus |
| | | Itaporanga virus |
| | | Phlebovirus Adria/ALB1/2005 |
| | | Phlebovirus Adria/ALB5/2005 |
| | | Phlebovirus AH12 |
| | | Phlebovirus AH12/China/2010 |
| | | Phlebovirus AH15/China/2010 |
| | | Phlebovirus B105-05 |
| | | Phlebovirus B151-04 |
| | | Phlebovirus B43-02 |
| | | Phlebovirus B68-03 |
| | | Phlebovirus B79-02 |
| | | Phlebovirus Chios-A |
| | | Phlebovirus Cyprus |
| | | Phlebovirus HB29/China/2010 |

(continued on next page)

TABLE 1-continued

| | | | | | |
|---|---|---|---|---|---|
| | | | Phlebovirus HN13/China/2010 | | |
| | | | Phlebovirus HN6/China/2010 | | |
| | | | Phlebovirus Hu/Xinyang1/China/2010 | | |
| | | | Phlebovirus Hu/Xinyang2/China/2010 | | |
| | | | Phlebovirus IB13-04 | | |
| | | | Phlebovirus JS2007-01 | | |
| | | | Phlebovirus JS24 | | |
| | | | Phlebovirus JS26 | | |
| | | | Phlebovirus JS3/China/2010 | | |
| | | | Phlebovirus JS4/China/2010 | | |
| | | | Phlebovirus JS6 | | |
| | | | Phlebovirus JSD1 | | |
| | | | Phlebovirus LN2/China/2010 | | |
| | | | Phlebovirus LN3/China/2010 | | |
| | | | Phlebovirus sandflies/Gr29/Spain/2004 | | |
| | | | Phlebovirus sandflies/Gr36/Spain/2004 | | |
| | | | Phlebovirus sandflies/Gr44/Spain/2004 | | |
| | | | Phlebovirus sandflies/Gr49/Spain/2004 | | |
| | | | Phlebovirus sandflies/Gr52/Spain/2004 | | |
| | | | Phlebovirus sandflies/Gr65/Spain/2004 | | |
| | | | Phlebovirus sandflies/Gr98/Spain/2004 | | |
| | | | Phlebovirus SD24/China/2010 | | |
| | | | Phlebovirus SD4/China/2010 | | |
| | | | Phlebovirus tick/XCQ-2011 | | |
| | | | Phlebovirus XLL/China/2009 | | |
| | | | Rio Grande virus | | |
| | | | Salobo virus | | |
| | | | Sandfly fever sicilian virus | | |
| | | | Sandfly Sicilian Turkey virus | | |
| | | | Utique virus | | |
| | | | Phlebovirus sp. | | |
| | | | Phlebovirus sp. Be An 24262 | | |
| | | | Phlebovirus sp. Be An 356637 | | |
| | | | Phlebovirus sp. Be An 416992 | | |
| | | | Phlebovirus sp. Be An 578142 | | |
| | | | Phlebovirus sp. Be Ar 371637 | | |
| | | | Phlebovirus sp. Co Ar 170255 | | |
| | | | Phlebovirus sp. Co Ar 171616 | | |
| | | | Phlebovirus sp. GML 902878 | | |
| | | | Phlebovirus sp. Pa Ar 2381 | | |
| | | | Phlebovirus sp. PAN 479603 | | |
| | | | Phlebovirus sp. PAN 483391 | | |
| | | | Phlebovirus sp. VP-161A | | |
| | | | Phlebovirus sp. VP-334K | | |
| | | | Phlebovirus sp. VP-366G | | |
| Orthomyxoviridae | Influenzavirus A | Influenza A virus | INFA H1 | | INF F#2 DELTA6: SEQ ID NO: 201 GLFGAAGFIENGWEG InFAH1-3: SEQ ID NO: 203 |
| | | | INFA H2 | | |
| | | | INFA H3 | SEQ ID NO: 4 GLFGAIAGFIENGWEG | |

TABLE 1-continued

| | | | | |
|---|---|---|---|---|
| | | | INFA H4 | |
| | | | INFA H5 | |
| | | | INFA H6 | |
| | | | INFA H7 | SEQ ID NO: 4 GLFGAIAGFIENGWEG |
| | | | INFA H8 | |
| | | | INFA H9 | |
| | | | INFA H10 | SEQ ID NO: 4 GLFGAIAGFIENGWEG |
| | | | INFA H11 | |
| | | | INFA H12 | |
| | | | INFA H13 | |
| | | | INFA H14 | |
| | | | INFA H15 | SEQ ID NO: 4 GLFGAIAGFIENGWEG |
| | | | INFA H16 | |
| | Influenzavirus B | Influenza B virus | All strains | |
| | Influenzavirus C | Influenza C virus | | |
| Paramyxoviridae | Paramyxovirinae | Avulavirus | Avian paramyxovirus 2 Yucaipa virus | |
| | | | Avian paramyxovirus 3 | |
| | | | Avian paramyxovirus 3b | |
| | | | Avian paramyxovirus 4 | |
| | | | Avian paramyxovirus 5 | |
| | | | Avian paramyxovirus 6 | |
| | | | Avian paramyxovirus 7 | |
| | | | Avian paramyxovirus 8 | |
| | | | Avian paramyxovirus 9 | |
| | | | Newcastle disease virus | |
| | | | Pigeon paramyxovirus 1 | |
| | | | unclassified Avulavirus | |
| | | | Avian paramyxovirus 10_Avian paramyxovirus duck/Miyagi/885/05 | |
| | | | Avian paramyxovirus penguin/Falkland Islands/324/2007 | |
| | | | Goosramyxovirus HZ | |
| | | | Goose paramyxovirus JS/1/97/Go | |
| | | | Goose paramyxovirus SF02 | |
| | | Henipavirus | Hendra virus Hendra virus horse/Australia/Hendra/1994 | |
| | | | Nipah virus | |
| | | | unclassified Henipavirus | |
| | | | Bat paramyxovirus Eid.hel/GH45/2008 | |
| | | Morbillivirus | Canine distemper virus | |
| | | | Cetacean morbillivirus_Dolphin morbillivirus_Pilot whale morbillivirus | |
| | | | Porpoise morbillivirus | |
| | | | Measles virus | |
| | | | Peste-des-petits-ruminants virus | |
| | | | Phocine distemper virus | |
| | | | Phocine distemper virus 1 | |

TABLE 1-continued

| | |
|---|---|
| | Phocine distemper virus-2 |
| | Rinderpest virus |
| Respirovirus | Bovine parainfluenza virus 3 |
| | Porcine paramyxovirus strain Frost |
| | Porcine paramyxovirus strain Texas |
| | Human parainfluenza virus 1 |
| | Human parainfluenza virus 3 |
| | Simian Agent 10 |
| | Sendai virus |
| | unclassified Respirovirus |
| | Atlantic salmon respirovirus |
| | Guinea pig parainfluenza virus TS-9 |
| | Pacific salmon paramyxovirus |
| | Trask River 1983 Swine parainfluenza virus 3 |
| | Tursiops truncatus parainfluenza virus 1 |
| Rubulavirus | Human parainfluenza virus 2 |
| | Human parainfluenza virus 2 (strain Greer) |
| | Human parainfluenza virus 2 (strain Toshiba) |
| | Human parainfluenza virus 4 |
| | Human parainfluenza virus 4a |
| | Human parainfluenza virus 4b |
| | Mapuera virus |
| | Mumps virus |
| | Parainfluenza virus 5 |
| | Porcine rubulavirus |
| | Simian virus 41 |
| | unclassified Rubulavirus |
| | Porcine parainfluenza virus |
| | Tuhoko virus 1 |
| | Tuhoko virus 2 |
| | Tuhoko virus 3 |
| unclassified Paramyxovirinae | Atlantic salmon paramyxovirus |
| | Beilong virus |
| | Canine parainfluenza virus |
| | Chimeric human parainfluenza virus rPIV3-2 |
| | Fer-de-lance virus |
| | J-virus |
| | Menangle virus |
| | Mossman virus |
| | Murayama virus |
| | Ovine parainfluenza virus 3 |
| | Pacific salmon paramyxovirus |
| | Paramyxovirus GonoGER85 |
| | Recombinant PIV3/PIV1 virus |
| | Reptilian paramyxovirus |
| | Salem virus |
| | Salmo salar paramyxovirus |
| | Snake ATCC-VR-1408 paramyxovirus |
| | Snake ATCC-VR-1409 paramyxovirus |

TABLE 1-continued

| | | | |
|---|---|---|---|
| | | | Tioman virus |
| | | | Tupaia paramyxovirus |
| | Pneumovirus | Human respiratory syncytial virus | Human respiratory syncytial virus A |
| | | | Human respiratory syncytial virus (strain RSB1734) |
| | | | Human respiratory syncytial virus (strain RSB5857) |
| | | | Human respiratory syncytial virus (strain RSB6190) |
| | | | Human respiratory syncytial virus (strain RSB6256) |
| | | | Human respiratory syncytial virus (strain RSB642) |
| | | | Human respiratory syncytial virus (strain RSB6614) |
| | | | Human respiratory syncytial virus A strain Long LinkOut |
| | | | Human respiratory syncytial virus A2 |
| | | | Human respiratory syncytial virus B |
| | | | Human respiratory syncytial virus (subgroup B/strain 18537) |
| | | | Human respiratory syncytial virus (subgroup B strain 8/60) |
| | | | Human Respiratory syncytial virus 9320 |
| | | | Human respiratory syncytial virus B1 |
| | | | Human respiratory syncytial virus S2 |
| | | | Human respiratory syncytial virus strain RSS-2 |
| | | | unclassified Human respiratory syncytial virus |
| | | Bovine respiratory syncytial virus | All strains |
| | Metapneum | Avian metapneumo-virus | All strains |
| | | Human metapneumo-virus | All strains |
| Coronaviridae | Coronavirinae | Alphacorona-virus | Alphacoronavirus 1 |
| | | | Coronavirus group 1b |
| | | | Human coronavirus 229E |
| | | | Human coronavirus NL63 |
| | | | Miniopterus bat coronavirus 1 |
| | | | Miniopterus bat coronavirus HKU8 |
| | | | Porcine epidemic diarrhea virus |
| | | | Rhinolophus bat coronavirus HKU2 |
| | | | Scotophilus bat coronavirus 512 |
| | | | unclassified Alphacoronavirus |
| | | Betacorona-virus | Betacoronavirus 1 |
| | | | Coronavirus group 2b |
| | | | Coronavirus group 2c |
| | | | Human coronavirus HKU1 |
| | | | Murine coronavirus |

TABLE 1-continued

| | | | |
|---|---|---|---|
| | | | Pipistrellus bat coronavirus HKU5 |
| | | | Rousettus bat coronavirus HKU9 |
| | | | Severe acute respiratory syndrome-related coronavirus recombinant SARSr-CoV |
| | | | SARS coronavirus |
| | | | Tylonycteris bat coronavirus HKU4 |
| | | | unclassified Betacoronavirus |
| | | Gammacorona-virus | Avian coronavirus |
| | | | Beluga Whale coronavirus SW1 |
| | | unclassified coronaviruses | Alpaca coronavirus CA08-1/2008 |
| | | | Bat coronavirus |
| | | | Bird droppings coronavirus |
| | | | Bovine respiratory coronavirus |
| | | | Chicken enteric coronavirus |
| | | | Coronavirus Anas |
| | | | Coronavirus oystercatcher/p17/2006/GBR |
| | | | Coronavirus red knot/p60/2006/GBR |
| | | | Ferret enteric coronavirus 1202 |
| | | | Ferret systemic coronavirus MSU-S |
| | | | Ferret systemic coronavirus WADL |
| | | | Guangxi coronaviridae |
| | | | Human coronavirus NO |
| | | | Human enteric coronavirus strain 4408 |
| | | | Kenya bat coronavirus |
| | | | Mink coronavirus strain WD1133 |
| | | | Parrot coronavirus AV71/99 |
| | | | Quail coronavirus Italy/Elvia/2005 |
| | | | Tai Forest coronavirus |
| | | | unidentified coronavirus |
| | | | unidentified human coronavirus |
| Arena-viridae | Arena-virus | LCMV-Lassa virus (Old World) complex | Ippy virus |
| | | | Lassa virus |
| | | | Lujo virus |
| | | | Lymphocytic choriomeningitis virus |
| | | | Mobala virus |
| | | | Mopeia virus |
| | | Tacaribe virus (New World) complex | Amapari virus |
| | | | Chapare virus |
| | | | Flexal virus |
| | | | Guanarito virus |
| | | | Junin virus |
| | | | Latino virus |
| | | | Machupo virus |
| | | | Oliveros virus |
| | | | Parana virus |
| | | | Pichinde virus |
| | | | Pirital virus |
| | | | Sabia virus |
| | | | Tacaribe virus |
| | | | Tamiami virus |
| | | | Whitewater Arroyo virus |

TABLE 1-continued

| | | | |
|---|---|---|---|
| Hepadnaviridae | Genus | Hepatitis B virus Orthohepadnavirus | HBV genotype A |
| | | | HBV genotype B |
| | | | HBV genotype C |
| | | | HBV genotype D |
| | | | HBV genotype E |
| | | | HBV genotype F |
| | | | HBV genotype G |
| | | | HBV genotype H |
| | | | Hepatitis B virus alpha1 |
| | | | Hepatitis B virus LSH/chimpanzee |
| | | | Hepatitis B virus strain cpz |
| | | | Hepatitis B virus subtype adr |
| | | | Hepatitis B virus subtype adw |
| | | | Hepatitis B virus subtype adyw |
| | | | Hepatitis B virus subtype ayw |
| Rhabdoviridae | Dimarhabdovirus | Ephemerovirus | Bovine ephemeral fever virus |
| | | Vesiculovirus | Carajas virus |
| | | | Chandipura virus |
| | | | Cocal virus |
| | | | Isfahan virus |
| | | | Maraba virus |
| | | | Piry virus |
| | | | recombinant Vesiculovirus |
| | | | Spring viraemia of carp virus |
| | | | Vesicular stomatitis Alagoas virus |
| | | | Vesicular stomatitis Indiana virus |
| | | | Vesicular stomatitis New Jersey virus |
| | Lyssavirus | Aravan virus | |
| | | Australian bat lyssavirus | |
| | | Duvenhage virus | |
| | | European bat lyssavirus 1 | |
| | | European bat lyssavirus 2 | |
| | | Irkut virus | |
| | | Khujand virus | |
| | | Lagos bat virus | |
| | | Mokola virus | |
| | | West Caucasian bat virus | |
| | | Rabies virus | Rabies virus AB21 |
| | | | Rabies virus AB22 |
| | | | Rabies virus AVO1 |
| | | | Rabies virus BNG4 |
| | | | Rabies virus BNG5 |
| | | | Rabies virus China/DRV |
| | | | Rabies virus China/MRV |
| | | | Rabies virus CVS-11 |
| | | | Rabies virus ERA |
| | | | Rabies virus Eth2003 |

TABLE 1-continued

| | | | | | |
|---|---|---|---|---|---|
| | | | Rabies virus HEP-FLURY | | |
| | | | Rabies virus India | | |
| | | | Rabies virus Nishigahara RCEH | | |
| | | | Rabies virus Ontario fox | | |
| | | | Rabies virus Ontario skunk | | |
| | | | Rabies virus PM | | |
| | | | Rabies virus red fox/08RS-1981/Udine/2008 | | |
| | | | Rabies virus SAD B19 | | |
| | | | Rabies virus silver-haired bat-associated SHBRV | | |
| | | | Rabies virus strain Pasteur vaccin | | |
| | | | Rabies virus strain Street | | |
| | | | Rabies virus vnukovo-32 | | |
| | | | Thailand genotype 1 dog lyssavirus | | |
| | | unclassified Lyssavirus | Bokeloh bat lyssavirus | | |
| | | | European bat lyssavirus | | |
| | | | Lyssavirus Ozernoe | | |
| | | | Shimoni bat virus | | |
| | Novirhabdovirus | Hirame rhabdovirus | | | |
| | | Infectious hematopoietic necrosis virus | | | |
| | | Snakehead rhabdovirus | | | |
| | | Viral hemorrhagic septicemia virus | | | |
| | unassigned Rhabdoviridae | Bangoran virus | | | |
| | | Bimbo virus | | | |
| | | Bivens Arm virus | | | |
| | | Flanders virus | | | |
| | | Garba virus | | | |
| | | Klamath virus | | | |
| | | Malpais Spring virus | | | |
| | | Nasoule virus | | | |
| | | Ngaingan virus | | | |
| | | Ouango virus | | | |
| | | Sigma virus | | | |
| | | Tupaia virus | | | |
| | | Wongabel virus | | | |

| Family | Genus | Species (group) | Species (Strain) | Name of envelope attachment/ fusion protein | IU group and fusion type |
|---|---|---|---|---|---|
| Flavi-viridae | Flavi-virus | Aroa virus | Bussuquara virus | Envelope protein prME Fusion protein E | Group 1 Type II Fusion mechanism |
| | | | guape virus | | |
| | | | Naranjal virus | | |
| | | Dengue virus | Dengue 1 | | |
| | | | Dengue 2 | | |
| | | | Dengue 3 | | |

TABLE 1-continued

| | |
|---|---|
| | Dengue 4 |
| Japanese encephalitis virus group | Japanese encephalitis virus |
| | Koutango virus |
| | Murray Valley encephalitis Virus |
| | St. Louis encephalitis virus |
| | Usutu virus |
| | West Nile virus |
| Kokobera virus group | Kokobera Virus unclassified Kokobera virus group |
| Modoc Virus group | Modoc Virus |
| | Cowbone Ridge virus |
| | Jutiapa virus |
| | Sal Vieja virus |
| | San Perlita virus |
| mosquito-borne viruses | Ilheus virus |
| | Sepik virus |
| Ntaya virus group | Bagaza virus |
| | Tembusu virus |
| | Yokose virus |
| Rio Bravo virus group | Apoi virus |
| | Entebbe bat virus |
| | Rio Bravo virus |
| | Saboya virus |
| Seaborne tick-borne virus group | Meaban virus |
| | Saumarez Reef virus |
| | Tyuleniy virus |
| Spondweni virus group | Zika virus |
| | Kyasanur forest disease virus |
| | Langat virus |
| | Louping ill virus |
| | Omsk hemorrhagic fever virus |
| | Powassan virus |
| | Royal Farm virus |
| | Tick-borne encephalitis virus |
| Yaounde virus | |
| Yellow fever virus group | Banzi virus |
| | Bouboui virus |
| | Edge Hill virus |
| | Uganda S virus |
| | Wesselsbron virus |
| | Yellow fever virus |
| unclassified Flavivirus | Batu Cave virus |
| | Cacipacore virus |
| | Calbertado virus |
| | Cell fusing agent virus |
| | Chaoyang virus |

TABLE 1-continued

| | | | |
|---|---|---|---|
| | | Chimeric Tick-borne encephalitis virus/Dengue virus 4 | |
| | | Culex theileri flavivirus | |
| | | Donggang virus | |
| | | Duck hemorrhagic ovaritis virus | |
| | | Flavivirus Aedes/MO-Ac/ITA/2009 | |
| | | Flavivirus Anopheles/PV-Am/ITA/2009 | |
| | | Flavivirus CbaAr4001 | |
| | | Flavivirus FSME | |
| | | Flavivirus Phlebotomine/76/Arrabida/2007 | |
| | | Gadgets Gully virus | |
| | | Greek goat encephalitis virus | |
| | | Jugra virus | |
| | | Kadam virus | |
| | | Kamiti River virus | |
| | | Kedougou virus | |
| | | Montana myotis leukoencephalitis virus | |
| | | Mosquito flavivirus | |
| | | Ngoye virus | |
| | | Nounane virus | |
| | | Phlebotomus flavivirus Alg_F19 | |
| | | Phlebotomus flavivirus Alg_F8 | |
| | | Quang Binh virus | |
| | | Russian Spring-Summer encephalitis virus | |
| | | Sokoluk virus | |
| | | Spanish sheep encephalitis virus | |
| | | T'Ho virus | |
| | | Tai forest virus B31 | |
| | | Tamana bat virus | |
| | | Tick-borne flavivirus | |
| | | Wang Thong virus | |
| | | Flavivirus sp. | |
| | | Aedes flavivirus | |
| | | Culex flavivirus | |
| Hepacivirus | Hepatitis C virus | Hepatitis C virus genotype 1 a | E1/E2 |
| | | Hepatitis C virus genotype 1b | |
| | | Hepatitis C virus genotype 2 | |
| | | Hepatitis C virus genotype 3 | |
| | | Hepatitis C virus genotype 4 | |
| | | Hepatitis C virus genotype 5 | |
| | | Hepatitis C virus genotype 6 | |
| | | All Hepatitis C virus | |
| Pesti virus | Border disease virus | Border disease virus - | E1/E2 |
| | | Border disease virus - X818 | |
| | | Border disease virus 1 | |
| | | Border disease virus 2 | |
| | | Border disease virus 3 | |
| | | Border disease virus isolates | |
| | Bovine viral diarrhea virus 1 | Bovine viral diarrhea virus 1-CP7 | |
| | | Bovine viral diarrhea virus 1-NADL | |
| | | Bovine viral diarrhea virus 1-Osloss | |
| | | Bovine viral diarrhea virus 1-SD1 | |
| | | Bovine viral diarrhea virus isolates and | |

TABLE 1-continued

| | | | | |
|---|---|---|---|---|
| | | | strains | |
| | | | Bovine viral diarrhea virus type 1a | |
| | | | Bovine viral diarrhea virus type 1b | |
| | | | Pestivirus isolate 97-360 | |
| | | | Pestivirus isolate Hay 87/2210 | |
| | | | Pestivirus strain mousedeer | |
| | | | Pestivirus type 1 isolates | |
| | | Bovine viral diarrhea virus 2 (BVDV-2) | Bovine viral diarrhea virus 2 | |
| | | | Pestivirus sp. strain 178003 | |
| | | | Pestivirus sp. strain 5250Giessen-3 | |
| | | | Bovine viral diarrhea virus-2 isolate SCP | |
| | | Classical swine fever virus | Classical swine fever virus | |
| | | | Hog cholera virus strain Zoelen | |
| | | unclassified Pestivirus | Bovine viral diarrhea virus 3 | |
| | | | Chamois pestivirus 1 | |
| | | | Porcine pestivirus isolate Bungowannah | |
| | Unnclassified Flaviviridae | | Barkedji virus | |
| | | | Canine hepacivirus AAK-2011 | |
| | | | GB virus A | |
| | | | Douroucouli hepatitis GB virus A | |
| | | | GBV-A-like agents | |
| | | | GB virus D | |
| | | | GBV-C/HGV group | |
| | | | GB virus C | |
| | | | Hepatitis GB virus C-like virus | |
| | | | Hepatitis GB virus B | |
| | | | Lammi virus | |
| | | | Marmoset hepatitis GB virus A | |
| | | | Nakiwogo virus | |
| | | | Turkey meningoencephalitis virus | |
| Togaviridae | Alpha-virus | Aura virus | | E2/E1 |
| | | Barmah Forest virus | | |
| | | Middelburg virus | | |
| | | Ndumu virus | | |
| | | Salmon pancreas disease virus | | |
| | | Getah virus | | |
| | | Mayaro virus | | |
| | | Trocara virus | | |
| | | EEEV complex | | |
| | | WEEV complex | Fort Morgan virus | |
| | | | Highlands J virus | |
| | | | Sindbis virus | |
| | | | Western equine encephalomyelitis virus | |
| | | | Whataroa virus | |
| | | VEEV complex | Cabassou virus | |
| | | | Mucambo virus | |
| | | | Pixuna virus | |
| | | | Venezuelan equine encephalitis virus | |

TABLE 1-continued

| | | | | |
|---|---|---|---|---|
| | | SFV complex | Bebaru virus | |
| | | | O'nyong-nyong virus | |
| | | | Ross River virus | |
| | | | Semliki forest virus | |
| | | | Una virus | |
| | | | Chikungunya virus | |
| | Rubivirus | Rubella virus | Rubella virus (strain BRD1) | |
| | | | Rubella virus (strain BRDII) | |
| | | | Rubella virus (strain Cendehill) | |
| | | | Rubella virus (strain M33) | |
| | | | Rubella virus (strain RN-UK86) | |
| | | | Rubella virus (strain THERIEN) | |
| | | | Rubella virus (strain TO-336 vaccine) | |
| | | | Rubella virus (strain TO-336) | |
| | | | Rubella virus (vaccine strain RA27/3) | |
| Bunya-viridae | Hanta-virus (continued on next page) | Amur virus | | Gn(G2)/Gc(G1) |
| | | Bayou virus | | |
| | | Black Creek Canal virus | | |
| | | Cano Delgadito virus | | |
| | | Calabazo virus | | |
| | | Catacamas virus | | |
| | | Choclo virus | | |
| | | Dobrava-Belgrade virus | | |
| | | El Moro Canyon virus | | |
| | | Hantaan virus | | |
| | | Isla Vista virus | | |
| | | Khabarovsk virus | | |
| | | Laguna Negra virus | | |
| | | Limestone Canyon virus | | |
| | | Monongahela virus | | |
| | | Muleshoe virus | | |
| | | Muju virus | | |
| | | New York virus | | |
| | | Oran virus | | |
| | | Playa de Oro virus | | |
| | | Prospect Hill virus | | |
| | | Puumala virus | | |
| | | Rio Mamore virus | | |
| | | Rio Segundo virus | | |
| | | Saaremaa virus | | |
| | | Seoul virus | | |
| | | Sin Nombre virus | | |
| | | Soochong virus | | |
| | | Thailand virus | | |

TABLE 1-continued

| | | |
|---|---|---|
| | Thottapalayam virus | |
| | Topografov virus | |
| | Tula virus | |
| Ortho-bunya-virus | Anopheles A virus | |
| | Anopheles B virus | |
| | Bakau virus | |
| | Batama virus | |
| | Bwamba virus | |
| | Caraparu virus | |
| | Kaeng Khoi virus | |
| | Kairi virus | |
| | Madrid virus | |
| | Main Drain virus | |
| | Marituba virus | |
| | Nyando virus | |
| | Oriboca virus | |
| | Oropouche virus | |
| | Sathuperi virus | |
| | Shamonda virus | |
| | Shuni virus | |
| | Simbu virus | |
| | Tacaiuma virus | |
| | Tete virus | |
| | Turlock virus | |
| | unclassified Orthobunyavirus | |
| | Akabane virus | Sabo virus |
| | | Tinaroo virus |
| | | Yaba-7 virus |
| | Bunyamwera virus | Batai virus |
| | | Birao virus |
| | | Bozo virus |
| | | Cache Valley virus |
| | | Fort Sherman virus |
| | | Germiston virus |
| | | Guaroa virus |
| | | Iaco virus |
| | | Ilesha virus |
| | | Lokern virus |
| | | Maguari virus |
| | | Mboke virus |
| | | Ngari virus |
| | | Northway virus |
| | | Playas virus |
| | | Potosi virus |
| | | Shokwe virus |
| | | Tensaw virus |
| | | Tlacotalpan virus |
| | | Xingu virus |
| | California Encephalitis virus | California encephalitis serogroup virus |
| | | LEIV |
| | | California encephalitis virus - BFS-283 |

TABLE 1-continued

| | | |
|---|---|---|
| | | Chatanga virus |
| | | Inkoo virus |
| | | Jamestown Canyon virus |
| | | Jamestown Canyon-like virus |
| | | Jerry Slough virus |
| | | Keystone virus |
| | | La Crosse virus |
| | | Lumbo virus |
| | | Melao virus |
| | | Morro Bay virus |
| | | San Angelo virus |
| | | Serra do Navio virus |
| | | Snowshoe hare virus |
| | | South River virus |
| | | Tahyna virus |
| | | Trivittatus virus |
| | Caraparu virus | Apeu virus |
| | | Bruconha virus |
| | | Ossa virus |
| | | Vinces virus |
| | Manzanilla virus | Buttonwillow virus |
| | | Ingwavuma virus |
| | | Mermet virus |
| | Marituba virus | Gumbo Limbo virus |
| | | Murutucu virus |
| | | Nepuyo virus |
| | | Restan virus |
| | Wyeomyia virus | Anhembi virus |
| | | BeAr328208 virus |
| | | Macaua virus |
| | | Sororoca virus |
| | | Taiassui virus |
| Phlebovirus | Bujaru virus | |
| | Candiruvirus | |
| | Chilibre virus | |
| | Frijoles virus | |
| | Punta Tor_\|Salehabad virus | |
| | Sandflyfever Naples virus | |
| | Uukuniemi viruso virus | |
| | Rift Valley fever virus | |
| | unclassified Phlebovirus | Anhanga virus |
| | | Arumowot virus |
| | | Chagres virus |
| | | Corfou virus |
| | | Gabek Forest virus |
| | | Itaporanga virus |
| | | Phlebovirus Adria/ALB1/2005 |
| | | Phlebovirus Adria/ALB5/2005 |

(continued on next page)

TABLE 1-continued

| |
|---|
| Phlebovirus AH12 |
| Phlebovirus AH12/China/2010 |
| Phlebovirus AH15/China/2010 |
| Phlebovirus B105-05 |
| Phlebovirus B151-04 |
| Phlebovirus B43-02 |
| Phlebovirus B68-03 |
| Phlebovirus B79-02 |
| Phlebovirus Chios-A |
| Phlebovirus Cyprus |
| Phlebovirus HB29/China/2010 |
| Phlebovirus HN13/China/2010 |
| Phlebovirus HN6/China/2010 |
| Phlebovirus Hu/Xinyang1/China/2010 |
| Phlebovirus Hu/Xinyang2/China/2010 |
| Phlebovirus IB13-04 |
| Phlebovirus JS2007-01 |
| Phlebovirus JS24 |
| Phlebovirus JS26 |
| Phlebovirus JS3/China/2010 |
| Phlebovirus JS4/China/2010 |
| Phlebovirus JS6 |
| Phlebovirus JSD1 |
| Phlebovirus LN2/China/2010 |
| Phlebovirus LN3/China/2010 |
| Phlebovirus sandflies/Gr29/Spain/2004 |
| Phlebovirus sandflies/Gr36/Spain/2004 |
| Phlebovirus sandflies/Gr44/Spain/2004 |
| Phlebovirus sandflies/Gr49/Spain/2004 |
| Phlebovirus sandflies/Gr52/Spain/2004 |
| Phlebovirus sandflies/Gr65/Spain/2004 |
| Phlebovirus sandflies/Gr98/Spain/2004 |
| Phlebovirus SD24/China/2010 |
| Phlebovirus SD4/China/2010 |
| Phlebovirus tick/XCQ-2011 |
| Phlebovirus XLL/China/2009 |
| Rio Grande virus |
| Salobo virus |
| Sandfly fever sicilian virus |
| Sandfly Sicilian Turkey virus |
| Utique virus |
| Phlebovirus sp. |
| Phlebovirus sp. Be An 24262 |
| Phlebovirus sp. Be An 356637 |
| Phlebovirus sp. Be An 416992 |
| Phlebovirus sp. Be An 578142 |
| Phlebovirus sp. Be Ar 371637 |
| Phlebovirus sp. Co Ar 170255 |
| Phlebovirus sp. Co Ar 171616 |
| Phlebovirus sp. GML 902878 |
| Phlebovirus sp. Pa Ar 2381 |
| Phlebovirus sp. PAN 479603 |
| Phlebovirus sp. PAN 483391 |

TABLE 1-continued

| | | | | | |
|---|---|---|---|---|---|
| | | | Phlebovirus sp. VP-161A | | |
| | | | Phlebovirus sp. VP-334K | | |
| | | | Phlebovirus sp. VP-366G | | |
| Orthomyxoviridae | Influenzavirus A | Influenza A virus | INFA H1 | HA (HA1/HA2) | Group 2 Type I fusion mechanism |
| | | | INFA H2 | | |
| | | | INFA H3 | | |
| | | | INFA H4 | | |
| | | | INFA H5 | | |
| | | | INFA H6 | | |
| | | | INFA H7 | | |
| | | | INFA H8 | | |
| | | | INFA H9 | | |
| | | | INFA H10 | | |
| | | | INFA H11 | | |
| | | | INFA H12 | | |
| | | | INFA H13 | | |
| | | | INFA H14 | | |
| | | | INFA H15 | | |
| | | | INFA H16 | | |
| | Influenzavirus B | Influenza B virus | All strains | | |
| | Influenzavirus C | Influenza C virus | | | |
| Paramyxoviridae | Paramyxovirinae | Avulavirus | Avian paramyxovirus 2 Yucaipa virus | F0 (F2/F1) | |
| | | | Avian paramyxovirus 3 | | |
| | | | Avian paramyxovirus 3b | | |
| | | | Avian paramyxovirus 4 | | |
| | | | Avian paramyxovirus 5 | | |
| | | | Avian paramyxovirus 6 | | |
| | | | Avian paramyxovirus 7 | | |
| | | | Avian paramyxovirus 8 | | |
| | | | Avian paramyxovirus 9 | | |
| | | | Newcastle disease virus | | |
| | | | Pigeon paramyxovirus 1 | | |
| | | | unclassified Avulavirus | | |
| | | | Avian paramyxovirus 10_Avian paramyxovirus duck/Miyagi/885/05 | | |
| | | | Avian paramyxovirus penguin/Falkland Islands/324/2007 | | |
| | | | Goosramyxovirus HZ | | |
| | | | Goose paramyxovirus JS/1/97/Go | | |
| | | | Goose paramyxovirus SF02 | | |
| | | Henipavirus | Hendra virus Hendra virus horse/Australia/Hendra/1994 | | |
| | | | Nipah virus | | |
| | | | unclassified Henipavirus | | |
| | | | Bat paramyxovirus Eid.hel/GH45/2008 | | |
| | | Morbillivirus | Canine distemper virus | | |
| | | | Cetacean morbillivirus_Dolphin morbillivirus_Pilot whale morbillivirus | | |
| | | | Porpoise morbillivirus | | |

TABLE 1-continued

| | |
|---|---|
| | Measles virus |
| | Peste-des-petits-ruminants virus |
| | Phocine distemper virus |
| | Phocine distemper virus 1 |
| | Phocine distemper virus-2 |
| | Rinderpest virus |
| Respirovirus | Bovine parainfluenza virus 3 |
| | Porcine paramyxovirus strain Frost |
| | Porcine paramyxovirus strain Texas |
| | Human parainfluenza virus 1 |
| | Human parainfluenza virus 3 |
| | Simian Agent 10 |
| | Sendai virus |
| | unclassified Respirovirus |
| | Atlantic salmon respirovirus |
| | Guinea pig parainfluenza virus TS-9 |
| | Pacific salmon paramyxovirus |
| | Trask River 1983 Swine parainfluenza virus 3 |
| | Tursiops truncatus parainfluenza virus 1 |
| Rubulavirus | Human parainfluenza virus 2 |
| | Human parainfluenza virus 2 (strain Greer) |
| | Human parainfluenza virus 2 (strain Toshiba) |
| | Human parainfluenza virus 4 |
| | Human parainfluenza virus 4a |
| | Human parainfluenza virus 4b |
| | Mapuera virus |
| | Mumps virus |
| | Parainfluenza virus 5 |
| | Porcine rubulavirus |
| | Simian virus 41 |
| | unclassified Rubulavirus |
| | Porcine parainfluenza virus |
| | Tuhoko virus 1 |
| | Tuhoko virus 2 |
| | Tuhoko virus 3 |
| unclassified Paramyxovirinae | Atlantic salmon paramyxovirus |
| | Beilong virus |
| | Canine parainfluenza virus |
| | Chimeric human parainfluenza virus rPIV3-2 |
| | Fer-de-lance virus |
| | J-virus |
| | Menangle virus |
| | Mossman virus |
| | Murayama virus |
| | Ovine parainfluenza virus 3 |
| | Pacific salmon paramyxovirus |
| | Paramyxovirus GonoGER85 |
| | Recombinant PIV3/PIV1 virus |
| | Reptilian paramyxovirus |

TABLE 1-continued

| | | | | | |
|---|---|---|---|---|---|
| | | | Salem virus | | |
| | | | Salmo salar paramyxovirus | | |
| | | | Snake ATCC-VR-1408 paramyxovirus | | |
| | | | Snake ATCC-VR-1409 paramyxovirus | | |
| | | | Tioman virus | | |
| | | | Tupaia paramyxovirus | | |
| | Pneumovirus | Human respiratory syncytial virus | Human respiratory syncytial virus A | | Group 3 Type I fusion mechanism |
| | | | Human respiratory syncytial virus (strain RSB1734) | | |
| | | | Human respiratory syncytial virus (strain RSB5857) | | |
| | | | Human respiratory syncytial virus (strain RSB6190) | | |
| | | | Human respiratory syncytial virus (strain RSB6256) | | |
| | | | Human respiratory syncytial virus (strain RSB642) | | |
| | | | Human respiratory syncytial virus (strain RSB6614) | | |
| | | | Human respiratory syncytial virus A strain Long LinkOut | | |
| | | | Human respiratory syncytial virus A2 | | |
| | | | Human respiratory syncytial virus B | | |
| | | | Human respiratory syncytial virus (subgroup B/strain 18537) | | |
| | | | Human respiratory syncytial virus (subgroup B strain 8/60) | | |
| | | | Human Respiratory syncytial virus 9320 | | |
| | | | Human respiratory syncytial virus B1 | | |
| | | | Human respiratory syncytial virus S2 | | |
| | | | Human respiratory syncytial virus strain RSS-2 | | |
| | | | unclassified Human respiratory syncytial virus | | |
| | | Bovine respiratory syncytial virus | All strains | | Group 3 Type I fusion |
| | Metapneum | Avian metapneumo-virus | All strains | | |
| | | Human metapneumo-virus | All strains | | |
| Coronaviridae | Coronavirinae | Alphacorona-virus | Alphacoronavirus 1 | S (S1/S2) | Group 3 Type I fusion mechanism |
| | | | Coronavirus group 1b | | |
| | | | Human coronavirus 229E | | |
| | | | Human coronavirus NL63 | | |
| | | | Miniopterus bat coronavirus 1 | | |
| | | | Miniopterus bat coronavirus HKU8 | | |
| | | | Porcine epidemic diarrhea virus | | |
| | | | Rhinolophus bat coronavirus HKU2 | | |
| | | | Scotophilus bat coronavirus 512 | | |
| | | | unclassified Alphacoronavirus | | |

TABLE 1-continued

| | | | | | |
|---|---|---|---|---|---|
| | | Betacorona-virus | Betacoronavirus 1 | | |
| | | | Coronavirus group 2b | | |
| | | | Coronavirus group 2c | | |
| | | | Human coronavirus HKU1 | | |
| | | | Murine coronavirus | | |
| | | | Pipistrellus bat coronavirus HKU5 | | |
| | | | Rousettus bat coronavirus HKU9 | | |
| | | | Severe acute respiratory syndrome-related coronavirus recombinant SARSr-CoV | | |
| | | | SARS coronavirus | | |
| | | | Tylonycteris bat coronavirus HKU4 | | |
| | | | unclassified Betacoronavirus | | |
| | | Gammacorona-virus | Avian coronavirus | | |
| | | | Beluga Whale coronavirus SW1 | | |
| | | unclassified coronaviruses | Alpaca coronavirus CA08-1/2008 | | |
| | | | Bat coronavirus | | |
| | | | Bird droppings coronavirus | | |
| | | | Bovine respiratory coronavirus | | |
| | | | Chicken enteric coronavirus | | |
| | | | Coronavirus Anas | | |
| | | | Coronavirus oystercatcher/p17/2006/GBR | | |
| | | | Coronavirus red knot/p60/2006/GBR | | |
| | | | Ferret enteric coronavirus 1202 | | |
| | | | Ferret systemic coronavirus MSU-S | | |
| | | | Ferret systemic coronavirus WADL | | |
| | | | Guangxi coronaviridae | | |
| | | | Human coronavirus NO | | |
| | | | Human enteric coronavirus strain 4408 | | |
| | | | Kenya bat coronavirus | | |
| | | | Mink coronavirus strain WD1133 | | |
| | | | Parrot coronavirus AV71/99 | | |
| | | | Quail coronavirus Italy/Elvia/2005 | | |
| | | | Tai Forest coronavirus | | |
| | | | unidentified coronavirus | | |
| | | | unidentified human coronavirus | | |
| Arena-viridae | Arena-virus | LCMV-Lassa virus (Old World) complex | Ippy virus | GpC (Gp1/Gp2) | Group 3 Type I fusion mechanism |
| | | | Lassa virus | | |
| | | | Lujo virus | | |
| | | | Lymphocytic choriomeningitis virus | | |
| | | | Mobala virus | | |
| | | | Mopeia virus | | |
| | | Tacaribe virus (New World) complex | Amapari virus | | |
| | | | Chapare virus | | |
| | | | Flexal virus | | |
| | | | Guanarito virus | | |
| | | | Junin virus | | |
| | | | Latino virus | | |
| | | | Machupo virus | | |
| | | | Oliveros virus | | |
| | | | Parana virus | | |
| | | | Pichinde virus | | |

TABLE 1-continued

| | | | | | |
|---|---|---|---|---|---|
| | | | Pirital virus<br>Sabia virus<br>Tacaribe virus<br>Tamiami virus<br>Whitewater Arroyo virus | | |
| Hepadnaviridae | Genus | Hepatitis B virus Orthohepadnavirus | HBV genotype A<br>HBV genotype B<br>HBV genotype C<br>HBV genotype D<br>HBV genotype E<br>HBV genotype F<br>HBV genotype G<br>HBV genotype H<br>Hepatitis B virus alpha1<br>Hepatitis B virus LSH/chimpanzee<br>Hepatitis B virus strain cpz<br>Hepatitis B virus subtype adr<br>Hepatitis B virus subtype adw<br>Hepatitis B virus subtype adyw<br>Hepatitis B virus subtype ayw | L and M and S Where S mediates fusion | Group 3 Fusion mechanism - Neither type I nor type II |
| Rhabdoviridae | Dimarhabdovirus | Ephemerovirus | Bovine ephemeral fever virus | Glycoprotein G | Group 3 Neither type I nor Type II fusion mechanism |
| | | Vesiculovirus | Carajas virus<br>Chandipura virus<br>Cocal virus<br>Isfahan virus<br>Maraba virus<br>Piry virus<br>recombinant Vesiculovirus<br>Spring viraemia of carp virus<br>Vesicular stomatitis Alagoas virus<br>Vesicular stomatitis Indiana virus<br>Vesicular stomatitis New Jersey virus | | |
| | Lyssavirus | Aravan virus<br>Australian bat lyssavirus<br>Duvenhage virus<br>European bat lyssavirus 1<br>European bat lyssavirus 2<br>Irkut virus<br>Khujand virus<br>Lagos bat virus<br>Mokola virus<br>West Caucasian bat virus | | | |
| | | Rabies virus | Rabies virus AB21<br>Rabies virus AB22 | | |

TABLE 1-continued

| | | |
|---|---|---|
| | | Rabies virus AVO1 |
| | | Rabies virus BNG4 |
| | | Rabies virus BNG5 |
| | | Rabies virus China/DRV |
| | | Rabies virus China/MRV |
| | | Rabies virus CVS-11 |
| | | Rabies virus ERA |
| | | Rabies virus Eth2003 |
| | | Rabies virus HEP-FLURY |
| | | Rabies virus India |
| | | Rabies virus Nishigahara RCEH |
| | | Rabies virus Ontario fox |
| | | Rabies virus Ontario skunk |
| | | Rabies virus PM |
| | | Rabies virus red fox/08RS-1981/Udine/2008 |
| | | Rabies virus SAD B19 |
| | | Rabies virus silver-haired bat-associated SHBRV |
| | | Rabies virus strain Pasteur vaccin |
| | | Rabies virus strain Street |
| | | Rabies virus vnukovo-32 |
| | | Thailand genotype 1 dog lyssavirus |
| | unclassified Lyssavirus | Bokeloh bat lyssavirus |
| | | European bat lyssavirus |
| | | Lyssavirus Ozernoe |
| | | Shimoni bat virus |
| Novirhabdovirus | Hirame rhabdovirus | |
| | Infectious hematopoietic necrosis virus | |
| | Snakehead rhabdovirus | |
| | Viral hemorrhagic septicemia virus | |
| unassigned Rhabdoviridae | Bangoran virus | |
| | Bimbo virus | |
| | Bivens Arm virus | |
| | Flanders virus | |
| | Garba virus | |
| | Klamath virus | |
| | Malpais Spring virus | |
| | Nasoule virus | |
| | Ngaingan virus | |
| | Ouango virus | |
| | Sigma virus | |
| | Tupaia virus | |
| | Wongabel virus | |

According to an embodiment, the invention concerns a method for identifying an immunosuppressive domain in the fusion protein of an enveloped RNA virus having a lipid membrane, said method comprising:

a. Identifying at least one well conserved domain among the group consisting of the membrane associated domains of the fusion protein and the surface associated domains of the fusion protein;
b. Providing at least one peptide with the sequence of said identified at least one well conserved domain;
c. Optionally dimerizing or multimerizing said at least one peptide; and
d. Confirming the immunosuppressive activity of said at least one optionally dimerized or multimerized peptide by testing said at least one optionally dimerized or multimerized peptide for immunosuppressive activity.

The at least one well conserved domain may be identified among domains, which are membrane associated and domains, which are surface associated. Naturally, a domain which is both membrane and surface associated may be a well conserved domain.

The fusion protein may be identified by searching NCBI taxonomy (ncbi.nlm.nih.gov/Taxonomy/), and selecting proteins of the Family, Subfamily, Genus or Species to be investigated, and subsequently search these for fusion or the specific name of the fusion protein, e.g. as listed in Table 1.

The dimerized peptide could be synthetic, the multimerized peptide could be displayed as dimerized or trimerized fusion proteins either displayed alone or on membranes such as a viral particle.

One way of testing the immunosuppressive activity of the at least one dimerized or multimerized peptide is to test the immunosuppressive activity of the fusion protein in the absence and presence of the at least one dimerized or multimerized peptide, and comparing the results.

According to other embodiments, the invention concerns the method, wherein the identification of said at least one well conserved domain is done among the group consisting of the surface associated domains of the fusion protein in one or more of the different conformations of the fusion protein undergoing fusion.

According to an embodiment, the invention concerns a method, wherein the enveloped RNA virus is not selected among Retroviruses, Lentiviruses or Filoviruses. In particular, according to an embodiment, the invention concerns a method, wherein said at least one well conserved immunosuppressive domain is not located in the linker between the two heptad repeat structures just N-terminal of the transmembrane domain in the fusion protein of either Retrovirus, Lentivirus or Filovirus. More particularly, according to an embodiment, the invention concerns a method, wherein said at least one well conserved domain does not include some of the 22 amino acids located N-terminal to the first of two well conserved cysteine residues that are found in these structures in the fusion protein of either Retrovirus, Lentivirus or Filovirus. These cysteine residues are between 4 and 6 amino acid residues from one another and in many cases are believed to form disulfide bridges that stabilize the fusion proteins.

According to other embodiments, the invention concerns the method, wherein said at least one well conserved domain is selected among the group consisting of Putative ISUs and Identified ISUs of Table 1 and Seq. Id. 1-200.

According to an embodiment, the invention concerns an immunosuppressive domain identified according to the invention.

According to an embodiment, the invention concerns an immunosuppressive domain selected among the sequences of Table 1 and Seq. Id. 1-200.

According to an embodiment, the invention concerns a method for decreasing or completely abrogating the immunosuppressive properties of an immunosuppressive domain of the fusion protein of an enveloped RNA virus having a lipid membrane, said method comprising the steps of:

e. Mutating an immunosuppressive domain to provide at least one mutated peptide;
f. Optionally dimerizing or multimerizing said at least one mutated peptide;
g. Selecting one of said optionally dimerized or multimerized mutated peptides showing reduced immunosuppressive properties;
h. Mutating the fusion protein of the enveloped RNA virus to contain said selected mutated peptide having reduced immunosuppressive properties;
i. Confirming expression by testing the viral envelope protein encompassing said mutated fusion protein for capability of being expressed by at least one of cellular or viral surfaces.

The envelope protein may be identified by searching NCBI taxonomy (ncbi.nlm.nih.gov/Taxonomy/) and selecting proteins of the Family, Subfamily, Genus or Species to be investigated and subsequently searching these for envelope or the specific name for the envelope protein or the attachment and fusion protein, e.g. as listed in Table 1.

According to other embodiments, the invention concerns the method, wherein:

e. Said immunosuppressive domain is mutated to provide a plurality of mutated peptides;
f. Said plurality of mutated peptides are optionally dimerized or multimerized;
g. One of said optionally dimerized or multimerized mutated peptides showing reduced immunosuppressive properties is selected;
h. The fusion protein of the enveloped RNA virus is mutated to contain said selected optionally dimerized or multimerized peptide having reduced immunosuppressive properties;
i. Expression is confirmed by testing the viral envelope protein encompassing said mutated fusion protein for capability of being expressed by at least one of cellular or viral surfaces.

According to other embodiments, the invention concerns the method, wherein:

g. One of said optionally dimerized or multimerized mutated peptide(s) is selected, which has reduced immunosuppressive properties as shown by at least 25% reduction as compared to a dimerized Wildtype peptide.

According to other embodiments, the invention concerns the method, wherein:

e. Said mutated immunosuppressive domain is mutated to provide a knock-out mutant of Table 1 or selected among the sequences of Seq. Id. 201-203.

According to an embodiment, a proven knock-out (i.e. a mutation of the immunosuppressive domain abrogating the immunosuppressive properties of the peptide) from one family, genus, group and/or strain, may be used for another family, genus, group and/or strain.

According to an embodiment, the invention concerns a mutated peptide providing reduced immunosuppressive properties, said mutated peptide having a sequence according to Table 1 or any of Seq. Id.-202 to 203 or obtainable as said selected mutated peptide of a method according to the invention.

Preliminary experiments indicate the immunosuppressive domains may have a size of 4-30 amino acids.

According to an embodiment, the invention concerns a method for generating an enhanced immune response, comprising a method according to the invention, and further comprising the step of:

j. Using said viral envelope protein encompassing said mutated fusion protein with reduced immunosuppressive properties as an antigen for generation of an enhanced immune response.

According to an embodiment, the invention concerns a method for making an envelope protein having diminished immunosuppressive activity, comprising:

Mutating or modifying an immunosuppressive domain, identifiable according to the invention, of an enveloped RNA virus with a lipid membrane surrounding the core, to include a peptide obtainable according to the invention.

The diminished immunosuppressive activity is suitably measured by comparing to the immunosuppressive activity from an envelope of a wildtype peptide. It is preferably demonstrated by an increased proliferation of at least 25% in a cell proliferation assay of homodimers of said mutated peptide as compared to the homodimers of said non-mutated wildtype peptide at the same concentration. More preferably the cell assay is either the CTLL-2 or the PBMC assay.

According to an embodiment, the invention concerns the method, for making a envelope protein encompassing a mutated fusion protein from a enveloped RNA virus for medical use, such as therapeutic or prophylactic purpose, preferably for use as a vaccine.

According to an embodiment, the invention concerns the method, for making an enveloped protein encompassing a mutated fusion protein from an envelope RNA virus for vaccination purposes or for the generation of neutralizing antibodies.

According to an embodiment, the invention concerns the method, wherein the enveloped RNA virus has a fusion protein with a type II fusion mechanism.

According to an embodiment, the invention concerns the method, wherein the enveloped RNA virus, preferably excluding lentivius, retrovirus and filovirus, has a fusion protein with a type I fusion mechanism and where the immunosuppressive domains co-localizes with the fusion peptide in the fusion protein, preferably as demonstrated by the identification of a common immunosuppressive domain in the fusion peptide of all H1 to H16 of Influenza A and influenza B.

According to an embodiment, the invention concerns the method, wherein the enveloped RNA virus, preferably excluding lentivius, retrovirus and filovirus, has a fusion protein with a type I fusion mechanism excluding viruses with a type I fusion mechanism where the ISU co-localizes with the fusion peptide or the fusion protein has a structure that is neither a type I nor a type II fusion structure.

According to an embodiment, the invention concerns an envelope protein obtainable according to the invention.

The immunosuppressive domain has so far been identified by the inventors at two positions in two different groups of viruses A: Co-localizing with the fusion peptide exemplified by the identification of an common immunosuppressive domain in the fusion peptide of all Flavirus (Dengue virus, west Nile virus etc) and Influenza A and B viruses and B: in the hydrophobic alpha helix N-terminal of the transmembrane domain in the fusion protein exemplified by the finding of an immunosuppressive domain in said helixes of Flaviridae like e.g. Hepatitis C virus, Dengue, WestNile, Yellow fever.

The inventors have realized that the potential immunosuppressive domains are located at various positions in the fusion protein identifiable by 1): The peptide is preferably located in the fusion protein of enveloped RNA viruses;

2): The peptide is preferably capable of interacting with membranes;

3): Preferably a high degree of homology in the primary structure (sequence) of the peptide of said domain exists either within the viral species itself, in the family of viruses or in a group of viruses. This requirement is due to the immunosuppressive domain being under a dual selection pressures, one as an immunosuppressive entity ensuring protection of the viral particle from the host immune system, another as a peptide interacting with membranes; and/or 4): The position at the surface of the fusion protein at a given conformation is preferably a feature of immunosuppressive domains. This can be revealed either by position in a 3D structure or by antibody staining of cells expressing the fusion protein or on viral surfaces displaying the fusion protein.

According to an embodiment, the invention concerns a mutated envelope protein according to the invention.

According to an embodiment, the invention concerns a viral fusion protein from an enveloped RNA virus with reduced immunosuppressive properties, said fusion protein encompassing a mutated peptide, said mutated peptide displaying reduced immunosuppression, and said mutated peptide replacing an un-mutated wildtype peptide having a sequence of an ISU of Table 1 or is selected among Seq. Id. 1-200.

According to an embodiment, the invention concerns the fusion protein, where the reduced immunosuppression is identified by comparing to the un-mutated wildtype peptide when said peptide is dimerized.

According to an embodiment, the invention concerns the fusion protein, wherein said immunosuppressive activity being determined by at least 25% reduction, more preferred at least 40% reduction, in proliferation rate in a cell proliferation assay using a homodimer of said un-mutated peptide compared to the monomeric version of said peptide at the same concentration.

According to an embodiment, the invention concerns the fusion protein, wherein said cell proliferation assay is selected among the group consisting of the CTLL-2 and the PBMC assay.

According to an embodiment, the invention concerns the fusion protein, wherein said fusion protein has a type I or type II fusion mechanism.

According to an embodiment, the invention concerns the fusion protein, wherein said fusion protein has neither a type I nor type II fusion mechanism.

According to an embodiment, the invention concerns the fusion protein, wherein said mutated peptide is located either in the fusion peptide or in a, preferably amphipatic, helix upstream of the C-terminal transmembrane domain of said fusion protein.

The fusion peptide is a small membrane penetrating peptide located in the fusion protein of enveloped viruses.

According to another embodiment, the invention concerns the viral fusion protein, wherein said mutated peptide is derived from the fusion peptide from a flavivirus or Influenzavirus or from the amphipatic helix of the Flaviridae, such as the group consisting of Hepatitis C virus fusion protein, Dengue virus fusion protein, and WestNile virus fusion protein.

According to an embodiment, the invention concerns an envelope protein, said mutated fusion protein being displayed on the surface of cells wherein said mutated fusion protein is expressed.

According to an embodiment, the invention concerns the envelope protein, said mutated fusion protein being displayed on the surface of viral or viral like particles.

According to an embodiment, the invention concerns the envelope protein, having retained some fusiogenic activity.

According to an embodiment, the invention concerns the envelope protein, wherein the fusiogenic activity is measured by a technique for measuring cell-cell fusion, preferably selected among the group consisting of counting syncytia by light microscopy, resonance energy transfer based assays, and indirect reporter gene using techniques or by measuring infectious titers; alternatively, or in addition, the presence of fusiogenic activity may be indicated by the presence of at least one cell expressing the modified envelope and one cell expressing the receptor and/or coreceptors being fused together.

According to an embodiment, the invention concerns an enveloped RNA virus, different from a virus selected among the group consisting of Retrovirus, Lentivirus and Filovirus, wherein an immunosuppressive domain has been modified or mutated to decrease or completely abrogate the immunosuppressive properties of an immunosuppressive domain of the fusion protein.

According to an embodiment, the invention concerns a virus selected among the vira of Table 1, wherein an immunosuppressive domain has been modified or mutated to decrease or completely abrogate the immunosuppressive properties of an immunosuppressive domain of the fusion protein.

According to an embodiment, the invention concerns an antigen obtainable by selecting a part of a mutated envelope protein according to any of the preceding claims, said part comprising the mutated domain of said envelope protein.

According to an embodiment, the invention concerns an antigen comprising an mutated immunosuppressive domain selected among the sequences of Table 1 and Seq. Id. 201 to 202.

According to an embodiment, the invention concerns an antigen of the invention furthermore harboring 1 or 2 or 3 or 4 or 5 or 6 or 7 or 8 or 9 or 10 or 11 point mutation(s) in any of the sequences of Table 1 or of Seq. Id. 1-200.

According to an embodiment, the invention concerns an antigen, which mediates fusion of virus to host cells.

According to an embodiment, the invention concerns an antigen, which is recombinant or obtained by recombinant technology.

According to an embodiment, the invention concerns a nucleic acid sequence, preferably recombinant, encoding a mutated envelope protein, an envelope polypeptide or an antigen according to any of the preceding claims.

According to an embodiment, the invention concerns an isolated eukaryotic expression vector comprising a nucleic acid sequence according to the invention.

According to another embodiment, the invention concerns the vector, which is a virus vector, preferably a virus selected among the group consisting of vaccinia virus, measles virus, retroviridae, lentivirus, baculovirus and adeno virus.

According to an embodiment, the invention concerns a method for producing an antibody, said method comprising the steps of:

- Administering an entity selected among a mutated envelope, an envelope polypeptide, an antigen, a nucleic acid sequence or a vector according to any of the preceding claims to a host, such as an animal; and
- Obtaining the antibody from said host.

According to an embodiment, the invention concerns an antibody obtainable according to a method of the invention.

According to another embodiment, the invention concerns an antibody, which is specific for an entity selected among a mutated peptide, an envelope protein, a mutated envelope protein, an antigen, a nucleic acid sequence or a vector according to any of the preceding claims.

According to an embodiment, the invention concerns neutralizing antibodies obtained or identified by the use of at least one envelope protein according to any of the preceding claims.

According to an embodiment, the invention concerns a method for manufacturing neutralizing antibodies comprising the use of at least one protein according to any of the preceding claims.

According to an embodiment, the invention concerns a method for manufacturing humanized neutralizing antibodies, comprising the use of at least one sequence selected among the sequences of Table 1 and sequences 201 to 203

According to an embodiment, the invention concerns a vaccine comprising a virus according to the invention.

According to an embodiment, the invention concerns a vaccine comprising an envelope protein from a virus according to the invention.

According to an embodiment, the invention concerns a vaccine composition comprising an envelope protein according to any of the preceding claims.

According to an embodiment, the invention concerns a vaccine composition comprising a virus like particle (VLP).

According to an embodiment, the invention concerns the vaccine composition, wherein the virus like particle is produced ex vivo in a cell culture.

According to an embodiment, the invention concerns the vaccine composition, wherein the virus like particle is partly or completely assembled ex vivo.

According to an embodiment, the invention concerns the vaccine composition, wherein the virus like particle is generated in vivo in the patient by infection, transfection and/or electroporation by expression vectors.

According to an embodiment, the invention concerns the vaccine composition, comprising a vector derived from a measles or vaccinia virus.

According to an embodiment, the invention concerns the vaccine composition, comprising an expression vector for DNA vaccination.

According to an embodiment, the invention concerns the vaccine composition, comprising a purified envelope protein.

According to an embodiment, the invention concerns the vaccine composition, comprising a multimerized purified envelope protein.

According to an embodiment, the invention concerns the vaccine composition, comprising a dimerized purified envelope protein.

According to an embodiment, the invention concerns the vaccine composition, comprising a trimerized purified envelope protein.

According to an embodiment, the invention concerns a vaccine composition comprising an entity selected among the group consisting of a mutated envelope protein, an envelope polypeptide, an antigen, a nucleic acid sequence, a vector and an antibody according to any of the preceding claims, and in addition at least one excipient, carrier or diluent.

According to an embodiment, the invention concerns the vaccine composition, further comprising at least one adjuvant.

According to an embodiment, the invention concerns a medical composition comprising antibodies raised using a virus according to the invention.

individual, or prophylactic treating an individual, comprising administering an amount of mutated peptide, an envelope protein, a mutated envelope protein, antigen, nucleic acid sequence, vector or vaccine composition according to any of the preceding claims.

According to an embodiment, the invention may be used with human and/or animal vira.

Table 2 below, provides the location of a number of identified immunosuppressive domains.

TABLE 2

Localization of identified immunosuppressive domains

| Family (-viridae), Subfamily (-virinae), Genus (-virus) or Species (-virus) of viruses | Localization of prototype immunosuppressive domain | Reference |
| --- | --- | --- |
| All Flavivirus | Protein E (SEQ ID NO: 219) 98-DRGWGNXCGXFGKGXX-113 | Seligman SJ. Constancy and diversity in the flavivirus fusion peptide. Virol J. 2008 Feb. 14; 5:27. |
| All Flavivirus (e.g. Dengue 3) | Protein E (SEQ ID NO: 220) 416-GDTAWDFGSVGGVLNSLGK-434 | FIG. 1 Schmidt AG, Yang PL, Harrison SC. Peptide inhibitors of dengue-virus entry target a late-stage fusion intermediate. PLoS Pathog. 2010 Apr. 8; 6(4): e1000851. |
| Hepatitis C | E2 (SEQ ID NO: 3) 71-GLIHLHQNIVDVQYLYG-87 | Albecka A, Montserret R, Krey T, Tarr AW, Diesis E, Ball JK, Descamps V, Duverlie G, Rey F, Penin F, Dubuisson J. Identification of new functional regions in hepatitis C virus envelope glycoprotein E2. J Virol. 2011 Feb.; 85(4): 1777-92. Epub 2010 Dec 8. |
| Influenza A1-16 Influenza B | HA2 (SEQ ID NO: 4) 1-GLFGAIAGFIENGWEG-16 | Cross KJ, Wharton SA, Skehel JJ, Wiley DC, Steinhauer DA. Studies on influenza haemagglutinin fusion peptide mutants generated by reverse genetics. EMBO J. 2001 Aug. 15; 20(16): 4432-42. |

According to an embodiment, the invention concerns a pharmaceutical composition comprising a mutated peptide, an envelope protein, a mutated envelope protein, an antigen, a nucleic acid sequence, a vector, an antibody or a vaccine composition according to any of the preceding claims, and at least one pharmaceutically acceptable excipient, diluents or carrier.

According to an embodiment, the invention concerns a use of a mutated peptide, an envelope protein, a mutated envelope protein, an antigen, a nucleic acid sequence, a vector or an antibody according to any of the preceding claims, for a medical purpose, such as for the treatment, amelioration or prevention of a clinical condition, such as for the manufacture of a medicament for the treatment, amelioration or prevention of a clinical condition.

According to an embodiment, the invention concerns a method of treating or ameliorating the symptoms of an According to an embodiment, an immunosuppressive domain may be identified by its position, e.g. as indicated in Table 2.

According to an embodiment, the invention concerns an immunosuppressive domain identified by its position.

According to an embodiment, the invention concerns an immunosuppressive domain identified by its secondary, tertiary or quaternary structure in the folded fusion protein.

According to an embodiment, the invention concerns an entity selected among the group consisting of a mutated peptide, an envelope protein, a mutated envelope protein, an antigen, a nucleic acid sequence and a vector, wherein an immunosuppressive domain identified by its position, has been modified or mutated in order to suppress its immunosuppressive properties.

All cited references are incorporated by reference.

The accompanying Figures and Examples are provided to explain rather than limit the present invention. It will be clear to the person skilled in the art that aspects, embodiments and claims of the present invention may be combined.

EXAMPLES

Peptide Solutions

The peptides were either dissolved in water or in cases of low water solubility, 5% DMSO solutions were used to dissolve the peptides.

Assay to Measure the Immunosuppressive Activity of Peptides Derived from Viral Surface Proteins or their Mutants The peptides can be prepared by different means including, but not limited to, solid phase synthesis commonly used for such purposes. The peptides can be dimerized using a cysteine residue either at the N- or C-terminal or in the middle of the peptide or by using any other molecule or atom that is covalently bound to peptide molecules.

The peptides can be coupled to a carrier protein such as BSA by covalent bounds including, but not limited to, disulfide bridges between the peptide cysteine residues and the carrier protein or through amino groups including those in the side chain or Lysine residues.

The peptides can have non-viral derived amino acids added to their C-terminal for increasing their water solubility.

Assay to Test the Immunosuppressive Activity of Peptides Experiment Design

Human Peripheral Blood Mononuclear Cells (PBMC) are prepared freshly from healthy donors. These are stimulated by Con A (5 ug/mL) concomitant to peptide addition at different concentrations (i.e. 25 uM, 50 uM and 100 uM). Cultures are maintained and lymphocyte proliferation is measured 72 hrs later by EdU incorporation and Click-iT labelling with Oregon Green (Invitrogen, Denmark) as recommended by the manufacturer. The degree of activated lymphocytes is proportional to the fluorescence detection.

CTLL-2 Assay 100.000 CTLL-2 cells are seeded pr. well in a 48 well-plate (Nunc) in 200 uL of medium (RPMI+2 mM L-glutamine+1 mM Na-pyruvat+10% FCS+0.5 ng/mL IL-2) 2 hours later the peptides are added to the wells. 24 h later the cells are labeled using the Click-it reaction kit (Invitrogen cat. # C35002). The fluorescence of the cells is measured on a flow cytometer. The degree of proliferation in each sample is proportional to the detected fluorescence.

Test of Immunosuppression from Monomer and Dimeric Peptides 100.000 CTLL-2 cells were seeded pr. well in a 48 well-plate (Nunc) in 200 uL of medium (RPMI+2 mM L-glutamine+1 mM Na-pyruvat+10% FCS+0.5 ng/mL IL-2) 2 hours later the peptides were added to the wells. 24 h later the cells were labeled using the Click-it reaction kit (Invitrogen cat. # C35002). The fluorescence of the cells was measured on a flow cytometer. The degree of proliferation in each sample is proportional to the detected fluorescence.

Quantification of Proliferation Inhibition

The degree of inhibition of proliferation of CTLL-2 cells is visualized in the diagrams in the figures. The ratios are calculated by dividing the number of labeled cells (growing cells) in cultures in presence of peptide with cultures in absence of peptides, but added the same volume of the solute that was used to dissolve the peptides. That is in cases where the peptides were dissolved in 5% DMSO, the same volume of 5% DMSO was added to the control cells.

FIGURES

FIG. 1 shows the result of an experiment using Influenza derived peptides, and the effect of the dimeric peptides on proliferation of CTLL-2 cells. The peptides are coupled through an ss-bond involving the cysteine residues. The wt INF peptide inhibits synthesis of new DNA, whereas the non-IS #1 peptide has a much less and the non-IS #2 peptide no significant effect.

```
INF wt:
                                    (SEQ ID NO: 214)
GLFGAIAGFIENGWEGCGGEKEKEK

INF non-IS #1:
                                    (SEQ ID NO: 215)
GLFGAAGFIENGWEGCGGEKEKEK

INF non-IS #2:
                                    (SEQ ID NO: 216)
GLFAGFIENGWEGCGGEKEKEK
```

Figure 2:
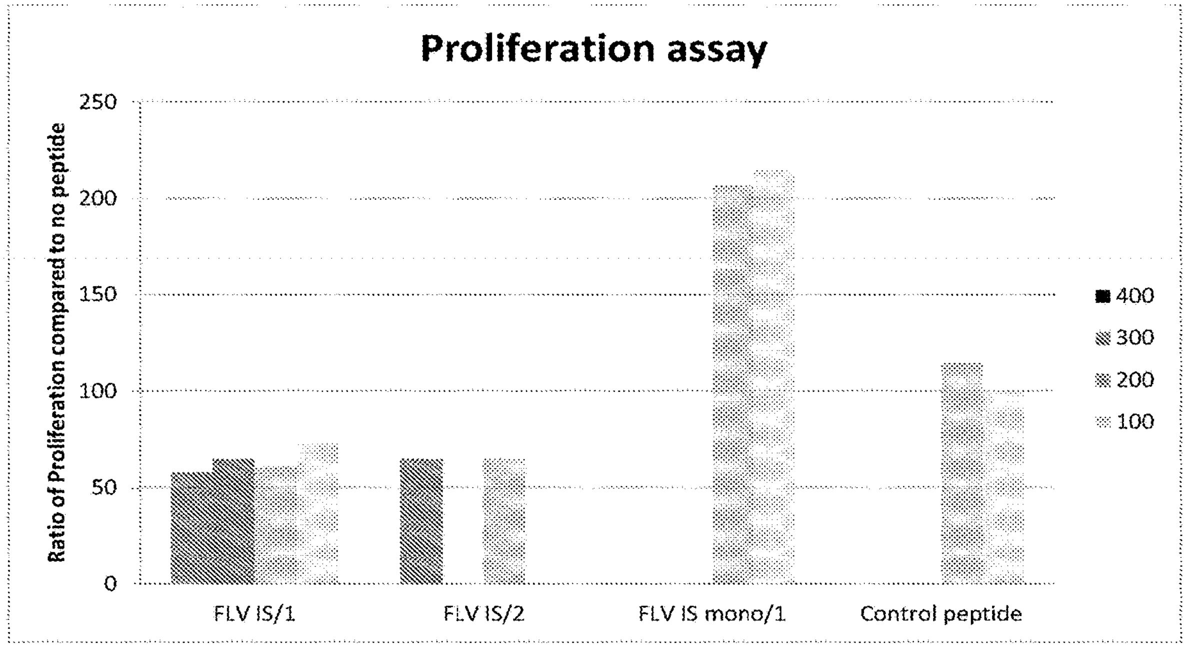

FIG. 2 shows the result of two independent experiments on Flavi virus derived peptides. FLV IS/1 and FLV IS/2 are two independent experiments using the dimerized peptide: In both cases, a significant inhibition of proliferation of CTLL-2 cells is evident, while the monomeric peptide has no effect.

```
FLV IS/1 and FLV IS/2:
                                    (SEQ ID NO: 2)
dimeric DRGWGNGCGLFGKG

FLV IS mono/1:
                                    (SEQ ID NO: 2)
monomeric DRGWGNGCGLFGKG
```

Control peptide: a dimerized non-immune suppressive control peptide.

The concentrations are given in μM.

Figure 3:
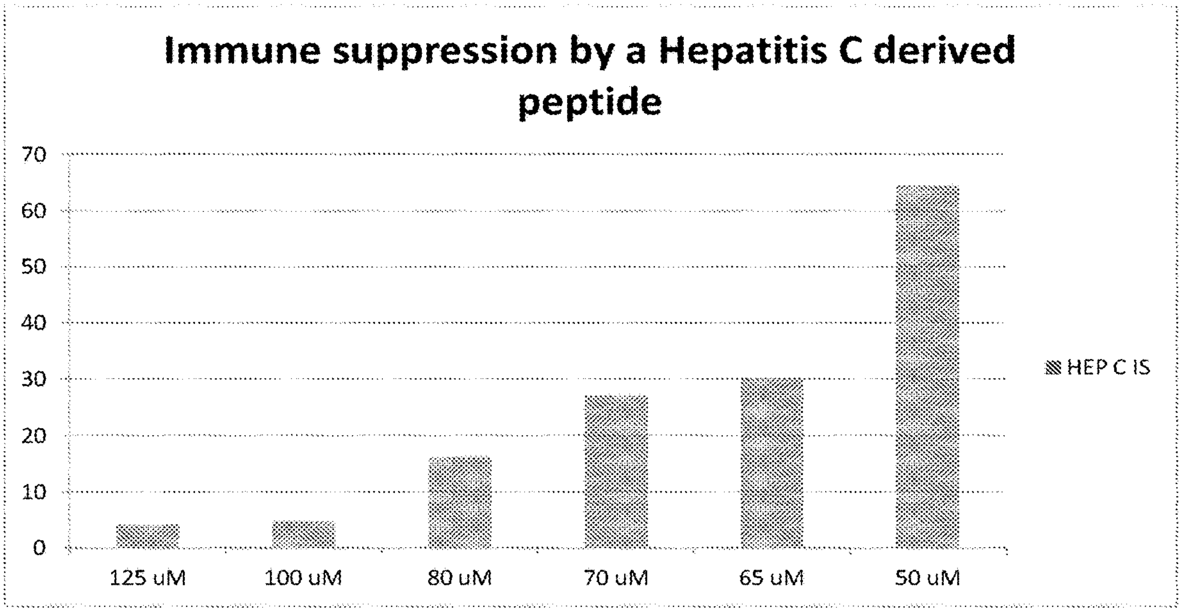

FIG. 3 shows another experimental result. The dimeric peptide derived from Hepatitis C surface protein inhibits proliferation of T-cells in a concentration dependent manner.

```
Hep C IS peptide has the sequence:
                                    (SEQ ID NO: 217)
PALSTGLIHLHQNIVDVQCGGEKEKEK
```

Figure 4:
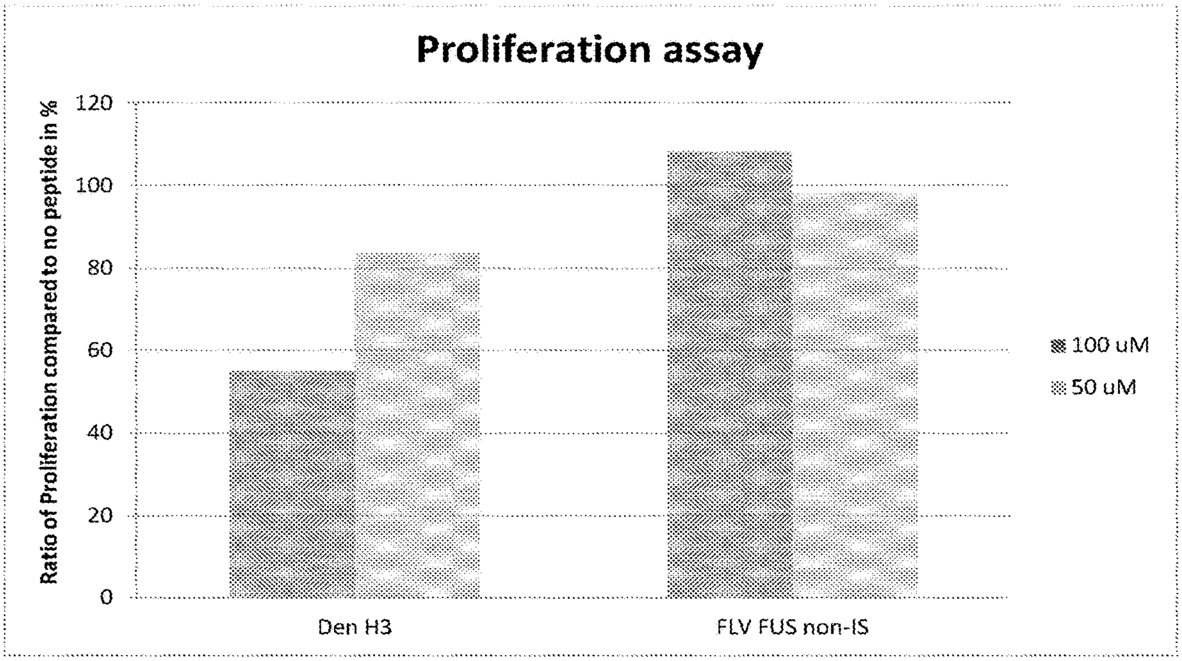

FIG. 4 shows yet an experimental result. The effect of the dimeric peptides derived from Flavi viruses on proliferation of CTLL-2 cells. The peptides are coupled through an ss-bond using the cysteine residues. FLV FUS non-IS is representative of a non-immune suppressive mutant.

```
Den H3:
                                    (SEQ ID NO: 218)
GDTAWDFGSIGGVFTSVGKCGGEKEKEK

FLV FUS non-IS:
                                    (SEQ ID NO: 202)
DRGWGNGCGDFGKG
```

APPENDIX

Classes of Enveloped RNA Viruses that Contain Human Pathogens

Flaviridae (Type II Fusion)

Flaviviridae have monopartite, linear, single-stranded RNA genomes of positive polarity, 9.6- to 12.3-kilobase in length. Virus particles are enveloped and spherical, about 40-60 nm in diameter.

Major diseases caused by the Flaviviridae family include:

Dengue fever

Japanese encephalitis

Kyasanur Forest disease

Murray Valley encephalitis

St. Louis encephalitis

Tick-borne encephalitis

West Nile encephalitis

Yellow fever

Hepatitis C Virus Infection

Existing Vaccines for Flaviridae

The successful yellow fever 17D vaccine, introduced in 1937, produced dramatic reductions in epidemic activity. Effective killed Japanese encephalitis and Tick-borne encephalitis vaccines were introduced in the middle of the 20th century. Unacceptable adverse events have prompted change from a mouse-brain killed Japanese encephalitis vaccine to safer and more effective second generation Japanese encephalitis vaccines. These may come into wide use to effectively prevent this severe disease in the huge populations of Asia—North, South and Southeast. The dengue viruses produce many millions of infections annually due to transmission by a successful global mosquito vector. As mosquito control has failed, several dengue vaccines are in varying stages of development. A tetravalent chimeric vaccine that splices structural genes of the four dengue viruses onto a 17D yellow fever backbone is in Phase III clinical testing.

Genus Flavivirus

Flaviviruses share a common size (40-65 nm), symmetry (enveloped, icosahedral nucleocapsid), nucleic acid (positive-sense, single stranded RNA approximately 10,000-11,000 bases), and appearance in the electron microscope.

These viruses are transmitted by the bite from an infected arthropod (mosquito or tick). Human infections with these viruses are typically incidental, as humans are unable to replicate the virus to high enough titres to reinfect arthropods and thus continue the virus life cycle. The exceptions to this are yellow fever and dengue viruses, which still require mosquito vectors, but are well-enough adapted to humans as to not necessarily depend upon animal hosts (although both continue have important animal transmission routes as well).

Genus Hepacivirus (type species Hepatitis C virus, the single member)

Hepatitis C is an infectious disease affecting the liver, caused by the hepatitis C virus (HCV). The infection is often asymptomatic, but once established, chronic infection can progress to scarring of the liver (fibrosis), and advanced scarring (cirrhosis), which is generally apparent after many years. In some cases, those with cirrhosis will go on to develop liver failure or other complications of cirrhosis, including liver cancer or life threatening esophageal varices and gastric varices. The hepatitis C virus is spread by blood-to-blood contact. Most people have few, if any symptoms after the initial infection, yet the virus persists in the liver in about 85% of those infected. Persistent infection can be treated with medication, peg-interferon and ribavirin being the standard-of-care therapy. Overall, 51% are cured. Those who develop cirrhosis or liver cancer may require a liver transplant, and the virus universally recurs after the transplant takes place. An estimated 180 million people worldwide are infected with hepatitis C. Hepatitis C is not known to cause disease in other animals. No vaccine against hepatitis C is currently available. The existence of hepatitis C (originally “non-A non-B hepatitis”) was postulated in the 1970s and proven in 1989. It is one of five known hepatitis viruses: A, B, C, D, and E.

The hepatitis C virus is a small (50 nm in size), enveloped, single-stranded, positive sense RNA virus. There are six major genotypes of the hepatitis C virus, which are indicated numerically (e.g., genotype 1, genotype 2, etc.). Based on the NS5 gene there are three major and eleven minor genotypes. The major genotypes diverged about 300-400 years ago from the ancestor virus. The minor genotypes diverged about 200 years ago from their major genotypes. All of the extant genotypes appear to have evolved from genotype 1 subtype 1b.

The hepatitis C virus is transmitted by blood-to-blood contact. In developed countries, it is estimated that 90% of persons with chronic HCV infection were infected through transfusion of unscreened blood or blood products or via injecting drug use or sexual exposure. In developing countries, the primary sources of HCV infection are unsterilized injection equipment and infusion of inadequately screened blood and blood products.

Genus Pestivirus

TogaviridaeType II Fusion

The Togaviridae are a family of viruses, including the following genera:

Genus Alphavirus;

Alphaviruses have a positive sense single stranded RNA genome. There are 27 alphaviruses, able to infect various vertebrates such as humans, rodents, fish, birds, and larger mammals such as horses as well as invertebrates. Transmission between species and individuals occurs mainly via mosquitoes making the alphaviruses a contributor to the collection of Arboviruses—or Arthropod Borne Viruses. Alphaviruses particles are enveloped, have a 70 nm diameter, tend to be spherical and have a 40 nm isometric nucleocapsid.

There are two open reading frames (ORF's) in the genome, non-structural and structural. The first is non structural and encodes proteins for transcription and replication of viral RNA, and the second encodes three structural proteins: the core nucleocapsid protein C, and the envelope proteins P62 and E1 that associate as a heterodimer. The viral membrane-anchored surface glycoproteins are responsible for receptor recognition and entry into target cells through membrane fusion. The proteolytic maturation of P62 into E2 and E3 causes a change in the viral surface. Together the E1, E2, and sometimes E3, glycoprotein “spikes” form an E1/E2 dimer or an E1/E2/E3 trimer, where E2 extends from the centre to the vertices, E1 fills the space between the vertices, and E3, if present, is at the distal end of the spike. Upon exposure of the virus to the acidity of the endosome, E1 dissociates from E2 to form an E1 homotrimer, which is necessary for the fusion step to drive the cellular and viral membranes together. The alphaviral glycoprotein E1 is a class II viral fusion protein. The structure of the Semliki Forest virus revealed a structure that is similar to that of flaviviral glycoprotein E, with three structural domains in the same primary sequence arrangement. The E2 glycoprotein functions to interact with the nucleocapsid through its cytoplasmic domain, while its ectodomain is responsible for binding a cellular receptor. Most alphaviruses lose the peripheral protein E3, but in Semliki viruses it remains associated with the viral surface.

Genus *Rubivirus;*

Genus *Rubivirus*

Bunyaviridae Type II Fusion Mechanism

Bunyaviridae is a family of negative-stranded RNA viruses. Though generally found in arthropods or rodents, certain viruses in this family occasionally infect humans. Some of them also infect plants.

Bunyaviridae are vector-borne viruses. With the exception of Hantaviruses, transmission occurs via an arthropod vector (mosquitos, tick, or sandfly). Hantaviruses are transmitted through contact with deer mice feces. Incidence of infection is closely linked to vector activity, for example, mosquito-borne viruses are more common in the summer.

Human infections with certain Bunyaviridae, such as Crimean-Congo hemorrhagic fever virus, are associated with high levels of morbidity and mortality, consequently handling of these viruses must occur with a Biosafety level 4 laboratory. They are also the cause of severe fever with thrombocytopenia syndrome.

Hanta virus or Hantavirus Hemorrhagic fever, common in Korea, Scandinavia, Russia, and the American southwest, is associated with high fever, lung edema and pulmonary failure. Mortality is around 55%.

The antibody reaction plays an important role in decreasing levels of viremia.

Genus Hantavirus; type species: Hantaan virus

Hantaviruses are negative sense RNA viruses in the Bunyaviridae family. Humans may be infected with hantaviruses through rodent bites, urine, saliva or contact with rodent waste products. Some hantaviruses cause potentially fatal diseases in humans, hemorrhagic fever with renal syndrome (HFRS) and hantavirus pulmonary syndrome (HPS), but others have not been associated with human disease. HPS cannot be transmitted person-to-person. The name hantavirus is derived from the Hantan River area in South Korea, which provided the founding member of the group: Hantaan virus (HTNV), isolated in the late 1970s by Ho-Wang Lee and colleagues. HTNV is one of several hantaviruses that cause HFRS, formerly known as Korean hemorrhagic fever.

Genus Ortho-Bunya-Virus

The orthobunyaviruses are maintained in nature by sylvatic transmission cycles between hematophagous mosquitoes and susceptible mammalian hosts, principally rodents and other small mammals. Several members of the California serogroup of orthobunyaviruses, including La Crosse (LAC) and Tahyna (TAH) viruses, are significant human pathogens. LAC virus is an important cause of pediatric encephalitis and aseptic meningitis in the Midwestern United States where approximately 100 cases are reported annually; TAH virus, indigenous to central Europe, is associated with influenzalike febrile illnesses. La Crosse virus is a NIAID Category B priority pathogen.

The orthobunyaviruses are enveloped, negative-stranded RNA viruses with a tripartite genome comprised of large (L), medium (M), and small (S) segments The M segment encodes three proteins in a single open reading frame (ORF): two surface transmembrane glycoproteins, herein referred to as Gn (G2) and Gc (G1), respectively, to delineate their order in the precursor polyprotein, and NSm, a protein of unknown function. Gn and Gc are thought to associate as a heteromultimer after cleavage of the polyprotein.

Genus Phlebovirus; type species: Rift Valley fever virus

Phlebovirus is one of five genera of the family Bunyaviridae. The Phlebovirus genus currently comprises over 70 antigenically distinct serotypes, only a few of which have been studied. The 68 known serotypes are divided into two groups: the Phlebotomus fever viruses (the sandfly group, transmitted by Phlebotominae sandflies) comprises 55 members and the Uukuniemi group (transmitted by ticks) comprises the remaining 13 members.

Of these 68 serotypes, eight of them have been linked to disease in humans. They are: Alenquer virus, Candiru virus, Chagres virus, Naples virus, Punta Toro virus, Rift Valley fever, Sicilian virus, and Toscana virus. Recently identified is another human pathogenic serotype, the SFTS virus.

Rift Valley Fever (RVF) is a viral zoonosis (affects primarily domestic livestock, but can be passed to humans) causing fever. It is spread by the bite of infected mosquitoes, typically the *Aedes* or *Culex* genera. The disease is caused by the RVF virus, a member of the genus Phlebovirus (family Bunyaviridae). The disease was first reported among livestock in Kenya around 1915, but the virus was not isolated until 1931. RVF outbreaks occur across sub-Saharan Africa, with outbreaks occurring elsewhere infrequently (but sometimes severely—in Egypt in 1977-78, several million people were infected and thousands died during a violent epidemic. In Kenya in 1998, the virus claimed the lives of over 400 Kenyans. In September 2000 an outbreak was confirmed in Saudi Arabia and Yemen).

In humans the virus can cause several different syndromes. Usually sufferers have either no symptoms or only a mild illness with fever, headache, myalgia and liver abnormalities. In a small percentage of cases (<2%) the illness can progress to hemorrhagic fever syndrome, meningoencephalitis (inflammation of the brain), or affecting the eye. Patients who become ill usually experience fever, generalized weakness, back pain, dizziness, and weight loss at the onset of the illness. Typically, patients recover within 2-7 days after onset.

Approximately 1% of human sufferers die of the disease. Amongst livestock the fatality level is significantly higher. In pregnant livestock infected with RVF there is the abortion of virtually 100% of fetuses. An epizootic (animal disease epidemic) of RVF is usually first indicated by a wave of unexplained abortions.

Orthomyxoviridae Type I Fusion

The Orthomyxoviridae (orthos, Greek for “straight”; myxa, Greek for “mucus”)' are a family of RNA viruses that includes five genera: Influenzavirus A, Influenzavirus B, Influenzavirus C, Isavirus and Thogotovirus. A sixth has recently been described. The first three genera contain viruses that cause influenza in vertebrates, including birds (see also avian influenza), humans, and other mammals. Isaviruses infect salmon; thogotoviruses infect vertebrates and invertebrates, such as mosquitoes and sea lice.

The three genera of Influenzavirus, which are identified by antigenic differences in their nucleoprotein and matrix protein infect vertebrates as follows:

- Influenzavirus A infects humans, other mammals, and birds, and causes all flu pandemics
- Influenzavirus B infects humans and seals
- Influenzavirus C infects humans and pigs Paramyxoviridae Type I Fusion Mechanism The fusion protein F projects from the envelope surface as a trimer, and mediates cell entry by inducing fusion between the viral envelope and the cell membrane by class I fusion. One of the defining characteristics of members of the paramyxoviridae family is the requirement for a neutral pH for fusogenic activity. A number of important human diseases are caused by paramyxoviruses. These include mumps, measles, which caused 745,000 deaths in 2001 and respiratory syncytial virus (RSV) which is the major cause of bronchiolitis and pneumonia in infants and children. The parainfluenza viruses are the second most common causes of respiratory tract disease in infants and children. They can cause pneumonia, bronchitis and croup in children and the elderly.

Human metapneumovirus, initially described in about 2001, is also implicated in bronchitis, especially in children.

genus *Paramyxoviruses* are also responsible for a range of diseases in other animal species, for example canine distemper virus (dogs), phocine distemper virus (seals), cetacean morbillivirus (dolphins and porpoises) Newcastle disease virus (birds), and rinderpest virus (cattle). Some paramyxoviruses such as the henipaviruses are zoonotic pathogens, occurring naturally in an animal host, but also able to infect humans.

Hendra virus (HeV) and Nipah virus (NiV) in the genus Henipavirus have emerged in humans and livestock in Australia and Southeast Asia. Both viruses are contagious, highly virulent, and capable of infecting a number of mammalian species and causing potentially fatal disease. Due to the lack of a licensed vaccine or antiviral therapies, HeV and NiV are designated as biosafety level (BSL) 4 agents. The genomic structure of both viruses is that of a typical paramyxovirus.

Genus *Pneumovirinae*

Genus *Pneumovirus* (type species Human respiratory syncytial virus, others include Bovine respiratory syncytial virus)

Human respiratory syncytial virus (RSV) is a virus that causes respiratory tract infections. It is the major cause of lower respiratory tract infections and hospital visits during infancy and childhood. A prophylactic medication (not a vaccine) exists for preterm birth (under 35 weeks gestation) infants and infants with a congenital heart defect (CHD) or bronchopulmonary dysplasia (BPD). Treatment is limited to supportive care, including oxygen therapy.

In temperate climates there is an annual epidemic during the winter months. In tropical climates, infection is most common during the rainy season.

In the United States, 60% of infants are infected during their first RSV season and nearly all children will have been infected with the virus by 2-3 years of age. en.wikipedia.org/wiki/Respiratory_syncytial_virus-cite_note-Glezen86-0. Of those infected with RSV, 2-3% will develop bronchiolitis, necessitating hospitalization. Natural infection with RSV induces protective immunity which wanes over time—possibly more so than other respiratory viral infections—and thus people can be infected multiple times. Sometimes an infant can become symptomatically infected more than once, even within a single RSV season. Severe RSV infections have increasingly been found among elderly patients.

RSV is a negative-sense, single-stranded RNA virus of the family Paramyxoviridae, which includes common respiratory viruses such as those causing measles and mumps. RSV is a member of the paramyxovirus subfamily *Pneumovirinae*. Its name comes from the fact that F proteins on the surface of the virus cause the cell membranes on nearby cells to merge, forming syncytia.

Coronaviriridae Type I Fusion

Coronaviruses primarily infect the upper respiratory and gastrointestinal tract of mammals and birds. Four to five different currently known strains of coronaviruses infect humans. The most publicized human coronavirus, SARS-CoV which causes SARS, has a unique pathogenesis because it causes both upper and lower respiratory tract infections and can also cause gastroenteritis. Coronaviruses are believed to cause a significant percentage of all common colds in human adults. Coronaviruses cause colds in humans primarily in the winter and early spring seasons. The significance and economic impact of coronaviruses as causative agents of the common cold are hard to assess because, unlike rhinoviruses (another common cold virus), human coronaviruses are difficult to grow in the laboratory.

Coronaviruses also cause a range of diseases in farm animals and domesticated pets, some of which can be serious and are a threat to the farming industry. Economically significant coronaviruses of farm animals include porcine coronavirus (transmissible gastroenteritis coronavirus, TGE) and bovine coronavirus, which both result in diarrhea in young animals. Feline Coronavirus: 2 forms, Feline enteric coronavirus is a pathogen of minor clinical significance, but spontaneous mutation of this virus can result in feline infectious peritonitis (FIP), a disease associated with high mortality. There are two types of canine coronavirus (CCoV), one that causes mild gastrointestinal disease and one that has been found to cause respiratory disease. Mouse hepatitis virus (MHV) is a coronavirus that causes an epidemic murine illness with high mortality, especially among colonies of laboratory mice. Prior to the discovery of SARS-CoV, MHV had been the best-studied coronavirus both in vivo and in vitro as well as at the molecular level. Some strains of MHV cause a progressive demyelinating encephalitis in mice which has been used as a murine model for multiple sclerosis. Significant research efforts have been focused on elucidating the viral pathogenesis of these animal coronaviruses, especially by virologists interested in veterinary and zoonotic diseases.

SARS-Coronavirus

SARS is most closely related to group 2 coronaviruses, but it does not segregate into any of the other three groups of coronaviruses. SARS was determined to be an early split off from the group 2 coronaviruses based on a set of conserved domains that it shares with group 2. A main difference between group 2 coronovirus and SARS is the nsp3 replicase subunit encoded by ORF1a. SARS does not have a papain-like proteinase 1.

Arenaviridae: Glycoprotein G2 is a Type I Fusion

Arenavirus is a genus of virus that infects rodents and occasionally humans. At least eight Arenaviruses are known to cause human disease. The diseases derived from Arenaviruses range in severity. Aseptic meningitis, a severe human disease that causes inflammation covering the brain and spinal cord, can arise from the Lymphocytic choriomeningitis virus (LCMV) infection. Hemorrhagic fever syndromes are derived from infections such Guanarito virus (GTOV), Junin virus (JUNV), Lassa virus (LASV) causing Lassa fever, Machupo virus (MACV), Sabia virus (SABV), or Whitewater Arroyo virus (WWAV).[1] Arenaviruses are divided into two groups; the Old World or New World. The differences between these groups are distinguished geographically and genetically. Because of the epidemiological association with rodents, some arenaviruses and bunyaviruses are designated as Roboviruses.

LCMV-Lassa virus (Old World) complex:

Ippy virus

Lassa virus

Lujo virus

Lymphocytic choriomeningitis virus

LCMV infection manifests itself in a wide range of clinical symptoms, and may even be asymptomatic for immunocompetent individuals. Onset typically occurs between one or two weeks after exposure to the virus and is followed by a biphasic febrile illness. During the initial or prodromal phase, which may last up to a week, common symptoms include fever, lack of appetite, headache, muscle aches, malaise, nausea, and/or vomiting. Less frequent symptoms include a sore throat and cough, as well as joint, chest, and parotid pain. The onset of the second phase occurs several days after recovery, and consists of symptoms of meningitis or encephalitis. Pathological findings during the first stage consist of leukopenia and thrombocytopenia. During the second phase, typical findings include elevated protein levels, increased leukocyte count, or a decrease in glucose levels of the cerebrospinal fluid).

Congenital Infection

Lymphocytic choriomeningitis is a particular concern in obstetrics, as vertical transmission is known to occur. For immunocompetent mothers, there is no significant threat, but the virus has damaging effects upon the fetus. If infection occurs during the first trimester, LCMV results in an increased risk of spontaneous abortion. Later congenital infection may lead to malformations such as chorioretinitis, intracranial calcifications, hydrocephalus, microcephaly or macrocephaly, mental retardation, and seizures. Other findings include chorioretinal scars, optic atrophy, and cataracts. Mortality among infants is approximately 30%. Among the survivors, two thirds have lasting neurologic abnormalities. If a woman has come into contact with a rodent during pregnancy and LCM symptoms are manifested, a blood test is available to determine previous or current infection. A history of infection does not pose a risk for future pregnancies.

Human-to-Human Transmission Through Organ Donation

In May 2005, four solid-organ transplant recipients contracted an illness that was later diagnosed as lymphocytic choriomeningitis. All received organs from a common donor, and within a month of transplantation, three of the four recipients had died as a result of the viral infection. Epidemiologic investigation traced the source to a pet hamster that the organ donor had recently purchased from a Rhode Island pet store. A similar case occurred in Massachusetts in 2008. Currently, there is not a LCMV infection test that is approved by the Food and Drug Administration for organ donor screening. The Morbidity and Mortality Weekly Report advises health-care providers to "consider LCMV infection in patients with aseptic meningitis and encephalitis and in organ transplant recipients with unexplained fever, hepatitis, or multisystem organ failure."

Hepadnaviridae: Fusion Mechanism Neither Type I Nor Type II

Hepadnaviruses are a family of viruses which can cause liver infections in humans and animals. There are two recognized genera Hepadnaviruses have very small genomes of partially double-stranded, partially single stranded circular DNA. The genome consists of two uneven strands of DNA. One has a negative-sense orientation, and the other, shorter, strand has a positive-sense orientation.

As it is a group 7 virus, replication involves an RNA intermediate. Three main open reading frames are encoded (ORFs) and the virus has four known genes which encode the core protein, the virus polymerase, surface antigens (preS1, preS2, and S) and the X protein. The X protein is thought to be non-structural; however, its function and significance are poorly understood.

Rhabdoviridae Fusion Mechanism Neither Type I Nor Type II

Rhabdoviruses carry their genetic material in the form of negative-sense single-stranded RNA. They typically carry genes for five proteins: large protein (L), glycoprotein (G), nucleoprotein (N), phosphoprotein (P), and matrix protein (M). Rhabdoviruses that infect vertebrates are bullet-shaped. The prototypical and best studied rhabdovirus is vesicular stomatitis virus.

Rhabdoviruses are important pathogens of animals and plants. Rhabdoviruses include RaV (Rabies virus), VSV (Vesicular stomatitis virus). Rhabdoviruses are transmitted to hosts by arthropods, such as aphids, planthoppers, leafhoppers, black flies, sandflies, and mosquitoes.

ADDITIONAL REFERENCES

1. Sapir, A., et al., *Viral and developmental cell fusion mechanisms: conservation and divergence. Dev Cell,* 2008. 14(1): *p.* 11-21.
2. Cianciolo, G. J., et al., *Murine malignant cells synthesize a* 19,000-*dalton protein that is physicochemically and antigenically related to the immunosuppressive retroviral protein, P15E. J Exp Med,* 1983. 158(3): p. 885-900.
3. Hebebrand, L. C., et al., *Inhibition of human lymphocyte mitogen and antigen response by a* 15,000-*dalton protein from feline leukemia virus. Cancer Res,* 1979. 39(2 Pt 1): p. 443-7.
4. Cianciolo, G. J., et al., *Macrophage accumulation in mice is inhibited by low molecular weight products from murine leukemia viruses. J Immunol,* 1980. 124(6): p. 2900-5.
5. Mangeney, M. and T. Heidmann, *Tumor cells expressing a retroviral envelope escape immune rejection in vivo. Proc Natl Acad Sci USA,* 1998. 95(25): p. 14920-5.
6. Mangeney, M., et al., *Placental syncytins: Genetic disjunction between the fusogenic and immunosuppressive activity of retroviral envelope proteins. Proc Natl Acad Sci USA,* 2007. 104(51): p. 20534-9.
7. Cianciolo, G. J., et al., *Inhibition of lymphocyte proliferation by a synthetic peptide homologous to retroviral envelope proteins. Science,* 1985. 230(4724): p. 453-5.
8. Cianciolo, G. J., H. Bogerd, and R. Snyderman, *Human retrovirus-related synthetic peptides inhibit T lymphocyte proliferation. Immunol Lett,* 1988. 19(1): p. 7-13.
9. Yaddanapudi, K., et al., *Implication of a retrovirus-like glycoprotein peptide in the immunopathogenesis of Ebola and Marburg viruses. Faseb J,* 2006. 20(14): p. 2519-30.
10. Haraguchi, S., et al. *Differential modulation of Th*1- *and Th*2-*related cytokine mRNA expression by a synthetic peptide homologous to a conserved domain within retro viral envelope protein. Proc NatlAcadSci USA,* 1995. 92, 3611-15.
11. Harrell, R. A., et al Cianciolo. *Suppression of the respiratory burst of human monocytes by a synthetic peptide homologous to envelope proteins of human and animal retroviruses. J Immunol,* 1986. 136, 3517-520.
12. Kleinerman, E. S., et al. Lachman. *A synthetic peptide homologous to the envelope proteins of retroviruses inhibits monocyte-mediated killing by inactivating interleukin* 1. *J Immunol,* 1987. 139, 2329-337.
13. Schlecht-Louf G., et al. *Retroviral infection in vivo requires an immune escape virulence factor encrypted in the envelope protein of oncoretroviruses. Proc Natl Acad Sci USA.* 2010 Feb. 23; 107(8):3782-7.
14. Volchkov V E et al. The envelope glycoprotein of Ebola virus contains an immunosuppressive-like domain similar to oncogenic retroviruses. FEBS Lett. 1992 Jul. 6; 305 (3):181-4.
15. Cross K J, Wharton S A, Skehel J J, Wiley D C, Steinhauer D A. Studies on influenza haemagglutinin fusion peptide mutants generated by reverse genetics. EMBO J. 2001 Aug. 15; 20(16):4432-42.

The invention claimed is:

1. A dimeric form of a synthetic peptide comprising an immunosuppressive domain, wherein the immunosuppressive domain comprises the amino acid sequence of SEQ ID NO:4, and further comprises a cysteine residue at an N-terminal or C-terminal position, and wherein the peptide is dimerized through said cysteine residue.

2. The dimeric form of a synthetic peptide according to claim 1, wherein said dimerization is through a disulfide bond involving said cysteine residue.

3. The dimeric form of a synthetic peptide according to claim 1, wherein said peptide comprises the amino acid sequence of SEQ ID NO:214.

4. The dimeric form of a synthetic peptide according to claim 1, wherein said peptide is derived from a virus different from the group consisting of retrovirus and filovirus.

5. The dimeric form of a synthetic peptide according to claim 1, wherein said peptide is derived from an influenza virus.

6. The dimeric form of a synthetic peptide according to claim 1, wherein said peptide is derived from a virus different from lentivirus.

7. The dimeric form of a synthetic peptide according to claim 1, wherein said peptide is recombinant or obtained by recombinant technology.

8. A pharmaceutical composition comprising the dimeric for of a synthetic peptide according to claim 1.

9. The pharmaceutical composition according to claim 8 further comprising at least one pharmaceutically acceptable excipient, diluent or carrier.

10. A nucleic acid sequence encoding the synthetic peptide according to claim 1.

11. An isolated eukaryotic expression vector comprising the nucleic acid sequence according to claim 10.

12. The isolated eukaryotic expression vector according to claim 11, wherein said isolated eukaryotic expression vector is a viral vector.

13. The isolated eukaryotic expression vector according to claim 12, wherein said viral vector is selected from the group consisting of vaccinia virus, measles virus, retroviridae, baculovirus, and adenovirus.

* * * * *